US008709483B2

(12) United States Patent
Farokhzad et al.

(10) Patent No.: US 8,709,483 B2
(45) Date of Patent: Apr. 29, 2014

(54) SYSTEM FOR TARGETED DELIVERY OF THERAPEUTIC AGENTS

(75) Inventors: Omid C. Farokhzad, Chestnut Hill, MA (US); Jianjun Cheng, Champaign, IL (US); Benjamin A. Teply, Omaha, NE (US); Robert S. Langer, Newton, MA (US); Stephen E. Zale, Hopkinton, MA (US)

(73) Assignees: Massachusetts Institute of Technology, Cambridge, MA (US); The Brigham and Women's Hospital, Inc., Boston, MA (US)

( * ) Notice: Subject to any disclaimer, the term of this patent is extended or adjusted under 35 U.S.C. 154(b) by 943 days.

(21) Appl. No.: 12/239,136

(22) Filed: Sep. 26, 2008

(65) Prior Publication Data
US 2010/0266491 A1   Oct. 21, 2010

Related U.S. Application Data

(63) Continuation of application No. PCT/US2007/007927, filed on Mar. 30, 2007.

(60) Provisional application No. 60/788,532, filed on Mar. 31, 2006.

(51) Int. Cl.
A61K 9/14 (2006.01)
A61K 38/00 (2006.01)
C12N 15/11 (2006.01)

(52) U.S. Cl.
USPC .................. 424/489; 514/19.5; 514/44 A

(58) Field of Classification Search
None
See application file for complete search history.

(56) References Cited

U.S. PATENT DOCUMENTS

| | | |
|---|---|---|
| 3,766,774 A | 10/1973 | Clark |
| 4,270,537 A | 6/1981 | Romaine |
| 4,446,122 A | 5/1984 | Chu et al. |
| 4,596,556 A | 6/1986 | Morrow et al. |
| 4,631,211 A | 12/1986 | Houghten |
| 4,638,045 A | 1/1987 | Kohn et al. |
| 4,790,824 A | 12/1988 | Morrow et al. |
| 4,795,436 A | 1/1989 | Robinson |
| 4,806,621 A | 2/1989 | Kohn et al. |
| 4,839,416 A | 6/1989 | Orenstein |
| 4,862,851 A | 9/1989 | Washino et al. |
| 4,886,499 A | 12/1989 | Cirelli et al. |
| 4,902,615 A | 2/1990 | Freeman et al. |
| 4,904,479 A | 2/1990 | Illum |
| 4,940,460 A | 7/1990 | Casey et al. |
| 4,941,880 A | 7/1990 | Burns |
| 4,946,929 A | 8/1990 | D'Amore et al. |
| 4,959,219 A | 9/1990 | Chow |
| RE33,405 E | 10/1990 | Chu et al. |
| 4,970,299 A | 11/1990 | Bazinet et al. |
| 4,976,968 A | 12/1990 | Steiner |
| 5,010,167 A | 4/1991 | Ron et al. |
| 5,015,235 A | 5/1991 | Crossman |
| 5,019,379 A | 5/1991 | Domb et al. |
| 5,055,404 A | 10/1991 | Ueda et al. |
| 5,064,413 A | 11/1991 | McKinnon et al. |
| 5,069,936 A | 12/1991 | Yen |
| 5,093,246 A | 3/1992 | Cech et al. |
| 5,118,528 A | 6/1992 | Fessi et al. |
| 5,141,496 A | 8/1992 | Dalto et al. |
| 5,162,504 A | 11/1992 | Horoszewicz |
| 5,175,296 A | 12/1992 | Gerster |
| 5,190,521 A | 3/1993 | Hubbard et al. |
| 5,200,181 A | 4/1993 | Soltys |
| 5,240,963 A | 8/1993 | Domb |
| 5,270,163 A | 12/1993 | Gold et al. |
| 5,312,335 A | 5/1994 | McKinnon et al. |
| 5,328,483 A | 7/1994 | Jacoby |
| 5,334,144 A | 8/1994 | Alchas et al. |
| 5,334,497 A | 8/1994 | Inaba et al. |
| 5,339,163 A | 8/1994 | Homma et al. |
| 5,342,781 A | 8/1994 | Su |
| 5,383,851 A | 1/1995 | McKinnon, Jr. et al. |
| 5,389,640 A | 2/1995 | Gerster |
| 5,399,665 A | 3/1995 | Barrera et al. |
| 5,403,750 A | 4/1995 | Braatz |
| 5,417,662 A | 5/1995 | Hjertman et al. |
| 5,449,513 A | 9/1995 | Yokoyama |
| 5,466,220 A | 11/1995 | Brenneman |
| 5,472,704 A | 12/1995 | Santus et al. |
| 5,480,381 A | 1/1996 | Weston |
| 5,500,161 A | 3/1996 | Andrianov et al. |

(Continued)

FOREIGN PATENT DOCUMENTS

| | | |
|---|---|---|
| CA | 2453959 | 1/2003 |
| CA | 2649149 | 10/2007 |

(Continued)

OTHER PUBLICATIONS

Foss et al., Clin. Cancer Res., 2005, 11: 4022-4028.*
Zhou et al., Nature Reviews Drug Discovery, 2005, 4: 1015-1026.*
Mitra et al., Journal of Controlled Release, 2001, 74: 317-323.*
Govender et al., International Journal of Pharmaceutics, 2000, 1999: 95-110.*
Avgoustakis, Curr Drug Deliv, 2004, 1: 321-333; Abstract.*
Oyewumi et al., J Control Rel, 2004, 93: 613-626.*
Hallahan et al., Cancer Cell, 2003, 3: 63-74.*
Hennenfent et al., Ann Oncol, online Dec. 2005, 17: 735.*
Bies et al., Lectin-mediated drug targeting: history and applications, *Advanced Drug Delivery Reviews*, 56:425-435 (2004).
Bocca, et al., "Phagocytic uptake of fluorescent slealth solid lipid nanoparticles", *Int. J. Pharmaceutics*, 175:185-193 (1998).

(Continued)

*Primary Examiner* — Ileana Popa
(74) *Attorney, Agent, or Firm* — Pabst Patent Group LLP

(57) ABSTRACT

The present invention provides a drug delivery system for targeted delivery of therapeutic agent-containing particles to tissues, cells, and intracellular compartments. The invention provides targeted particles comprising a particle, one or more targeting moieties, and one or more therapeutic agents to be delivered and pharmaceutical compositions comprising inventive targeted particles. The present invention provides methods of designing, manufacturing, and using inventive targeted particles and pharmaceutical compositions thereof.

43 Claims, 4 Drawing Sheets

(56) References Cited

U.S. PATENT DOCUMENTS

| | | |
|---|---|---|
| 5,503,627 A | 4/1996 | McKinnon et al. |
| 5,512,600 A | 4/1996 | Mikos et al. |
| 5,514,378 A | 5/1996 | Mikos et al. |
| 5,520,639 A | 5/1996 | Peterson et al. |
| 5,527,288 A | 6/1996 | Gross et al. |
| 5,543,158 A | 8/1996 | Gref et al. |
| 5,567,588 A | 10/1996 | Gold et al. |
| 5,569,189 A | 10/1996 | Parsons |
| 5,578,325 A | 11/1996 | Domb et al. |
| 5,595,877 A | 1/1997 | Gold et al. |
| 5,599,302 A | 2/1997 | Lilley et al. |
| 5,649,912 A | 7/1997 | Peterson |
| 5,660,985 A | 8/1997 | Pieken et al. |
| 5,686,113 A | 11/1997 | Speaker |
| 5,696,175 A | 12/1997 | Mikos et al. |
| 5,696,249 A | 12/1997 | Gold et al. |
| 5,704,911 A | 1/1998 | Parsons |
| 5,716,404 A | 2/1998 | Vacanti et al. |
| 5,733,925 A | 3/1998 | Kunz et al. |
| 5,736,372 A | 4/1998 | Vacanti et al. |
| 5,744,155 A | 4/1998 | Friedman |
| 5,763,177 A | 6/1998 | Gold et al. |
| 5,766,635 A | 6/1998 | Spenleuhauer |
| 5,770,417 A | 6/1998 | Vacanti et al. |
| 5,786,204 A | 7/1998 | He et al. |
| 5,789,163 A | 8/1998 | Drolet et al. |
| 5,804,178 A | 9/1998 | Vacanti et al. |
| 5,817,785 A | 10/1998 | Gold et al. |
| 5,820,879 A | 10/1998 | Fernandez et al. |
| 5,837,752 A | 11/1998 | Shastri et al. |
| 5,843,653 A | 12/1998 | Gold et al. |
| 5,843,732 A | 12/1998 | Davis et al. |
| 5,853,984 A | 12/1998 | Davis et al. |
| 5,869,103 A | 2/1999 | Yah et al. |
| 5,871,747 A | 2/1999 | GengouxSedlik |
| 5,874,218 A | 2/1999 | Drolet et al. |
| 5,876,727 A | 3/1999 | Swain |
| 5,879,712 A | 3/1999 | Bomberger |
| 5,893,397 A | 4/1999 | Peterson et al. |
| 5,898,031 A | 4/1999 | Crooke |
| 5,902,599 A | 5/1999 | Anseth et al. |
| 5,916,539 A | 6/1999 | Pilgrimm |
| 5,928,647 A | 7/1999 | Rock |
| 5,942,252 A | 8/1999 | Tice |
| 5,958,691 A | 9/1999 | Pieken et al. |
| 5,977,089 A | 11/1999 | Arimilli et al. |
| 5,993,412 A | 11/1999 | Deily et al. |
| 6,001,577 A | 12/1999 | Gold et al. |
| 6,005,087 A | 12/1999 | Cook et al. |
| 6,007,845 A | 12/1999 | Domb et al. |
| 6,030,613 A | 2/2000 | Blumberg |
| 6,031,086 A | 2/2000 | Switzer |
| 6,039,969 A | 3/2000 | Tomai |
| 6,043,224 A | 3/2000 | Lee |
| 6,083,505 A | 7/2000 | Miller |
| 6,095,148 A | 8/2000 | Shastri et al. |
| 6,107,094 A | 8/2000 | Crooke |
| 6,110,462 A | 8/2000 | Barbas et al. |
| 6,120,666 A | 9/2000 | Jacobson |
| 6,123,727 A | 9/2000 | Vacanti et al. |
| 6,127,533 A | 10/2000 | Cook et al. |
| 6,139,870 A | 10/2000 | Verrecchia |
| 6,184,364 B1 | 2/2001 | Pieken et al. |
| 6,190,913 B1 | 2/2001 | Singh |
| 6,197,346 B1 | 3/2001 | Mathiowitz |
| 6,225,460 B1 | 5/2001 | Bischofberger et al. |
| 6,232,082 B1 | 5/2001 | Ennifar |
| 6,235,313 B1 | 5/2001 | Mathiowitz |
| 6,238,705 B1 | 5/2001 | Liu et al. |
| 6,242,246 B1 | 6/2001 | Gold et al. |
| 6,245,776 B1 | 6/2001 | Skwierczynski |
| 6,254,890 B1 | 7/2001 | Hirosue et al. |
| 6,265,608 B1 | 7/2001 | Sumner, Jr. |
| 6,288,040 B1 | 9/2001 | Muller |
| 6,344,318 B1 | 2/2002 | Gold et al. |
| 6,348,462 B1 | 2/2002 | Gerster |
| 6,365,187 B2 | 4/2002 | Mathiowitz et al. |
| 6,376,190 B1 | 4/2002 | Gold et al. |
| 6,395,718 B1 | 5/2002 | Slusher |
| 6,399,754 B1 | 6/2002 | Cook |
| 6,403,779 B1 | 6/2002 | Kawasaki et al. |
| 6,429,200 B1 | 8/2002 | Monahan et al. |
| 6,444,782 B1 | 9/2002 | Hamlin |
| 6,451,527 B1 | 9/2002 | Larocca et al. |
| 6,458,539 B1 | 10/2002 | Gold et al. |
| 6,458,543 B1 | 10/2002 | Gold et al. |
| 6,482,594 B2 | 11/2002 | Gold et al. |
| 6,492,554 B2 | 12/2002 | Dalton et al. |
| 6,506,559 B1 | 1/2003 | Fire et al. |
| 6,506,577 B1 | 1/2003 | Deming et al. |
| 6,528,499 B1 | 3/2003 | Kozikowski |
| 6,558,951 B1 | 5/2003 | Tomai |
| 6,569,896 B2 | 5/2003 | Dalton et al. |
| 6,589,562 B1 | 7/2003 | Shefer et al. |
| 6,589,563 B2 | 7/2003 | Prokop |
| 6,608,201 B2 | 8/2003 | Gerster |
| 6,610,319 B2 | 8/2003 | Tomai |
| 6,610,713 B2 | 8/2003 | Tracey |
| 6,632,922 B1 | 10/2003 | Deming et al. |
| 6,686,446 B2 | 2/2004 | Deming |
| 6,686,472 B2 | 2/2004 | Gerster |
| 6,696,076 B2 | 2/2004 | Tomai |
| 6,699,474 B1 | 3/2004 | Cerny |
| 6,716,583 B2 | 4/2004 | Gold et al. |
| 6,723,429 B2 | 4/2004 | Bengs |
| 6,737,056 B1 | 5/2004 | Presta |
| 6,747,156 B2 | 6/2004 | Johansson |
| 6,767,702 B2 | 7/2004 | Mirkin |
| 6,818,732 B2 | 11/2004 | Deming et al. |
| 6,838,484 B2 | 1/2005 | Steiner et al. |
| 6,875,605 B1 | 4/2005 | Ma |
| 6,875,886 B2 | 4/2005 | Frangioni |
| 6,902,743 B1 | 6/2005 | Setterstrom |
| 6,932,971 B2 | 8/2005 | Bachmann et al. |
| 6,984,393 B2 | 1/2006 | Amsiden |
| 6,995,284 B2 | 2/2006 | Dalton et al. |
| 6,998,500 B2 | 2/2006 | Dalton et al. |
| 7,008,411 B1 | 3/2006 | Mandrusov et al. |
| 7,022,870 B2 | 4/2006 | Dalton et al. |
| 7,026,500 B2 | 4/2006 | Dalton et al. |
| 7,029,859 B2 | 4/2006 | Thompson |
| 7,030,228 B1 | 4/2006 | Schmitz |
| 7,056,704 B2 | 6/2006 | Tuschl et al. |
| 7,078,196 B2 | 7/2006 | Tuschl et al. |
| 7,097,837 B2 | 8/2006 | Nielsen |
| 7,149,574 B2 | 12/2006 | Yun |
| 7,163,680 B2 | 1/2007 | Bander |
| 7,247,502 B2 | 7/2007 | Ennifar |
| 7,250,499 B2 | 7/2007 | Mirkin |
| 7,335,744 B2 | 2/2008 | Liu |
| 7,363,076 B2 | 4/2008 | Yun |
| 7,375,180 B2 | 5/2008 | Gorden |
| 7,387,271 B2 | 6/2008 | Noelle |
| 7,422,902 B1 | 9/2008 | Wheeler et al. |
| 7,427,629 B2 | 9/2008 | Kedl |
| 7,488,792 B2 | 2/2009 | Ruoslahti |
| 7,550,441 B2 | 6/2009 | Farokhzad et al. |
| 7,727,969 B2 | 6/2010 | Farokhzad |
| 7,762,803 B2 | 7/2010 | Nakazato |
| 7,767,803 B2 | 8/2010 | Diener |
| 2001/0012890 A1 | 8/2001 | Thompson |
| 2002/0009466 A1 | 1/2002 | Brayden |
| 2002/0064780 A1 | 5/2002 | Gold et al. |
| 2002/0068091 A1 | 6/2002 | Davis et al. |
| 2002/0086356 A1 | 7/2002 | Tuschl et al. |
| 2002/0099036 A1 | 7/2002 | Dalton et al. |
| 2002/0099096 A1 | 7/2002 | Dalton et al. |
| 2002/0102613 A1 | 8/2002 | Hoogenboom |
| 2002/0106647 A1 | 8/2002 | Segal |
| 2002/0116054 A1 | 8/2002 | Lundell |
| 2002/0119916 A1 | 8/2002 | Hassan |
| 2002/0150578 A1 | 10/2002 | He et al. |
| 2002/0151004 A1 | 10/2002 | Craig |
| 2002/0153251 A1 | 10/2002 | Sassi et al. |

(56) References Cited

U.S. PATENT DOCUMENTS

| | | |
|---|---|---|
| 2002/0156125 A1 | 10/2002 | Broder et al. |
| 2002/0173495 A1 | 11/2002 | Dalton et al. |
| 2003/0003103 A1 | 1/2003 | Thompson |
| 2003/0009029 A1 | 1/2003 | Buchholz et al. |
| 2003/0022868 A1 | 1/2003 | Dalton et al. |
| 2003/0035804 A1 | 2/2003 | D'Amico et al. |
| 2003/0054360 A1 | 3/2003 | Gold et al. |
| 2003/0087301 A1 | 5/2003 | Smith et al. |
| 2003/0099668 A1 | 5/2003 | Bachmann |
| 2003/0108611 A1 | 6/2003 | Bosch et al. |
| 2003/0108923 A1 | 6/2003 | Tuschl et al. |
| 2003/0133988 A1 | 7/2003 | Fearon |
| 2003/0134810 A1 | 7/2003 | Springate et al. |
| 2003/0138557 A1 | 7/2003 | Allison |
| 2003/0143184 A1 | 7/2003 | Seo |
| 2003/0162761 A1 | 8/2003 | Steiner et al. |
| 2003/0165478 A1 | 9/2003 | Sokoll |
| 2003/0175950 A1 | 9/2003 | McSwiggen |
| 2003/0219766 A1 | 11/2003 | Raitano et al. |
| 2003/0225040 A1 | 12/2003 | Dalton et al. |
| 2003/0232013 A1 | 12/2003 | Sieckman et al. |
| 2003/0232792 A1 | 12/2003 | Dalton et al. |
| 2003/0235619 A1 | 12/2003 | Allen |
| 2004/0014975 A1 | 1/2004 | Dalton et al. |
| 2004/0022727 A1 | 2/2004 | Stanton |
| 2004/0022840 A1 | 2/2004 | Nagy et al. |
| 2004/0029913 A1 | 2/2004 | Dalton et al. |
| 2004/0043923 A1 | 3/2004 | Parma et al. |
| 2004/0052727 A1 | 3/2004 | Dalton et al. |
| 2004/0054190 A1 | 3/2004 | Pomper |
| 2004/0059094 A1 | 3/2004 | Bachmann et al. |
| 2004/0067196 A1 | 4/2004 | Brunke et al. |
| 2004/0067503 A1 | 4/2004 | Tan et al. |
| 2004/0067979 A1 | 4/2004 | Dalton et al. |
| 2004/0072234 A1 | 4/2004 | Parma et al. |
| 2004/0086544 A1 | 5/2004 | Bezemer |
| 2004/0087810 A1 | 5/2004 | Dalton et al. |
| 2004/0092470 A1 | 5/2004 | Leonard et al. |
| 2004/0136961 A1 | 7/2004 | Prokop et al. |
| 2004/0141958 A1 | 7/2004 | Steinaa |
| 2004/0147489 A1 | 7/2004 | Dalton |
| 2004/0147550 A1 | 7/2004 | Dalton et al. |
| 2004/0156846 A1 | 8/2004 | Daum et al. |
| 2004/0167103 A1 | 8/2004 | Dalton et al. |
| 2004/0192626 A1 | 9/2004 | McSwiggen et al. |
| 2004/0241790 A1 | 12/2004 | Eriksen et al. |
| 2004/0247680 A1 | 12/2004 | Farokhzad |
| 2004/0248088 A1 | 12/2004 | Raitano et al. |
| 2004/0260092 A1 | 12/2004 | Miller et al. |
| 2004/0260108 A1 | 12/2004 | Dalton et al. |
| 2004/0266688 A1 | 12/2004 | Nayak |
| 2005/0017667 A1 | 1/2005 | Yamamoto |
| 2005/0019870 A1 | 1/2005 | Afar et al. |
| 2005/0019872 A1 | 1/2005 | Afar et al. |
| 2005/0020525 A1 | 1/2005 | McSwiggen et al. |
| 2005/0032733 A1 | 2/2005 | McSwiggen et al. |
| 2005/0033074 A1 | 2/2005 | Dalton et al. |
| 2005/0037075 A1 | 2/2005 | Farokhzad et al. |
| 2005/0048063 A1 | 3/2005 | Ruoslahti |
| 2005/0048121 A1 | 3/2005 | East et al. |
| 2005/0069910 A1 | 3/2005 | Turner |
| 2005/0079152 A1 | 4/2005 | Bot |
| 2005/0079553 A1 | 4/2005 | Ayyoub |
| 2005/0080128 A1 | 4/2005 | Tsukamoto et al. |
| 2005/0100877 A1 | 5/2005 | Xu et al. |
| 2005/0107322 A1 | 5/2005 | OHagan |
| 2005/0122550 A1 | 6/2005 | Plewa et al. |
| 2005/0136258 A1 | 6/2005 | Nie |
| 2005/0158390 A1 | 7/2005 | Rana et al. |
| 2005/0191294 A1 | 9/2005 | Arap et al. |
| 2005/0207940 A1 | 9/2005 | Butler |
| 2005/0214378 A1 | 9/2005 | Hoarau |
| 2005/0233948 A1 | 10/2005 | D'Amico et al. |
| 2005/0244863 A1 | 11/2005 | Mir |
| 2005/0249799 A1 | 11/2005 | Jacob et al. |
| 2005/0256071 A1 | 11/2005 | Davis |
| 2005/0260186 A1 | 11/2005 | Bookbinder et al. |
| 2006/0002852 A1 | 1/2006 | Saltzman et al. |
| 2006/0002971 A1 | 1/2006 | Saltzman |
| 2006/0004042 A1 | 1/2006 | Dalton et al. |
| 2006/0009529 A1 | 1/2006 | Dalton et al. |
| 2006/0035966 A1 | 2/2006 | Dalton et al. |
| 2006/0057219 A1 | 3/2006 | Nagasaki |
| 2006/0062787 A1 | 3/2006 | Hitraya |
| 2006/0083711 A1 | 4/2006 | Berry et al. |
| 2006/0110460 A1 | 5/2006 | Ferret |
| 2006/0111271 A1 | 5/2006 | Cerny |
| 2006/0165987 A1 | 7/2006 | Hildgen |
| 2006/0173170 A1 | 8/2006 | Chamberlian et al. |
| 2006/0183931 A1 | 8/2006 | Dalton et al. |
| 2006/0228371 A1 | 10/2006 | Raso |
| 2006/0239907 A1 | 10/2006 | Luzzi et al. |
| 2006/0240093 A1 | 10/2006 | Maclachlan et al. |
| 2006/0241180 A1 | 10/2006 | Dalton et al. |
| 2006/0258628 A1 | 11/2006 | Steiner et al. |
| 2006/0269557 A1 | 11/2006 | Sherman et al. |
| 2006/0276540 A1 | 12/2006 | Dalton et al. |
| 2006/0287547 A1 | 12/2006 | Dalton et al. |
| 2007/0014807 A1 | 1/2007 | Maida |
| 2007/0041901 A1 | 2/2007 | Diener |
| 2007/0043066 A1 | 2/2007 | Sum |
| 2007/0053845 A1 | 3/2007 | Sengupta |
| 2007/0116768 A1 | 5/2007 | Chorny |
| 2007/0184068 A1 | 8/2007 | Renner |
| 2007/0224225 A1 | 9/2007 | IracheGarreta |
| 2007/0225213 A1 | 9/2007 | Kosak |
| 2008/0026000 A1 | 1/2008 | Ennifar |
| 2008/0031899 A1 | 2/2008 | Reddy |
| 2008/0057102 A1 | 3/2008 | Roorda |
| 2008/0081074 A1 | 4/2008 | Gu |
| 2008/0124400 A1 | 5/2008 | Liggins |
| 2008/0171059 A1 | 7/2008 | Howland |
| 2008/0193381 A1 | 8/2008 | Babich |
| 2008/0213377 A1 | 9/2008 | Bhatia |
| 2008/0268063 A1 | 10/2008 | Jon |
| 2009/0004118 A1 | 1/2009 | Nie |
| 2009/0028910 A1 | 1/2009 | DeSimone et al. |
| 2009/0061010 A1 | 3/2009 | Zale |
| 2009/0074828 A1 | 3/2009 | Alexis |
| 2009/0117549 A1 | 5/2009 | Tan |
| 2009/0192100 A1 | 7/2009 | Vater |
| 2009/0298710 A1 | 12/2009 | Farokhzad et al. |
| 2010/0022680 A1 | 1/2010 | Karnik et al. |
| 2010/0068285 A1 | 3/2010 | Zale |
| 2010/0068286 A1 | 3/2010 | Troiano |
| 2010/0069426 A1 | 3/2010 | Zale |
| 2010/0092425 A1 | 4/2010 | Von Andrian et al. |
| 2010/0104655 A1 | 4/2010 | Zale |
| 2010/0129392 A1 | 5/2010 | Shi et al. |
| 2010/0129439 A1 | 5/2010 | Alexis et al. |
| 2010/0144845 A1 | 6/2010 | Farokhzad et al. |
| 2010/0183727 A1 | 7/2010 | Iannacone et al. |
| 2010/0196482 A1 | 8/2010 | Radovic-Moreno et al. |
| 2010/0203142 A1 | 8/2010 | Zhang et al. |
| 2010/0216804 A1 | 8/2010 | Zale |
| 2010/0226986 A1 | 9/2010 | Grayson |
| 2010/0233251 A1 | 9/2010 | Von Andrian et al. |
| 2010/0266491 A1 | 10/2010 | Farokhzad |
| 2010/0297233 A1 | 11/2010 | Moretti |
| 2010/0303723 A1 | 12/2010 | Farokhzad |
| 2011/0052697 A1 | 3/2011 | Farokhzad |

FOREIGN PATENT DOCUMENTS

| | | |
|---|---|---|
| DK | 0418187 | 3/1991 |
| EP | 0333523 | 9/1989 |
| EP | 1279404 | 1/2003 |
| EP | 1752141 | 2/2007 |
| EP | 1872793 | 1/2008 |
| EP | 1932538 | 6/2008 |
| EP | 2106806 | 10/2009 |
| KR | 0418916 | 3/2002 |
| KR | 0041712 | 6/2004 |
| WO | WO 88/04300 | 6/1988 |

(56) References Cited

FOREIGN PATENT DOCUMENTS

| | | |
|---|---|---|
| WO | WO 90/11364 | 3/1990 |
| WO | 9006430 | 6/1990 |
| WO | 9006433 | 6/1990 |
| WO | 9106286 | 5/1991 |
| WO | 9106287 | 5/1991 |
| WO | 9503357 | 2/1995 |
| WO | WO 97/04747 | 2/1997 |
| WO | WO 97/13537 | 4/1997 |
| WO | WO 97/37705 | 10/1997 |
| WO | WO 98/08856 | 3/1998 |
| WO | 98/51325 | 11/1998 |
| WO | 99/01498 | 1/1999 |
| WO | WO 99/34850 | 7/1999 |
| WO | WO 00/21572 | 4/2000 |
| WO | WO 00/27363 | 5/2000 |
| WO | 0032239 | 6/2000 |
| WO | WO 00/44895 | 8/2000 |
| WO | WO 01/75164 | 10/2001 |
| WO | 0218477 | 3/2002 |
| WO | WO 02/18477 | 3/2002 |
| WO | WO 02/076469 | 10/2002 |
| WO | WO 02/076603 | 10/2002 |
| WO | WO 02/100442 | 12/2002 |
| WO | WO 03/000777 | 1/2003 |
| WO | WO 03/004654 | 1/2003 |
| WO | 03033592 | 4/2003 |
| WO | WO 03/028657 | 4/2003 |
| WO | WO 03/030941 | 4/2003 |
| WO | WO 03/051304 | 6/2003 |
| WO | 03074679 | 9/2003 |
| WO | WO 03/072637 | 9/2003 |
| WO | WO 03/102708 | 12/2003 |
| WO | 2004030608 | 4/2004 |
| WO | WO 2004/030608 | 4/2004 |
| WO | WO 2004/071493 | 8/2004 |
| WO | 2004096140 | 11/2004 |
| WO | WO 2004/096998 | 11/2004 |
| WO | 2004105782 | 12/2004 |
| WO | WO 2005/012407 | 2/2005 |
| WO | WO 2005/028539 | 3/2005 |
| WO | 2005046572 | 5/2005 |
| WO | WO 2005/042573 | 5/2005 |
| WO | WO 2005/072710 | 8/2005 |
| WO | 2005105056 | 11/2005 |
| WO | WO 2005/111192 | 11/2005 |
| WO | 2005112885 | 12/2005 |
| WO | 2005112886 | 12/2005 |
| WO | WO 2005/121181 | 12/2005 |
| WO | 2006025627 | 3/2006 |
| WO | 2006037979 | 4/2006 |
| WO | WO 2006/037979 | 4/2006 |
| WO | WO 2006/042146 | 4/2006 |
| WO | WO 2006/066158 | 6/2006 |
| WO | WO 2006/078278 | 7/2006 |
| WO | WO 2006/090924 | 8/2006 |
| WO | 2006093991 | 9/2006 |
| WO | 2006099445 | 9/2006 |
| WO | WO 2006/096754 | 9/2006 |
| WO | WO 2006/133271 | 12/2006 |
| WO | WO 2006/138463 | 12/2006 |
| WO | 2007001448 A2 | 1/2007 |
| WO | WO 2007/021142 | 2/2007 |
| WO | 2007024026 | 3/2007 |
| WO | 2007034479 | 3/2007 |
| WO | WO 2007/070682 | 6/2007 |
| WO | WO 2007/076371 | 7/2007 |
| WO | WO 2007/084797 | 7/2007 |
| WO | 2007098254 | 8/2007 |
| WO | WO 2007/109364 | 9/2007 |
| WO | WO 2007/118653 | 10/2007 |
| WO | 2007133807 | 11/2007 |
| WO | 2007137117 | 11/2007 |
| WO | 2007144807 A2 | 12/2007 |
| WO | WO 2007/150030 | 12/2007 |
| WO | 2008019142 | 2/2008 |
| WO | 2008041703 | 4/2008 |
| WO | 2008058192 | 5/2008 |
| WO | WO 2008/051291 | 5/2008 |
| WO | 2008105772 | 9/2008 |
| WO | 2008105773 | 9/2008 |
| WO | 2008121949 | 10/2008 |
| WO | 2008124632 | 10/2008 |
| WO | 2008124634 | 10/2008 |
| WO | 2008124639 | 10/2008 |
| WO | 2008147456 | 12/2008 |
| WO | WO 2009/051837 | 4/2009 |
| WO | WO 2009/109428 | 9/2009 |
| WO | 2010005721 | 1/2010 |
| WO | 2010005723 | 1/2010 |
| WO | 2010005725 | 1/2010 |
| WO | 2010005726 | 1/2010 |
| WO | 2010068866 | 6/2010 |
| WO | 2010075072 | 7/2010 |
| WO | 2010114768 | 10/2010 |
| WO | 2010114770 | 10/2010 |
| WO | 2011072218 | 6/2011 |

OTHER PUBLICATIONS

Brooking et al., "Transport of Nanoparticles Across the Rat Nasal Mucosa", *Journal of Drug Targeting*, 9(4):267-279 (2001).

Chandy et al., "Development of Poly(Lactic Acid)/Chitosan Co-Matrix Microspheres: Controlled Release of Taxol-Heparin for Preventing Restenosis", *Drug Delivery*, 8:77-86 (2001).

Chandy, et al., "5-Fluorouracil-loaded chitosan coated polylactic acid pmicrospheres as biodegradable drug carriers for cerebral tumors", *J. Microencapsulation*, 17(5):625-638 (2000).

Cheng, et al., "Formulation of functionalized PLGA-PEG nanoparticles for in vivo targeted drug delivery", *Biomaterials*, 28:869-875 (2007).

Coppi, et al., "Chitosan-Alginate Microparticles as a Protein Carrier", *Drug Development and Industrial Pharmacy*, 27(5):393-400 (2001).

Elvassore, et al., "Production iof Insulin-Loaded Poly(Ethylene Glycol)/Poly(/-Lactide) (PEG/PLA) Nanoparticles by Gas Antisolvent Techniques", *Journal of Pharmacrutical Sciences*, 90(10):1628-36 (2001).

Ermak and Giannasca, "Microparticle targeting to M cells", *Advanced Drug Delivery Reviews*, 34:261-283 (1998).

Fi Li Povic-Grcic et al., "Mucoadhesive chitosan-coated liposomes: characteristics and stability", *J. Microencapsulation*, 18 1:3-12 (2001).

Gaserod et al., "The enhancement of the bioadhesive properties of calcium alginate gel beads by coating with chitosan", *Intl. J. of Pharmaceutics*, 175:237-246 (1998).

Hejazi et al., "Stomach-specific anti-H. pylon therapy. I: preparation and characterization of tetracyline-loaded chitosan microshpheres", *Intl. J. of Pharmaceutics*, 235:87-94 (2002).

Huang et al., "Microencapsulation of Chlorpheniramine Maleate-Resin Particles with Crosslinked Chitosan for Sustained Release", *Pharmaceutical Development and Technology*, 4 1:107-115 (1999).

Janes et al., "Chitosan nanoparticles as delivery systems for doxorubicin", *Journal of Controlled Release*, 73:255-267 (2001).

Jayasena, "Aptamers: An Emerging Class of Molecules That Rival Antibodies in Diagnostics", *Clinical Chemistry*, 45(9):1628-1650 (1999).

Kawashima, et al., "Mucoadhesive DL-Lactide/Glycolide Copolymer Nanoshperes Coated with Chitosan to Improve Oral Delivery of Elcatonin", *Pharmaceutical Development and Technology*, 5(1):77-85 (2000).

Khandare, et al., "Polymer-drug conjugates: Progress in polymeric prodrugs," *Progress in Polymer Science*, 31(4):359-397 (2006).

Kim, et al., "Target-specific cellular uptake of PLGA nanoparticles coated with poly(L-lysine)-poly(ethyleneglycol)-folate conjugate", *Langmuir*, 21(19):8852-8857 (2005).

Lehr, "Lectin-mediated drug delivery: The second generation of bioadhesives", *J. of Controlled Release*, 65:19-29 (2000).

Lim et al., "Preparation and evaluation of the in vitro drug release properties and mucoadhesion of novel microspheres of hyaluronic acid and chitosan", *J. of Controlled Release*, 66:281-292 (2000).

(56) References Cited

OTHER PUBLICATIONS

Mi, et al., "Release of Indomethacin from a Novel Chitosan Microsphere Prepared by a Natrually Occurring Crosslinker: Examination of Crosslinking and Polycation-Anionic Drug Interaction", *J. of Applied Polymer Science*, 81:1700-1711 (2001).
Olivier, et al., "Drug Transport to Brain with Targeted Nanoparticles", *J. of the Am. Society of Experimental Neuro Therapeutics*, 2:108-119 (2005).
Pimentel, et al., "Peptide nanoparticles as novel immunogens: design and analysis of a prototypic severe acute respiratory syndrome vaccine", *Chemical Biology & Drug Design*, 73(1):53-61 (2009).
Ponchel, et al., "Specific and non-specific bioadhesive particulate systems for oral delivery to the gastrointestinal tract", *Advanced Drug Delivery Reviews*, 34:191-219 (1998).
Shimoda, et al., "Bioadhesive Characteristics of Chitosan Mircroshperes to the Mucosa of Rat Small Intestine", *Drug Delvelopment and Inustrial Pharmacy*, 27(6):567-576 (2001).
Simberg, et al., "Biomimetic amplification of nanoparticle homing to tumors", *Nat'l. Acad. Sic. USA*, 104(3):921-936 (2007).
Takeuchi, et al., "Enteral Absorption of Insulin in Rats from Mucoadhesive Chitosan-Coated Liposomes", *Pharmaceutical Research*, 13(6):896-901 (1996).
Takeuchi et al., "Mucoashesive Lipsomes Coated with Chitosan or Carbopol for Oral Administration of Peptide Drugs", *Proceed. Intl. Symp. Control. Rel. Bioact. Mater.*, 26:988-989 (1999).
Takeuchi, et al., "Spray-Dried Lactose Composite Particles Containing an Ion Complex of Alginate-Chitosan for Desinging a Dry-Coated Tablet Having a Time-Controlled Releasing Function", *Pharmaceutical Research*, 17 (1):94-99 (2000).
Tavitian, et al., "In vivo imaging with oligonucleotides for diagnosis and drug development", *Gut, 52 Su*, I IV :40-47 (2003).
Tobio, et al "Role of PEG on the stability in digestive fluids and in vivo fate of PEG-PLA nanoparticles following oral administration", *Colloids and Surfaces B: Biointerferences*, 18:315-323 (2000).
Vila, et al., "Design of biodegradable particles for protein delivery", *Journal of Controlled Release*, 78:15-24 (2002).
Vila, et al., "PLA-PEG Nanospheres: New Carriers for Transmucosal Delivery of Proteins and Plasmid DNA", *Poly. Adv. Technol.*, 13:851-858 (2002).
Yamada, et al., "In Vitro and in Vivo Evaluation of Sustained Release Chitosan-Coat Ketoprofen Microparticles", *Yakugaku Zasshi*, 121(3):239-245 (2001).
Yourong, et al, "Preparation of DHAQ-loaded mPEG-PLGA-mPEG nanoparticles and evaluation of drug release behaviors in vitro/in vivo," *J. Mat. Sci.: Mat. Med.*, 17(6): 509-16 (2006).
Yuan, et al., "Intranasal immunization with chitosan/pCETP nanoparticles inhibits atherosclerosis in a rabbit model of atherosclerosis", *Vaccine, Bitterworth Scientific*, 26:29-30 (2008).
Heald, et al., "Poly(lactic acid)-poly(ethylene oxide) (PLA-PEG) nanoparticles: NMR studies of the central solidlike PLA core and the liquid PEG corona", *Langmuir*, 18:3669-3675 (2002).
Tomai, et al., "Resiquimod and other immune response modifiers as vaccine adjuvants", Expert Rev Vaccines, 6:835-847 (2007) Abstract Only.
Villa, et al., "PLA-PEG particles as nasal protein carriers: the influence of the particle size", *Int. J Pharmaceut.*, 292:43-52 (2005).
Sarkar, et al., "Ligand-DNA interaction in a nanocage of reverse micelle", Biopolymer., 83(6):675-86 (2006).
International Search Report mailed Sep. 5, 2008.
U.S. Appl. No. 12/301,225, Farokhzad, et al., filed Nov. 17, 2008.
U.S. Appl. No. 12/515,465, Farokhzad, et al., filed May 5, 2010.
U.S. Appl. No. 12/526,300, Moretti, et al., filed Aug. 11, 2010.
Abad, et al., "Comparison of a Monoclonal Antibody-Based Enzyme-Linked Immunosorbent Assay and Gas Chromatography for the Determination of Nicotine in Cigarette Smoke Condensates", *Anal. Chem.*, 65:3227-3231 (1993).
Ackermand & Cresswell, "Cellular mechanisms governing cross-presentation of exogenous antigens", *Nat. Immunol.*, 5(7):678-684 (2004).

Aime, et al., "Lanthanide(III) chelates for NMR biomedical applications", *Chemical Society Reviews*, 27:19-29 (1998).
Akaishi, et al., "Targeting Chemotherapy Using Antibody-Combined Liposome against Human Pancreatic Cancer Cell-Line", *Tohoku J. Exp. Med.*, 175(1):29-42 (1995).
Allen, et al., "Nano-engineering block copolymer aggregates for drug delivery.", *Colloids Surfaces B-Biointerfaces*, 16:3-27 (1999).
Allison, et al., "The mode of action of immunological adjuvants.", *Dev. Biol. Stand.*, 92:3-11 (1998).
Altschul, et al., "Basic local alignment search tool.", *J. Mol Biol.*, 215(3):403-10 (1990).
Altschul, et al., "Gapped BLAST and PSI-BLAST: a new generation of protein database search programs.", *Nucleic Acids Res.*, 25(17):3389-3402 (1997).
Angelucci, et al., "Neuroendocrine transdifferentiation induced by VPA is mediated by PPARγ activation and confers resistance to antiblastic therapy in prostate carcinoma", *The Prostate*, 68(6):588-598 (2008).
Astete and Sabliov, "Synthesis and characterization of PLGA nanoparticles", *J. Biomat. Sci.,-Polymer Ed.*, 17:247-289 (2006).
Atkinson, et al., "Conjugation of folate via gelonin carbohydrate residues retains ribosomal-inactivating properties of the toxin and permits targeting to folate receptor positive cells.", *J. Biol. Chem.*, 276(30):27930-27935 (2001).
Baba, et al., "Human neutralizing monoclonal antibodies of the IgG1 subtype protect against mucosal simian-human immunodeficiency virus infection.", *Nat. Med.*, 6(2):200-206 (2000).
Babaian, et al., "Radioimmunological imaging of metastatic prostatic cancer with 111indium-labeled monoclonal antibody PAY 276.", *J. Urol.*, 137(3):439-443 (1987).
Bachmann, et al., "T helper cell-independent neutralizing B cell response against vesicular stomatitis virus: role of antigen patterns in B cell induction?", *Eur. J. Immunol.*, 25(12):3445-3451 (1995).
Bagalkot, et al., "An Aptamer-Doxorubicin Physical Conjugate as a Novel Targeted Drug-Delivery Platform", *Angew. Chem. Int. Ed.*, 45(48):8149-8152 (2006).
Bander, et al., "Targeting metastatic prostate cancer with radiolabeled monoclonal antibody J591 to the extracellular domain of prostate specific membrane antigen.", *J. Urol.*, 170(5):1717-1721 (2003).
Barchet, et al., "Virus-induced interferon alpha production by a dendritic cell subset in the absence of feedback signaling in vivo.", *J. Exp. Med.*, 195(4):507-516 (2002).
Barrera, et al., "Synthesis and RGD peptide modification of a new biodegradable copolymer: poly(lactic acid-co-lysine)", *J. Am. Chem. Soc.*, 115(23):11010-11011 (1993).
Bauer, et al., "SMS 201-995: a very potent and selective octapeptide analogue of somatostatin with prolonged action.", *Life Sci.*, 31(11):1133-1140 (1982).
Beaureparie, et al., "Functionalized Fluorescent Oxide Nanoparticles: Artificial Toxins for Sodium Channel Targeting and Imaging at the Single-Molecule Level", *Nano Letters*, 4(11):2079-2083 (2004).
Bennett, et al., "Inhibition of the Aminopeptidase from Aeromonas Proteolytica by I-Leucinephosphonic Acid, a Transition State Analogue of Peptide Hydrolysis", *J. Am. Chem. Soc.*, 120(46):12139-12140 (1998).
Binetruy-Tournaire, et al., "Identification of a peptide blocking vascular endothelial growth factor (VEGF)-mediated angiogenesis.", *EMBO J.*, 19(7):1525-1533 (2000).
Bjerke, et al., "Comparison of monoclonal and polyclonal antibodies to continine in nonisotopic and isotopic immunoassays", *J. Immunol. Meth.*, 96:239-246 (1987).
Boes, et al., "T-cell engagement of dendritic cells rapidly rearranges MHC class II transport.", *Nature*, 418(6901):983-988 (2002).
Bonifaz, et al., "Efficient targeting of protein antigen to the dendritic cell receptor DEC-205 in the steady state leads to antigen presentation on major histocompatibility complex class I products and peripheral CD8+ T cell tolerance.", *J. Exp. Med.*, 196(12):1627-1638 (2002).
Bottausci, et al., "Mixing in the shear superposition micromixer: three-dimensional analysis", *Philosophical Transactions of the*

(56) References Cited

OTHER PUBLICATIONS

*Royal Society of London Series a-Mathematical Physical and Engineering Sciences*, 362:1001-1018 (2004).
Boussif, et al., "A versatile vector for gene and oligonucleotide transfer into cells in culture and in vivo: polyethylenimine.", *Proc. Natl. Acad. Sci., USA*, 1995, 92:7297-7301 (1995).
Bozzacco, et al., "DEC-205 receptor on dendritic cells mediates presentation of HIV gag protein to CD8+ T cells in a spectrum of human MHC I haplotypes.", *Proc. Natl. Acad. Sci., USA*, 104(4):1289-1294 (2007).
Brito, et al., "Nanoparticulate carriers for the treatment of coronary restenosis.", *Int J Nanomedicine*, 2(2):143-161 (2007).
Burmeister, et al., "Direct in vitro selection of a 2'-O-methyl aptamer to VEGF.", *Chem Biol*, 12(1):25-33 (2005).
Carino, et al., "Nanosphere based oral insulin delivery," *J. Control. Release*, 65(1-2):261-9 (2000).
Casola, et al., "B cell receptor signal strength determines B cell fate.", *Nat. Immunol.*, 5(3):317-327 (2004).
Castro & Prieto, "Nicotine Antibody Production: Comparison of two nicotine conjugates in different animal species", *Biochem. Biophys. Res. Comm.*, 67(2):583-589 (1975).
Castro, et al., "Nicotine Antibodies: Comparison of Ligand Specificities of Antibodies Produced against Two Nicotine Conjugates", *Eur. J. Biochem.*, 104:331-340 (1980).
Chacon, et al., "Optimized preparation of poly D,L (lactic-glycolic) microspheres and nanoparticles for oral administration", *Int'l J. Pharmaceutics*, 141:81-91 (1996).
Chaires, et al., "Preferential binding of daunomycin to 5'ATCG and 5'ATGC sequences revealed by footprinting titration experiments.", *Biochemistry*, 29(26):6145-6153 (1990).
Chang, et al., "Five Different Anti-Prostate-specific Membrane Antigen (PSMA) Antibodies Confirm PSMA Expression in Tumor-associated Neovasculature", *Cancer Res.*, 59:3192-3198 (1999).
Cheng, et al., "Formulation of functionalized PLGA-PEG nanoparticles for in vivo targeted drug delivery.", *Biomaterials*, 28(5):869-876 (2007).
Christian, et al., "Nucleolin expressed at the cell surface is a marker of endothelial cells in angiogenic blood vessels.", *J. Cell Biol.*, 163(4):871-878 (2003).
Chu, et al., "Aptamer mediated siRNA delivery", *Nuc. Acid Res.*, 34:e73 (2006).
Chu, et al., "Labeling tumor cells with fluorescent nanocrystal-aptamer bioconjugates.", *Biosens. Bioelectron.*, 21:1859-1866 (2006).
Clark, "The reticulum of lymph nodes in mice studied with the electron microscope.", *Am. J. Anat.*, 110:217-257 (1962).
Connor, et al., "Ex vivo evaluation of anti-EpCAM immunocytokine huKS-IL2 in ovarian cancer.", *J. Immunother.*, 27(3):211-219 (2004).
Croy and Kwon, "Polymeric micelles for drug delivery", *Curr. Pharm. Design*, 12:4669-4684 (2006).
D'Antonio, et al., "Longitudinal analysis of androgen deprivation of prostate cancer cells identifies pathways to androgen independence", *The Prostate*, 68(7):698-714 (2008).
Dang and Rock, "Stimulation of B lymphocytes through surface Ig receptors induces LFA-1 and ICAM-1-dependent adhesion.", *J. Immunol.*, 146(10):3273-3279 (1991).
De Graaf, et al., "A fully human anti-Ep-CAM scFv-beta-glucuronidase fusion protein for selective chemotherapy with a glucuronide prodrug.", *Br. J. Cancer*, 86(5):811-818 (2002).
De Jaeghere, et al., "Freeze-drying and lyopreservation of diblock and triblock poly(lactic acid)-poly(ethylene oxide) (PLA-PEO) copolymer nanoparticles.", *Pharm. Dev. Technol.*, 5(4):473-483 (2000).
Delemarre, et al., "Repopulation of macrophages in popliteal lymph nodes of mice after liposome-mediated depletion.", *J. Leukoc. Biol.*, 47(3):251-257 (1990).
Demello and Demello, "Microscale reactors: nanoscale products.", *Lab on a Chip*, 4(2):11N-15N (2004).
Demello, "Control and detection of chemical reactions in microfluidic systems.", *Nature*, 442(7101):394-402 (2006).
Deming, et al., "Facile synthesis of block copolypeptides of defined architecture.", *Nature*, 390(6658):386-389 (1997).
Derfus, et al., "Intracellular Delivery of Quantum Dots for Live Cell Labeling and Organelle Tracking", *Advanced Materials*, 16:961-966 (2004).
Dimarco and Arcamone, "DNA complexing antibiotics: Daunomycin, adriamycin and their derivates.", *Arzneim-Forsch. (Drug Res.)*, 25:368-375 (1975).
Ding, et al., "Syntheses of conformationally constricted molecules as potential NAALADase/PSMA inhibitors.", *Org. Lett.*, 6(11):1805-1808 (2004).
Dinkla, et al., "Identification of a streptococcal octapeptide motif involved in acute rheumatic fever.",*J. Biol. Chem.*, 282(26):18686-18693 (2007).
Dykxhoorn, et al., "Killing the messenger: short RNAs that silence gene expression.", *Nat. Rev. Mol. Cell Biol.*, 4(6):457-467 (2003).
Eklund, et al., "Denileukin diftitox: a concise clinical review.", *Expert Rev. Anticancer Ther.*, 5(1):33-38 (2005).
Elbashir, et al., "RNA interference is mediated by 21- and 22-nucleotide RNAs.", *Genes Dev.*, 15(2):188-200 (2001).
Eldridge, et al., "Biodegradable microspheres as a vaccine delivery system," *Mol. Immunol.*, 28(3):287-94 (1991).
Elsässer-Beile, et al., "A new generation of monoclonal and recombinant antibodies against cell-adherent prostate specific membrane antigen for diagnostic and therapeutic targeting of prostate cancer.", *Prostate*, 66(13):1359-1370 (2006).
Farokhzad, et al., "Nanoparticle-Aptamer Bioconjugates: A New Approach for Targeting Prostate Cancer Cells," *Cancer Research*, 64:7668-7672 (2004).
Farokhzad, et al., "Nanoparticle-aptamer bioconjugates for cancer targeting", *Expert Opin. Drug Delivery*, 3(3):311-324 (2006).
Farokhzad, et al., "Targeted nanoparticle-aptamer bioconjugates for cancer chemotherapy in vivo.", *Proc. Natl. Acad. ScL, USA*, 103(16):6315-6320 (2006).
Farr, et al., "The structure of the sinus wall of the lymph node relative to its endocytic properties and transmural cell passage.", *Am. J. Anat.*, 157(3):265-284 (1980).
Fire, et al., "Potent and specific genetic interference by double-stranded RNA in *Caenorhabditis elegans.*", *Nature*, 391(6669):806-811 (1998).
Fonseca, et al., "Paclitaxel-loaded PLGA nanoparticles: preparation, physicochemical characterization and in vitro anti-tumoral activity.", *J. Control. Release*, 83(2):273-286 (2002).
Fracasso, et al., "Anti-tumor effects of toxins targeted to the prostate specific membrane antigen.", *Prostate*, 53(1):9-23 (2002).
Francis, et al., "A phase I trial of antibody directed enzyme prodrug therapy (ADEPT) in patients with advanced colorectal carcinoma or other CEA producing tumours.", *Br. J. Cancer*, 87(6):600-607 (2002).
Frankel, et al., "Phase I trial of a novel diphtheria toxin/granulocyte macrophage colony-stimulating factor fusion protein (DT388GMCSF) for refractory or relapsed acute myeloid leukemia.", *Clin. Cancer Res.*, 8(5):1004-1013 (2002).
Frederick, et al., "Structural comparison of anticancer drug-DNA complexes: adriamycin and daunomycin.", *Biochemistry*, 29(10):2538-2549 (1990).
Froidevaux, et al., "Somatostatin analogs and radiopeptides in cancer therapy.", *Biopolymers*, 66(3):161-183 (2002).
Fujita, et al., "Cytokine profiling of prostatic fluid from cancerous prostate glands identifies cytokines associated with extent of tumor and inflammation", *The Prostate*, 68(8):872-882 (2008).
Gao, et al., "A method for the generation of combinatorial antibody libraries using pIX phage display," *Proc. Natl. Acad. Sci. U.S.A.*, 99(20): 12612-6 (2002).
Gao, et al., "In vivo cancer targeting and imaging with semiconductor quantum dots.", *Nat. Biotechnol.*, 22(8):969-976 (2004).
Gao, et al., "In vivo molecular and cellular imaging with quantum dots.", *Curr. Op. Biotechnol.*, 16:63-72 (2005).
Gershlick, "Treating atherosclerosis: local drug delivery from laboratory studies to clinical trials," *Atherosclerosis*, 160(2): 259-71 (2002).

(56) References Cited

OTHER PUBLICATIONS

Gillies, et al., "An anti-CD20-IL-2 immunocytokine is highly efficacious in a SCID mouse model of established human B lymphoma.", *Blood*, 105(10):3972-3978 (2005).
Grauer, et al., "Identification, purification, and subcellular localization of prostate-specific membrane antigen PSM' protein in the LNCaP prostatic carcinoma cell line.", *Cancer Res.*, 58(21):4787-4789 (1998).
Gref, et al., "Biodegradable long-circulating polymeric nanospheres.", *Science*, 263(5153):1600-1603 (1994).
Haensler, et al., "Polyamidoamine cascade polymers mediate efficient transfection of cells in culture", *Bioconjugate Chem.*, 4(5):372-379 (1993).
Haj, et al., "New findings in the study on the intercalation of bisdaunorubicin and its monomeric analogues with naked and nucleus DNA.", *Chem. Biol. Interact.*, 145(3):349-358 (2003).
Hanes, et al., "Polymer microspheres for vaccine delivery.", *Pharm. Biotechnol.*, 6:389-412 (1995).
Hangartner, et al., "Antiviral immune responses in gene-targeted mice expressing the immunoglobulin heavy chain of virus-neutralizing antibodies.", *Proc. Natl. Acad. Sci., USA*, 100:12883-12888 (2003).
Hannon, et al., "Unlocking the potential of the human genome with RNA interference", *Nature*, 431(7006):371-378 (2004).
Harada and Kataoka, "Supramolecular assemblies of block copolymers in aqueous media as nanocontainers relevant to biological applications", *Progress Polymer Sci.*, 31(11):949-982 (2006).
Harper, et al., "Efficacy of a bivalent L1 virus-like particle vaccine in prevention of infection with human papillomavirus types 16 and 18 in young women: a randomised controlled trial.", *Lancet*, 364(9447):1757-1765 (2004).
Haseloff and Gerlach, "Simple RNA enzymes with new and highly specific endoribonuclease activities.", *Nature*, 334(6183):585-591 (1988).
Hawiger, et al., "Dendritic cells induce peripheral T cell unresponsiveness under steady state conditions in vivo.", *J. Exp. Med.* 194(6):769-779 (2001).
He, et al., "A microRNA polycistron as a potential human oncogene," *Nature*, 435(7043):828-833 (2005).
Hélène, "The anti-gene strategy: control of gene expression by triplex-forming-oligonucleotides.", *Anticancer Drug Des.* 6(6):569-584 (1991).
Helene, et al., "Control of gene expression by triple helix-forming oligonucleotides. The antigene strategy.", *Ann, N.Y. Acad. Sci.* 660:27-36 (1992).
Hermann and Patel, "Adaptive recognition by nucleic acid aptamers," *Science*, 287:820-825 (2000).
Hieda, et al., "Active Immunization Alters the Plasma Nicotine Concentration in Rats", *J. Pharmacol. Exp. Therapeutics*, 283:1076-1081 (1997).
Hieda, et al., "Immunization of rats reduces nicotine distribution to brain", *Psychopharmacology*, 143:150-157 (1999).
Horoszewicz, et al., "Monoclonal antibodies to a new antigenic marker in epithelial prostatic cells and serum of prostatic cancer patients.", *Anticancer Res.*, 7(5B):927-935 (1987).
Houghton, "General method for the rapid solid-phase synthesis of large number of peptides: Specificity of antigen-antibody interaction at the level of individual amino acids", *Immunol.*, 82:5131-5135 (1985).
Jackson, et al., "Design and pharmacological activity of phosphinic acid based NAALADase inhibitors.", *J. Med. Chem.*, 44(24):4170-4175 (2001).
Jackson, et al., "Design of NAALADase inhibitors: a novel neuroprotective strategy.", *Curr. Med. Chem.*, 8(8):949-957 (2001).
Johnson and Prud'Homme, "Mechanism for rapid self-assembly of block copolymer nanoparticles.", *Phys. Rev. Lett.*, 91(11):118302 (2003).
Jones and Leroux, "Polymeric micelles—a new generation of colloidal drug carriers", *Eur. J. Pharmaceutics Biopharmaceutics*, 48:101-111 (1999).
Jung, et al., "Tetanus Toxoid Loaded Nanoparticles from Sulfobutylated Poly(Vinyl Alcohol)-Graft-Poly(Lactide-co-Glycolide): Evaluation of Antibody Response After Oral and Nasal Application in Mice", *Pharmaceutical Research*, 18(3):352-360 (2001).
Junt, et al., "Subcapsular sinus macrophages in lymph nodes clear lymph-borne viruses and present them to antiviral B cells", *Nature*, 450:110-116 (2007).
Kabanov, et al., "DNA Complexes with Polycations for the Delivery of Genetic Material into Cells", *Bioconjugate Chem.*, 6(1):7-20 (1995).
Kamentsky, "Laser scanning cytometry.", *Methods Cell Biol.*, 63:51-87 (2001).
Kanashiro, et al., "Inhibition of mutant p53 expression and growth of DMS-153 small cell lung carcinoma by antagonists of growth hormone-releasing hormone and bombesin.", *Proc. Natl. Acad. Sci., USA*, 100(26):15836-15841 (2003).
Karlin and Altschul, "Applications and statistics for multiple high-scoring segments in molecular sequences.", *Proc. Natl Acad. Sci. USA*, 90(12):5873-5877 (1993).
Karlin and Altschul, "Methods for assessing the statistical significance of molecular sequence features by using general scoring schemes.", *Proc. Natl Acad Sci. USA*, 87:2264-2268 (1990).
Karrer, et al., "On the key role of secondary lymphoid organs in antiviral immune responses studied in alymphoplastic (aly/aly) and spleenless (Hox11(-)/-) mutant mice.", *J. Exp. Med.*, 185(12):2157-2170 (1997).
Kelly, et al., "The Optical Properties of Metal Nanoparticles: The Influence of Size, Shape, and Dielectric Environment", *J. Phys. Chem. B.*, 107(3):668-677 (2003).
Khademhosseini, et al., "Cell docking inside microwells within reversibly sealed microfluidic channels for fabricating multiphenotype cell arrays," *Lab Chip*, 5(12):1380-6 (2005).
Knight, et al., "Hydrodynamic Focusing on a Silicon Chip: Mixing Nanoliters in Microseconds", *Phys. Rev. Lett.*, 80:3863-3866 (1998).
Köhrer and Rajbhandary, "Proteins carrying one or more unnatural amino acids," In Ibba, et al., (eds.), *Aminoacyl-tRNA Synthetases*, Landes Bioscience, Chapter 31 (2005).
Köhrer, et al., "Complete set of orthogonal 21st aminoacyl-tRNA synthetase-amber, ochre and opal suppressor tRNA pairs: concomitant suppression of three different termination codons in an mRNA in mammalian cells.", *Nucleic Acids Res.*, 32(21):6200-6211 (2004).
Köhrer, et al., "Import of amber and ochre suppressor tRNAs into mammalian cells: a general approach to site-specific insertion of amino acid analogues into proteins.", *Proc. Natl. Acad. Sci., USA*, 98(25):14310-14315 (2001).
Koivunen, et al., "Phage libraries displaying cyclic peptides with different ring sizes: ligand specificities of the RGD-directed integrins.", *Biotechnology (NY)*, 13(3):265-270 (1995).
Koivunen, et al., "Tumor targeting with a selective gelatinase inhibitor", *Nat. Biotechnol.*, 17:768-774 (1999).
Konan, et al., "Preparation and characterization of sterile sub-200 nm meso-tetra(4-hydroxylphenyl)porphyrin-loaded nanoparticles for photodynamic therapy", *Eur. J. Pharmaceutics Biopharmaceutics*, 55:115-124 (2003).
Kozikowski, et al., "Synthesis of urea-based inhibitors as active site probes of glutamate carboxypeptidase II: efficacy as analgesic agents.", *J. Med. Chem.*, 47(7):1729-1738 (2004).
Krieg, et al., "CpG motifs in bacterial DNA trigger direct B-cell activation.", *Nature*, 374(6522):546-549 (1995).
Kreitman, et al., "Efficacy of the anti-CD22 recombinant immunotoxin BL22 in chemotherapy-resistant hairy-cell leukemia.", *N. Engl J. Med.*, 345(4):241-347 (2001).
Kreitman, et al., "Phase I trial of recombinant immunotoxin anti-Tac(Fv)-PE38 (LMB-2) in patients with hematologic malignancies.", *J. Chin. Oncol.*, 18(8):1622-1636 (2000).
Kukowska-Latallo, et al., "Efficient transfer of genetic material into mammalian cells using Starburst polyamidoamine dendrimers", *Proc. Natl. Acad. Sci., USA*, 93(10):4897-4902 (1996).
Kumar, et al., "Inhibition of angiogenesis and tumor growth by SCH221153, a dual alpha(v)beta3 and alpha(v)beta5 integrin receptor antagonist.", *Cancer Res.*, 61(5):2232-2238 (2001).

(56) References Cited

OTHER PUBLICATIONS

Kwon, et al., "Pseudopoly(amino acids): A study of the synthesis and characterization of poly(acyl-hydroxyproline-esters)", *Macromolecules*, 22:3250-3255 (1989).
Laakkonen, et al., "Antitumor activity of a homing peptide that targets tumor lymphatics and tumor cells.", *Proc. Natl. Acad. Sci., USA*, 101(25):9381-9386 (2004).
Labhasetwar, et al., "Arterial uptake of biodegradable nanoparticles: Effect of surface modifications ," *J. Pharm. Sci.*, 87(10): 1229-34 (1998).
Langer, "Biomaterials in drug delivery and tissue engineering: one laboratory's experience.", *Acc. Chem. Res.*, 33(2):94-101 (2000).
Langer, "New methods of drug delivery," *Science*, 249(4976):1527-33 (1990).
Langer, "Selected advances in drug delivery and tissue engineering", *J. Control. Release*, 62:7-11 (1999).
Langone, et al., "Nicotine and its metabolites. Radioimmunoassays for nicotine and cotinine", *Biochem.*, 12(24):5025-5030 (1973).
Langone & Van Vunakis, "Radioimmunoassay of Nicotine, Cotinine, and γ-(3-Pyridyl)-γ-oxo-N-methylbutyramide", *Met. Enzymol.*, 84:628-640 (1982).
Leamon, et al., "Cytotoxicity of folate-*Pseudomonas* exotoxin conjugates toward tumor cells. Contribution of translocation domain.", *J. Biol. Chem.*, 268(33):24847-24854 (1993).
Leamon, et al., "Selective targeting of malignant cells with cytotoxin-folate conjugates.", *J. Drug Target.*, 2(2):101-112 (1994).
Leopold, et al., "Fluorescent virions: dynamic tracking of the pathway of adenoviral gene transfer vectors in living cells.", *Human Gene Therapy*, 9(3):367-378 (1998).
Leroy, et al., "Radioimmunodetection of lymph node invasion in prostatic cancer. The use of iodine 123 (123I)-labeled monoclonal anti-prostatic acid phosphatase (PAP) 227 A F(ab')2 antibody fragments in vivo.", *Cancer*, 64(1):1-5 (1989).
Leucuta, et al., "Albumin microspheres as a drug delivery system for epirubicin: pharmaceutical, pharmacokinetic and biological aspects," *International Journal of Pharmaceutics*, 41: 213-7 (1988).
Lim, et al., "A Self-Destroying Polycationic Polymer: Biodegradable Poly(4-hydroxy-l-proline ester)", *J. Am. Chem. Soc.*, 121(24):5633-5639 (1999).
Lim, et al., "Cationic hyperbranched poly(amino ester): a novel class of DNA condensing molecule with cationic surface, biodegradable three-dimensional structure, and tertiary amine groups in the interior.", *J. Am. Chem. Soc*, 123(10):2460-2461 (2001).
Lin, et al., "A microRNA polycistron as a potential human oncogene p828", *Nature*, 435(7043):828-833 (2005).
Lin, et al., "Well-Ordered Mesoporous Silica Nanoparticles as Cell Markers", *Chem. Mater.*, 17:4570-4573 (2005).
Liu, et al., "Cell-Surface labeling and internalization by a fluorescent inhibitor of prostate-specific membrane antigen", *The Prostate*, 68(9):955-964 (2008).
Liu, et al., "Constitutive and antibody-induced internalization of prostate-specific membrane antigen.", *Cancer Res.*, 58(18):4055-4060 (1998).
Liu, et al., "Folate-targeted enzyme prodrug cancer therapy utilizing penicillin-V amidase and a doxorubicin prodrug.", *J. Drug Target.*, 7:43-53 (1999).
Liu, et al., "Hypermethylation of MCAM gene is associated with advanced tumor stage in prostate cancer", *The Prostate*, 68(4):418-426 (2008).
Liu, et al., "Monoclonal antibodies to the extracellular domain of prostate-specific membrane antigen also react with tumor vascular endothelium.", *Cancer Res.*, 57(17):3629-3634 (1997).
Low, et al., "Folate receptor-targeted drugs for cancer and inflammatory diseases.", *Adv. Drug Deliv. Rev.*, 56(8):1055-1058 (2004).
Lu, et al., "MicroRNA expression profiles classify human cancers", *Nature*, 435(7043):834-838 (2005).
Ludewig, et al., "Induction of optimal anti-viral neutralizing B cell responses by dendritic cells requires transport and release of virus particles in secondary lymphoid organs.", *Eur. J. Immunol.*, 30(1):185-196 (2000).
Lupold, et al., "Identification and characterization of nuclease-stabilized RNA molecules that bind human prostate cancer cells via the prostate-specific membrane antigen.", *Cancer Res.*, 62(14):4029-4033 (2002).
Lyu, et al., "The immunocytokine scFv23/TNF sensitizes HER-2/neu-overexpressing SKBR-3 cells to tumor necrosis factor (TNF) via up-regulation of TNF receptor-1.", *Mol. Cancer Ther.*, 4(8):1205-1213 (2005).
Maher, "DNA triple-helix formation: An approach to artificial gene repressors?", *Bioassays* 14:807-815 (1992).
Majer, et al., "Synthesis and biological evaluation of thiol-based inhibitors of glutamate carboxypeptidase II: discovery of an orally active GCP II inhibitor.", *J. Med. Chem.*, 46(10):1989-1996 (2003).
Manolova, et al., "Nanoparticles target distinct dendritic cell populations according to their size", *Eur. J. Immunol.*, 38:1404-1413 (2008).
Manz, et al., "Capillary electrophoresis on a chip", *J. Chromatography*, 593:253-258 (1992).
Mathiowitz, et al., "Polyanhydride Microspheres as Drug Carriers I. Hot Melt Encapsulation", *J. Control. Release*, 5:13-22 (1987).
Mathiowitz, et al., "Novel microcapsules for delivery systems", *Reactive Polymers*, 6:275-283 (1987).
Mathiowitz, et al., "Polyanhydride Microspheres as Drug Carriers. II.Microencapsulation by Solvent Removal", *J. Appl. Polymer Sci.*, 35:755-774 (1988).
Mattheakis, et al., "Optical coding of mammalian cells using semiconductor quantum dots.", *Analytical Biochemistry*, 327(2):200-208 (2004).
Maung, et al., "Probing for a hydrophobic a binding register in prostate-specific membrane antigen with phenylalkylphosphonamidates.", *Bioorg. Med. Chem.*, 12(18):4969-4979 (2004).
McDevitt, et al., "An alpha-particle emitting antibody ([213Bi]J591) for radioimmunotherapy of prostate cancer.", *Cancer Res.*, 60(21):6095-6100 (2000).
McDevitt, et al., "Tumor therapy with targeted atomic nanogenerators.", *Science*, 294(5546):1537-1540 (2001).
Mead, et al., "Laboratory vector competence of black flies (Diptera:Simuliidae) for the Indiana serotype of vesicular stomatitis virus.", *Ann. N.Y. Acad. Sci.*, 916:437-443 (2000).
Meister, et al., "Mechanisms of gene silencing by double-stranded RNA.", *Nature*, 431(7006):343-349 (2004).
Melani, et al., "Targeting of interleukin 2 to human ovarian carcinoma by fusion with a single-chain Fv of antifolate receptor antibody.", *Cancer Res.*, 58(18):4146-4154 (1998).
Mempel, et al., "T-cell priming by dendritic cells in lymph nodes occurs in three distinct phases.", *Nature*, 427(6970):154-159 (2004).
Metelitsa, et al., "Antidisialoganglioside/granulocyte macrophage-colony-stimulating factor fusion protein facilitates neutrophil antibody-dependent cellular cytotoxicity and depends on FcgammaRII (CD32) and Mac-1 (CD11b/CD18) for enhanced effector cell adhesion and azurophil granule exocytosis.", *Blood*, 99(11):4166-4173 (2002).
Meyers, et al., "Development of monoclonal antibody imaging of metastatic prostatic carcinoma.", *Prostate*, 14(3):209-220 (1989).
Milligan and Uhlenbeck, "Synthesis of small RNAs using T7 RNA polymerase," *Methods in Enzymology*, 180:51-62 (1989).
Moghimi, et al., "Long-circulating and target-specific nanoparticles: theory to practice.", *Pharmacol. Rev.*, 53(2): 283-318 (2001).
Mulligan, "The basic science of gene therapy," *Science*, 260(5110):926-32 (1993).
Murphy, et al., "Isolation and characterization of monoclonal antibodies specific for the extracellular domain of prostate specific membrane antigen.", *J. Urol.*, 160(6 Pt 2):2396-2401 (1998).
Murray, et al., "Synthesis and characterization of monodisperse nanocrystals and close-packed nanocrystal assemblies", *Ann. Rev. Mat. Sci.*, 30:545-610 (2000).
Myers and Miller, *CABIOS* (1988).
Nan, et al., "Dual function glutamate-related ligands: discovery of a novel, potent inhibitor of glutamate carboxypeptidase II possessing mGluR3 agonist activity.", *J. Med. Chem.*, 43(5):772-774 (2000).
Neidle, "The molecular basis for the action of some DNA-binding drugs.", *Prog. Med. Chem.*, 16:151-221 (1979).

(56) References Cited

OTHER PUBLICATIONS

Nguyen and Wu, "Micromixers—a review.", *J. Micromechan. Microeng.*, 15:R1 (2005).
Notter, et al., "Targeting of a B7-1 (CD80) immunoglobulin G fusion protein to acute myeloid leukemia blasts increases their costimulatory activity for autologous remission T cells.", *Blood*, 97(10):3138-3145 (2001).
Ochsenbein, et al., "Protective T cell-independent antiviral antibody responses are dependent on complement.", *J. Exp. Med.*, 190(8):1165-1174 (1999).
Ochsenbein, et al., "Control of early viral and bacterial distribution and disease by natural antibodies.", *Science*, 286(5447):2156-2159 (1999).
O'Donnell, et al., "c-Myc-regulated microRNAs modulate E2F1 expression," *Nature*, 435(7043): 839-843 (2005).
Okada, et al., "Antigen-engaged B cells undergo chemotaxis toward the T zone and form motile conjugates with helper T cells.", *PLoS Biol.*, 3(6):e150 (2005).
Oliver, et al., "Conformational and SAR analysis of NAALADase and PSMA inhibitors.", *Bioorg. Med. Chem.*, 11(20):4455-4461 (2003).
Pape, et al., "The humoral immune response is initiated in lymph nodes by B cells that acquire soluble antigen directly in the follicles.", *Immunity*, 26(4):491-502 (2007).
Papisov, "Acyclic Polyacetals from Polysaccharides: Biomimetic Biomedical "Stealth" Polymers", *ACS Symposium Series*, 786:301-314 (2001).
Parekh, et al., "Biomarkers for Prostate Cancer Detection", *The Journal of Urology*, 178(6):2252-2259 (2007).
Pasqualini, et al., "Aminopeptidase N is a receptor for tumor-homing peptides and a target for inhibiting angiogenesis.", *Cancer Res.*, 60(3):722-727 (2000).
Patri, et al., "Synthesis and in Vitro Testing of J591 Antibody-Dendrimer Conjugates for Targeted Prostate Cancer Therapy", *Bioconj. Chem.*, 15:1174-1181 (2004).
Pellegrino, et al., "On the development of colloidal nanoparticles towards multifunctional structures and their possible use for biological applications.", *Small*, 1(1):48-63 (2005).
Pfohl, et al., "Trends in microfluidics with complex fluids.", *Chemphyschem*, 4(12):1291-1298 (2003).
Phillips, et al., "Enhanced antibody response to liposome-associated protein antigens: preferential stimulation of IgG2a/b production.", *Vaccine*, 10(3):151-158 (1992).
Porkka, et al., "A fragment of the HMGN2 protein homes to the nuclei of tumor cells and tumor endothelial cells in vivo.", *Proc. Natl. Acad. Sci., USA*, 99(11):7444-7449 (2002).
Putnam, et al., "Poly(4-hydroxy-l-proline ester): Low-Temperature Polycondensation and Plasmid DNA Complexation", *Macromolecules*, 32(11):3658-3662 (1999).
Qi, et al., "Extrafollicular activation of lymph node B cells by antigen-bearing dendritic cells", *Science*, 312(5780):1672-1676 (2006).
Quintanar-Guerrero, et al., "Preparation Techniques and Mechanisms of Formation of Biodegradable Nanoparticles from Preformed Polymers", *Drug Dev. Industrial Pharmacy*, 24(12):1113-1128 (1998).
Reddy, et al., "Exploiting lymphatic transport and complement activation in nanoparticle vaccines", *Nat. Biotech.*, 25(10):1159-1164 (2007).
Reif, et al., "Balanced responsiveness to chemoattractants from adjacent zones determines B-cell position.", *Nature*, 416(6876):94-99 (2002).
Reiher, et al., "Inhibition of tumor growth by systemic treatment with thrombospondin-1 peptide mimetics.", *Int. J. Cancer*, 98(5):682-689 (2002).
Reubi, et al., "Peptide receptors as molecular targets for cancer diagnosis and therapy.", *Endocr. Rev.*, 24(4):389-427 (2003).
Reynolds, et al., "Rational siRNA design for RNA interference.", *Nat. Biotechnol.*, 22(3):326-330 (2004).
Robbins, et al., "Stable expression of shRNAs in human CD34+ progenitor cells can avoid induction of interferon responses to siRNAs in vitro", *Nature Biotechnology*, 24(5):566-571 (2006).
Robinson, et al., "LEAPT: lectin-directed enzyme-activated prodrug therapy.", *Proc. Natl. Acad. Sci., USA*, 101(40):14527-14532 (2004).
Roost, et al., "Mapping of the dominant neutralizing antigenic site of a virus using infected cells.", *J. Immunol. Methods*, 189(2):233-242 (1996).
Rossbacher and Shlomchik, "The B cell receptor itself can activate complement to provide the complement receptor 1/2 ligand required to enhance B cell immune responses in vivo.", *J. Exp. Med.*, 198(4):591-602 (2003).
Sampson, et al., "Progress report of a Phase I study of the intracerebral microinfusion of a recombinant chimeric protein composed of transforming growth factor (TGF)-alpha and a mutated form of the *Pseudomonas* exotoxin termed PE-38 (TP-38) for the treatment of malignant brain tumors.", *J. Neurooncol.*, 65(1):27-35 (2003).
Santoyo, et al., "Highly specific and accurate selection of siRNAs for high-throughput functional assays.", *Bioinformatics*, 21(8):1376-1382 (2005).
Sarver, et al., "Ribozymes as potential anti-HIV-1 therapeutic agents.", *Science* 247(4947):1222-1225 (1990).
Schally, et al., "Peptide analogs in the therapy of prostate cancer.", *Prostate*, 45(2):158-166 (2000).
Schultz, "Plasmon resonant particles for biological detection", *Curr. Op. Biotechnol.*, 14:13-22 (2003).
Schultz, et al., "Single-target molecule detection with nonbleaching multicolor optical immunolabels.", *Proc. Natl. Acad. Sci., USA*, 97(3):996-1001(2000).
Shaida, et al., "Expression of BNIP3 correlates with hypoxia-inducible factor (HIF)-1α, HIF-2α and the androgen receptor in prostate cancer and is regulated directly by hypoxia but not androgens in cell lines", *The Prostate*, 68(3):336-343 (2008).
Shen, et al., "Enhanced and prolonged cross-presentation following endosomal escape of exogenous antigens encapsulated in biodegradable nanoparticles", *Immunol.*, 117:78-88 (2006).
Shestopalov, et al., "Multi-step synthesis of nanoparticles performed on millisecond time scale in a microfluidic droplet-based system.", *Lab on a Chip*, 4(4):316-321 (2004).
Shiow, et al., "CD69 acts downstream of interferon-alpha/beta to inhibit S1P1 and lymphocyte egress from lymphoid organs.", *Nature*, 440(7083):540-544 (2006).
Silver, et al., "Prostate-specific membrane antigen expression in normal and malignant human tissues.", *Clin. Cancer Res.*, 3(1):81-85 (1997).
Smith-Jones, et al., "In vitro characterization of radiolabeled monoclonal antibodies specific for the extracellular domain of prostate-specific membrane antigen.", *Cancer Res.*, 60(18):5237-5243 (2000).
Sondel, et al., "Preclinical and clinical development of immunocytokines.", *Curr. Opin. Investig. Drugs*, 4(6):696-700 (2003).
Song, et al., "A Microfluidic System for Controlling Reaction Networks in Time", *Angewandte Chemie-Int'l Ed.*, 42:768-772 (2003).
Spooner, et al., "A novel vascular endothelial growth factor-directed therapy that selectively activates cytotoxic prodrugs.", *Br. J. Cancer*, 88(10):1622-1630 (2003).
Stoermer, et al., "Synthesis and biological evaluation of hydroxamate-Based inhibitors of glutamate carboxypeptidase II.", *Bioorg. Med. Chem. Lett.*, 13(13):2097-2100 (2003).
Storm, et al., "Surface Modification of Nanoparticles to Oppose Uptake by the Mononuclear Phagocyte System", *Adv. Drug Deliv. Rev.*, 17:31-48 (1995).
Stroock, et al., "Chaotic mixer for microchannels.", *Science*, 295(5555):647-651 (2002).
Sutcliffe, et al., "Antibodies that react with predetermined sites on proteins", *Science*, 219:660-666 (1983).
Tang, et al, "In Vitro Gene Delivery by Degraded Polyamidoamine Dendrimers", *Bioconjugate Chem.*, 7:703-714 (1996).
Tang, et al., "Prostate targeting ligands based on N-acetylated alpha-linked acidic dipeptidase.", *Biochem. Biophys. Res. Commun.*, 307(1):8-14 (2003).

(56) References Cited

OTHER PUBLICATIONS

Taylor, et al., "Macrophage receptors and immune recognition.", *Annu. Rev. Immunol.*, 23:901-944 (2005).
Tindall, et al., "The Rationale for Inhibiting 5α-Reductase Isoenzymes in the Prevention and Treatment of Prostate Cancer", *The Journal of Urology*, 179(4):1235-1242 (2008).
Trindade, et al., "Nanocrystalline Semiconductors: Synthesis, Properties, and Perspectives", *Chem. Mat.*, 13(11):3843-3858 (2001).
Tsukamoto, et al., "Phosphonate and phosphinate analogues of N-acylated gamma-glutamylglutamate. potent inhibitors of glutamate carboxypeptidase II.", *Bioorg. Med. Chem. Lett.*, 12(16):2189-2192 (2002).
Uhrich, et al., "Polymeric Systems for Controlled Drug Release", *Chem. Rev.*, 99(11):3181-3198 (1999).
Unkeless, et al., "Structure and function of human and murine receptors for IgG.", *Annu. Rev. Immunol.*, 6:251-281 (1998).
Uwatoku, et al., "Application of Nanoparticle Technology for the Prevention of Restenosis After Balloon Injury in Rats," *Circ. Res.*, 92(7): e62-9 (2003).
Valentini, et al., "Association of anthracycline derivatives with DNA: a fluorescence study.", *Farmaco [Sci]*, 40:377-390 (1985).
Vallabhajosula, et al., "Radioimmunotherapy of prostate cancer in human xenografts using monoclonal antibodies specific to prostate specific membrane antigen (PSMA): studies in nude mice.", *Prostate*, 58(2):145-155 (2004).
Vascotto, et al., "Antigen presentation by B lymphocytes: how receptor signaling directs membrane trafficking.", *Curr., Opin., Immunol.*, 19(1):93-98 (2007).
Vihko, et al., "Radioimaging of Prostatic Carcinoma With Prostatic Acid Phosphatase—Specific Antibodies", *Biotechnology in Diagnostics*, 131-134 (1985).
Von Allmen, et al., "V domain of RAGE interacts with AGEs on prostate carcinoma cells", *The Prostate*, 68(7):748-758 (2008).
Von Andrian and Mempel, "Homing and cellular traffic in lymph nodes.", *Nat. Rev. Immunol.*, 3(11):867-878 (2003).
Wang, et al., "A novel biodegradable gene carrier based on polyphosphoester.", *J. Am. Chem. Soc.*, 123(38):9480-9481 (2001).
Wang, et al., "Autoantibody signatures in prostate cancer.", *N Engl J Med*, 353(12):1224-1235 (2005).
Wang, et al., "Identification of prostate specific membrane antigen (PSMA) as the target of monoclonal antibody 107-1A4 by proteinchip; array, surface-enhanced laser desorption/ionization (SELDI) technology.", *Int. J. Cancer*, 92(6):871-876 (2001).
Wang, et al., "Interactions between an anthracycline antibiotic and DNA: molecular structure of daunomycin complexed to d(CpGpTpApCpG) at 1.2-A resolution.", *Biochemistry*, 26(4):1152-1163 (1987).
Weaver, et al., "Transferrin receptor ligand-targeted toxin conjugate (Tf-CRM107) for therapy of malignant gliomas.", *J. Neurooncol.*, 65(1):3-13 (2003).
Wessels, et al., "Studies of group B streptococcal infection in mice deficient in complement component C3 or C4 demonstrate an essential role for complement in both innate and acquired immunity.", *Proc. Natl. Acad. Sci., USA*, 92(25):11490-11494 (1995).
Whelan, et al., "Efficient recovery of infectious vesicular stomatitis virus entirely from cDNA clones.", *Proc. Natl. Acad. Sci., USA*, 92(18):8388-8392 (1995).
Wilson, et al., "The Structure of an Antigenic Determinant in a Protein", *Cell*, 37:767-778 (1984).
Wind, et al., "An integrated confocal and magnetic resonance microscope for cellular research.", *J. Magn. Reson.*, 147(2):371-377 (2000).
Wlotzka, et al., "In vivo properties of an anti-GnRH Spiegelmer: an example of an oligonucleotide-based therapeutic substance class," *Proc. Natl. Acad. Sci. U. S. A.*, 99(13):8898-902 (2002).
Wright, et al., "Cyclophosphamide/granulocyte colony-stimulating factor causes selective mobilization of bone marrow hematopoietic stem cells into the blood after M phase of the cell cycle.", *Blood*, 97(8):2278-2285 (2001).
Wu, "Arming antibodies: prospects and challenges for immunoconjugates.", *Nat. Biotechnol.*, 23(9):1137-1146 (2005).
Wu, et al., "Immunofluorescent labeling of cancer marker Her2 and other cellular targets with semiconductor quantum dots.", *Nat. Biotechnol.*, 21(1):41-46 (2003).
Yang, "Imaging of vascular gene therapy.", *Radiology*, 228:36-249 (2003).
Yoo, et al., "In vitro and in vivo anti-tumor activities of nanoparticles based on doxorubicin-PLGA conjugates.", *J. Control. Release*, 68(3):419-431 (2000).
Yuan, et al., "siRNA Selection Server: an automated siRNA oligonucleotide prediction server.", *Nucl. Acids. Res.*, 32:W130-W134 (2004).
Zamore, et al., "RNAi: double-stranded RNA directs the ATP-dependent cleavage of mRNA at 21 to 23 nucleotide intervals.", *Cell*, 101(1):25-33 (2000).
Zauner, et al., "Polylysine-basedtransfection systems utilizing receptor-mediated delivery.", *Adv. Drug Del. Rev.*, 30:97-113 (1998).
Zhang, et al., "The proliferative effect of estradiol on human prostate stromal cells is mediated through activation of ERK", *The Prostate*, 68(5):508-516 (2008).
Zheng, et al., "Highly fluorescent, water-soluble, size-tunable gold quantum dots.", *Phys. Rev. Lett.*, 93(7):077402 (2004).
Zhou, et al., "Investigation on a novel core-coated microspheres protein delivery system.", *J. Control. Release*, 75(1-2):27-36 (2001).
Zhou, et al., "Preparation of poly(L-serine ester): a structural analog of conventional poly(L-serine)", *Macromolecules*, 23(14):3399-3406 (1990).
Zuker, "Mfold web server for nucleic acid folding and hybridization prediction", *Nuc. Acid. Res.*, 31:3406-3415 (2003).
Adams, et al., Amphiphilic block copolymers for drug delivery, J. Pharm. Sci., 92 (7):1343-55 (2003).
Barinka, et al., "Interactions between human glutamate carboxypeptidase II and urea-based inhibitors: Structural characterization", J Med. Chem.,51:7737-43 (2008).
Barinka, et al., "Structural insight into the pharmacophore pocket of human glutamate carboxypoeptidase II", J. Med Chem., 50:3267-73 (2007).
Caliceti, et al. "Effective protein release from PEG/PLA nano-particles produced by compressed gas anti-solvent precipitation techniques", J of Cont. Release, 94:195-205 (2004).
Chandran, et al, "Characterization of a targeted nanoparticle functionalized with a Urea-based inhibitor of prostate-specific membrane antigen (PSMA)", Cancer Biol & Therapy, 7 (4):1-9 (2008).
Chen, et al., "Radiohalogenated prostate-specific membrane antigen (PSMA)-based ureas as imaging agents for prostate cancer", J Med Chem., 51 (24):7933-43 (2008).
Dancey, et al., "Therapeutic Targets:MTOR an related pathways", Cancer Biol. Ther., 5(9):1065-73 (2006).
Ewesuedo and Ratain, "Systemically administered drugs", Drug Delivery Systems in Cancer, Humana Press, Chapter 1:3-14 (2004).
Foss, "Synthesis and validation of a novel small-molecule fluorescent probe for PSMA expression in human tumor neovasculature", Poster session: Novel probes and activation strateies, part 3,4th annual meeting, Society for Molecular Imaging, Sep. 7-10 (2005).
Gref, et al., "Biodegradeable long-circulation polymeric nanospheres", Science, 263:1600-03 (1994).
Gu, et al., "Precise engineering of targeted nanoparticles by using self-assembled biointegrated block copolymers", PNAS, 105(7):2586-91 (2008).
Humblet, et al. "An HPLC/mass spectrometry platform for the development of multimodality contrast agents and targeted therapeutics: prostate-specific membrane antigen small derivatives", Contrast Med. Mol. Imaging, 1:196-211 (2006).
Humblet, et al. "High-affinity near-infrared fluorescent small-molecule contras agents for in vivo imaging of prostate-specific membrane antigen", Molecular Imaging, 4:448-62 (2005).
Japaprakash, et al., "Design and synthesis of a PSMA inhibitor-doxorubicin conjugate for targeted prostrate cancer therapy", Chem Med Chem, 1:299-302 (2006).
Jiang, et al., "Preparation of PLA and PLGA nanoparticles y binary organic solvent diffusion method", J. Cent. South Univ Technol, 10(3):202-06 (2003).

(56) References Cited

OTHER PUBLICATIONS

Kozikowski, et al. "Design of remarkably simple, yet potent urea-based inhibitors of glutamate carboxypeptidase II (NAALADase)", J. Med Chem, 44:298-301 (2001).
Maresca, et al., "A series of halogenated heterodimeric inhibitors of prostate specific membrane antigen (PSMA) as radiolabeled probes for targeting prostate cancer", J. Med Chem., 52(2):347-57 (2009).
Mease, et al., "N-[N-[(S)-1,3-Dicarboxypropyl]carbamoyl]-4-[18F]fluorobenzyl-L-cysteine, [18F]DCFBC: a new imaging probe for prostate cancer", Clin. Cancer Res., 14(10):3036-43 (2008).
Misra, et al., "Production of multimeric prostrate-specific membrane antigen small-molecule radiotracers using a solid-phase 99mTc preloading strategy", J Nuclear Medicine, 48(8):1379-89 (2007).
Pomper, et al., "New developments in molecular imaging of prostate cancer", Topical Symposium on Advanced Molecular Imaging Techniques in the detection, diagnosis, therapy and follow-up of Cancer, Palazzo Barberini, Rome Dec. 6, 2005.
Pulkkinen, et al., "Three-step tumor of paclitaxel using biotinylated PLA-PEG nanoparticles and avidin-biotin technology: Formulation developing and in vitro anticancer activity", Eur. J Pharm. Biopharm., 70:66-74 (2008).
Sapra, et al., "Ligan-targeted liposomal anticancer drugs", Pergamon, Progress in Lipid Research, 42:439-462 (2003).
Sweetman, "Entry for Docetaxel", Martindale:the complete drug reference, 33rd ed., p. 534 (2002).
Tobio, et al.,"Stealth PLA-PEG nanoparticlea as protein carriera for nasal administration", Pharm. Res., 15(2):270-75 (1998).
Yamamoto, et al., "Long-circulation Poly(ethylene glycol)-poly(D,L-lactide) block copolymermicelles with modulated surace chane", J Contl Rel., 77:27-38 (2001).
Cerchia, et al. "Neutralizing aptamers from whole-cell SELEX inhibit the RET receptor tyrosine kinase", PLoS Biology, 3(4):849-60 (2005).
Wu, et al., Selection of oligonucleotide apatamers with enhanced uptake and activation of human leukemia B cells,, Human Gene., 14:849-860 (2003).
Astete and Sabliov, "Synthesis and characterization of PLGA nanoparticles", J. Biomat. Sci.,-Polymer Ed., 17:247-289 (2006).
Balenga, et al., "Protective efficiency of dendrosomes as novel nano-sized adjuvants for DNA vaccination against birch pollen allergy", J Biotech., 123 (3):602-14 (2006).
Beck, et al., "A New Long-acting Injectable Microcapsule System for the Administration of Progesterone," Fertil. & Steril., 31(5):545-55 (1979).
Benita, et al., "Characterization of Drug-Loaded Poly(d,/-lactide) Microspheres," J. Pharm. Sci. 73(12):1721-24 (1984).
Ch'Ng, et al., "Bioadhesive Polymers as Platforms for Oral Controlled Drug Delivery II: Synthesis and Evaluation of Some Swelling, Water-insoluble Bioadhesive Polymers," J. Pharm. Sci. 74: 399-405 (1988).
Chickering & Mathiowitz, "Bioadhesive microspheres: i. A novel electrobalance-based method to study adhesive interactions between individual microspheres and intestinal mucosa," J. Control. Release 34:251-62 (1995).
Duchene, et al., "Pharmaceutical and Medical Aspects of Bioadhesive Systems for Drug Administration," Drug Development &. Ind. Pharm. 14(2&3):283-31 (1988).
Farokhzad, et al., "Cancer nanotechnology: drug encapsulated nanoparticle-aptmer bioconjugates for targeted delivery to prostate cancer cells", 13th Eu. Cancer Conf., Oct. 30-Nov. 3, Paris France (2005).
Gurney, et al., "Bioadhesive intraoral release systems: design, testing and analysis," Biomaterials 5:336-40 (1984).
Hamdy, et al., "Co-delivery of cancer-associated antigen and toll-like receptor 4 ligand in PLGA nanoparticles induces potent CD8+ T cell-mediated anti-tumor immunity", Vaccine, 26(39):5046-57 (2008).
Hong, et al., "Enhanced and prolonged cross-presentation following endosomal escape of exogenous antigens encapdulated in biodegradable nanoparticles", Immunol., 117(1):78-88 (2006).
Hotter, et al., "Targeting of a B7-1 (CD80) immunoglobulin G fusion protein to acute myeloid leukemia blasts increases their costimulatory activity for autologous remission T cells.", Blood, 97(10):3138-3145 (2001).
Huang et al., "Microencapsulation of Chlorpheniramine Maleate-Resin Particles with Crosslinked Chitosan for Sustained Release", Pharmaceutical Development and Technology, 4 1:107-115 (1999).
Igaku, "Intracellular trafficking of lipid antigens and their immune recognition by the CD1 system", Exp. Med., 24(7):936-40 (2006).
Illum, "Bioadhesive Microspheres as Potential Nasal Drug Delivery System," Int'l J. Pharm. 39: 189-99 (1987).
Labat-Robert & Decaens, "Glycoproteines du mucus gastrique: structure, fonctions et pathologie," Pathologie Biologie 24:241 (Paris 1979).
Lee, et al. "Adaptations of Nanoscale Viruses and Other Protein Cages for Medical Applications" Nanomedicine-Nanotechnology Biology and Medicine, 2 (3):137-149 (2006).
Lehr, et al., "In vitro evaluation of mucoadhesive properties of chitosan and some other natural polymers," International J. Pharmaceutics 78: 43-48 (1992).
Lehr, et al., "Intestinal transit of bioadhesive microspheres in an in situ loop in the rat—a comparative study with copolymers and blends based on poly(acrylic acid)," J. Controlled Rel. 13:51-62 (1990).
Leon-Bay, et al., "Microsphere formation and drug delivery in a series of derivatized amino acids," Winter conference of Medicinal Chemistry (Steamboat Springs, Colarodo 1995).
Martinez-Pomares, et al., "Fc chimeric protein containing the cysteine-rich domain of the murine mannose receptor binds to macrophages from splenic marginal zone and lymph node subcapsular sinus and to germinal centers", J Experimental Med., 184(5):1927-37 (1996).
Mathiowitz, et al., "Morphology of polyanhydride microsphere delivery systems," Scanning Microscopy 4(2):329-340 (1990).
Mikos, et al., "Interaction of Polymer Microspheres with Mucin Gels as a Means of Characterizing Polymer Retention on Mucus," J. Colloid & Interface Sci. 143 (2):366-73 (1991).
Raghuvanshi, et al., "Improved immune response from biodegradable polymer particles entrapping tetanus toxoid by use of different immunization protocol and adjuvants", Int J Pharm., 245(1-2):109-21 (2002).
Scawen, et al., "The Action of Proteolytic Enzymes on the Glycoprotein from Pig Gastric Mucus," Biochemical J. 163:363-68 (1977).
Smart, et al., "An in vitro investigation of mucosa-adhesive materials for use in controlled drug delivery," J. Pharm. & Pharmacol. 36:295-99 (1984).
Spiro, "Glycoproteins," Annual Review of Biochemistry 39:599-638 (Snell, ed. 1970).
Surgery Frontier, "What's new in surgery frontier", 13(3):290-3 (2006).
Walter, et al., "Hydrophillic poly (DL-lactide-co-glycolide) microspheres for the delivery of DNA to human-derived macrophages and dendritic cells", J Control Release, 76(1-2):149-68 (2001).
Yang, et al., "Micelles formed by self-assmbling of polylactide(ethylene glycol) block copolymers in aqueous solutions", J Colloid Interfac Si., 314:470-77 (2007).
Akagi, et al., "Multifunctional conjugation of proteins on/into bio-nanoparticles prepared by amphiphilic poly(gamma-glutamic acid)", J Biomat Sci Polym Ed., 17 (8):875-92 (2006).
Akagi, et al., "Development of vaccine adjuvants using polymeric nanoparticles and their potential applications for anti-HIV vaccine", Yakugaku Zasshi, 127(2):307-17 (2007) English Abstract.
Argov-Argaman, et al., "Lactosomes: Structural and compositional classification of unique nanometer-sized protein lipid particles of human milk", J Agric Food Chem., 58:11234-42 (2010).
Chu, et al, "Aptamer:toxin conjugates that specifically target prostate tumor cells", Cancer Res., 66:5989-92 (2006).
Elamanchili, et al., "Pathogen-mimicking nanoparticles or vaccine delivery to dendritic cells", J Cont. Rel., 30(4):378-95 (2007).

(56) References Cited

OTHER PUBLICATIONS

Gorelik, et al., "Scanning surface confocal microscopy for simultaneous topographical and fluorescence imaging: application to single virus-like particle entry into a cell", PNAS, 99(25):16018-23 (2002).

Harris, et al., "Proteolytic actuation o nanoparticle self-assembly", Angewandte Chemie, 118:3233-7 (2006).

Jayaprakash, et al., "Design and synthesis of a PSMA inhibitor-doxorubicin conjugate for targeted prostate cancer therapy", Chem Med Chem., 1:299-302 (2006).

Kawamura, et al., "Dendritic cells that endocytosed antigen-containing IgG-liposomes elicit effective antitumor immunity", J Immunother., 29(2):165-74 (2006).

Koenig, et al., "Immunologic factors in human milk: the effects of gestational age and pasteurization", J Human Lactation, 21:439-43 (2002).

Lamalle-Bernard, et al., "Coadsorption of HIV-1 p24 and gp120 proteins to surfactant-free anionic PLA nanoparticles preserves antigenicity and immunogenicity", J Control Rel., 115(1):57-67 (2006).

Martin, et al., "Crystal structure at 2.8 A of an FcRn/heterodimeric Fc complex: mechanism of pH-dependent binding.", Mol Cell, 7:867-77 (2001).

Matsuo, et al., "Efficient generation of antigen-specific cellular immunity by vaccination with poly (gamma-glutamic acid) nanoparticles entrapping endoplasmic reticulum-targeted peptides", Biochem Biophys Res Commun., 362:1069-72 (2007).

McNeil, "Nanotechnology for the biologist", J Leukoc Biol., 78:575-94 (2005).

Moon, et al., "Engineering Nano- and microparticles to tune immunity", Adv Mater., DOI:10.1002/adma.201200446 (2012).

Oyewumi, et al., "Nano-microparticles as immune adjuvants: correlating particle sizes and the resultant immune responses", Exp Rev Vaccines, 9(9):1095-1107 (2010).

Riley, et al., "Colloidal stability and drug incorporation aspects of micellar-like PLA-PEG nanoparticles", Colloids Surfaces B Biointerfaces, 16:147-59 (1999).

Riley, et al., "Physicochemical evaluation of nanoparticles assembled from Poly(lactic acid)-Poly(ethylene glycol) (PLA_PEG) block copolymers as drug delivery vehicles", Langmuir, 17:3168-74 (2001).

Shields, et al., "High resolution mapping of the binding site on human IgG1 for Fc gamma RI, Fc gamma RII, Fc gamma RIII, and FcRn and design of IgG1 variants with improved binding to the Fc gamma R", J Biolo Chem., 276(9):6591-6604 (2001).

Shim, "One target different effects: a comparison of distinct therapeutic antibodies against the same targets", Exp Mole Med.,43(10):539-49 (2011).

Suzuki, et al., "Development of effective antigen delivery carrier to dendritic cells via Fc receptor in cancer immunotherapy",Yakugaku Zasshi, 127(2):301-6 (2007). English Abstract.

Taylor, et al., "Development of a specific system for targeting protein to metallophilic macrophages", PNAS, 101(7):1963-8 (2004).

Uto, et al., "Targeting of antigen to dendritic cells with poly(gamma-glutamic acid) nanoparticles induces antigen-specific humoral and cellular immunity", J Immunology, 178 (5):2979-86 (2007).

Wakita, et al., "An indispensable role of type-1 IFNs for inducing CTL-mediated complete eradication of established tumor tissue by CpG-liposome co-encapsulated with model tumor antigen", Int. Immunol., 18(3):425-34 (2006).

Yu, et al., "Engineered bio-nanocapsules, the selective vector for drug delivery system", IUBMB Like, 58(1):1-6 (2006).

* cited by examiner

Mean Nanoparticle Size (nm)

ID

SEQUENCE LISTING

```
<160> NUMBER OF SEQ ID NOS: 9

<210> SEQ ID NO 1
<211> LENGTH: 71
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1
gggaggacga ugcggaucag ccauguuuac gucacuccuu gucaauccuc aucggcagac    60
gacucgcccg a                                                         71

<210> SEQ ID NO 2
<211> LENGTH: 70
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 2
```

```
gggaggacga ugcggaccga aaaagaccug acuucuauac uaagucuacg uucccagacg    60
acucgcccga                                                           70
```

```
<210> SEQ ID NO 3
<211> LENGTH: 57
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (57)
<223> OTHER INFORMATION: 3' inverted T cap

<400> SEQUENCE: 3
```

```
gggaggacga ugcggaucag ccauguuuac gucacuccuu gucaauccuc aucggct       57
```

```
<210> SEQ ID NO 4
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4
```

Ala Thr Trp Leu Pro Pro Arg
  1               5

```
<210> SEQ ID NO 5
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5
```

Ala Cys Asp Cys Arg Gly Asp Cys Phe Cys Gly
  1               5                  10

```
<210> SEQ ID NO 6
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6
```

Cys Asn Gly Arg Cys
  1               5

```
<210> SEQ ID NO 7
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7
```

His Trp Gly Phe
  1

```
<210> SEQ ID NO 8
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Cys Thr Thr His Trp Gly Phe Thr Leu Cys
 1               5                  10

<210> SEQ ID NO 9
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Cys Gly Asn Lys Arg Thr Arg Gly Cys
 1               5
```

SYSTEM FOR TARGETED DELIVERY OF THERAPEUTIC AGENTS

The present application is a continuation of PCT Application No. PCT/US2007/007927, filed on Mar. 30, 2007, which also is related to and claims priority under 35 U.S.C. §119(e) to United States provisional patent application U.S. Ser. No. 60/788,532, filed Mar. 31, 2006 (the '532 application). The entire contents of these applications are incorporated herein by reference.

This invention was made with government support under grant number U54 CA119349 awarded by the National Institutes of Health. The government has certain rights in this invention.

BACKGROUND OF THE INVENTION

Cancer is the second leading cause of death in the United States. Over one million people develop cancer each year, and approximately half of all men and one third of all women in the United States will develop cancer during their lifetimes.

Prostate cancer is the second most common type of cancer found in American men (after skin cancer), and the second-leading cause of cancer death (after lung cancer). The American Cancer Society (ACS) estimates that 1 in 6 men will develop prostate cancer in his lifetime and 1 in 34 men will die of the disease. The ACS further estimates that there will be about 218,890 new cases of prostate cancer and about 27,050 deaths attributable to prostate cancer in the United States in 2007.

Most cancers, including prostate cancer, are frequently treated by a combination of approaches, including surgical removal of a tumor, chemotherapy, and/or radiation therapy. Surgical procedures are usually not sufficient to remove a tumor in its entirety, so surgery is frequently accompanied by chemotherapy and/or radiation therapy. Chemotherapy involves the use of drugs to kill tumor cells, and radiation therapy involves treatment with high-energy rays (e.g. x-rays) to kill or shrink tumor cells.

Unfortunately, however, chemotherapy and radiation cause serious and sometimes life-threatening side effects, including fatigue; nausea; vomiting; pain; hair loss; anemia; central nervous system problems; infection; blood clotting problems; mouth, gum, and throat problems; diarrhea; constipation; nerve and muscle effects; kidney and bladder effects; flu-like symptoms; fluid retention; and effects on sexual organs.

Chemotherapy causes such severe side effects because the treatment involves the systemic administration of cytotoxic agents to a patient. These agents cannot distinguish tumor cells from normal cells and, therefore, kill healthy cells as well as tumor cells. Side effects are worsened because a very large dose must be administered to the patient in order to deliver a therapeutically effective dose to a tumor site. Although radiation therapy is administered somewhat more locally than chemotherapy, radiation treatment still results in the destruction of normal tissue in the vicinity of the tumor.

Thus, targeting of a therapeutic agent (e.g., to a particular tissue or cell type; to a specific diseased tissue but not to normal tissue; etc.) is desirable in the treatment of tissue specific diseases such as cancer (e.g. prostate cancer). For example, in contrast to systemic delivery of a cytotoxic anti-cancer agent, targeted delivery could prevent the agent from killing healthy cells. Additionally, targeted delivery would allow for the administration of a lower dose of the agent, which could reduce the undesirable side effects commonly associated with traditional chemotherapy.

Therefore, there is a strong need in the art for systems for selectively delivering therapeutic agents to desired tissues or cells. There is a further need for systems for targeting the delivery of cytotoxic anti-cancer agents to tumors, such as tumors associated with prostate cancer. The ability to control the precise level and location of a therapeutic agent in a patient would allow doses to be reduced, minimize side effects, and open new avenues for "personalized" therapy.

SUMMARY OF THE INVENTION

The present invention provides systems for selectively delivering therapeutic agents to particular organs, tissues, cells, and/or intracellular compartments. In certain embodiments, therapeutic agents are to be specifically delivered to diseased tissues. In certain specific embodiments, therapeutic agents are to be specifically delivered to tumors (e.g. malignant tumors or benign tumors). In specific embodiments, therapeutic agents are to be delivered to tumors associated with prostate cancer.

The present invention provides targeted particles comprising a particle, one or more targeting moieties, and one or more therapeutic agents to be delivered to an organ, tissue, cell, and/or intracellular compartment. In general, the cell is associated with a target which is able to specifically bind to the targeting moiety. The therapeutic agent is able to be delivered to the particular targeted organ, tissue, cell, and/or intracellular compartment once the target specifically binds to the targeting moiety.

Any particle can be used in accordance with the targeted particles of the present invention. In some embodiments, particles are biodegradable and biocompatible. In general, a substance is considered to be biocompatible if its addition to cells does not induce adverse effects. In general, a biodegradable substance is one that can be broken down under physiological conditions.

In general, a particle in accordance with the present invention is any entity having a greatest dimension (e.g. diameter) of less than 100 microns (μm). In some embodiments, inventive particles have a greatest dimension of less than 10 μm. In some embodiments, inventive particles have a greatest dimension of less than 1000 nanometers (nm). In some embodiments, inventive particles have a greatest dimension of less than 900 nm, 800 nm, 700 nm, 600 nm, 500 nm, 400 nm, 300 nm, 200 nm, or 100 nm.

In some embodiments, particles are spheres, spheroids, flat, plate-shaped, cubes, cuboids, ovals, ellipses, cylinders, cones, or pyramids. In some embodiments, particles are microparticles (e.g. microspheres). In some embodiments, particles are nanoparticles (e.g. nanospheres). In some embodiments, particles are liposomes. In some embodiments, particles are micelles. Particles can be solid or hollow and can comprise one or more layers (e.g., nanoshells, nanorings).

In some embodiments, particles can comprise a matrix of polymers. In some embodiments, a therapeutic agent to be delivered and/or targeting moiety can be associated with the surface of, encapsulated within, surrounded by, and/or dispersed throughout a polymeric matrix.

In some embodiments, a polymeric matrix can comprise polyethylenes, polycarbonates, polyanhydrides, polyhydroxyacids, polypropylfumerates, polycaprolactones, polyamides, polyacetals, polyethers, polyesters, poly(orthoesters), polycyanoacrylates, polyvinyl alcohols, polyurethanes, polyphosphazenes, polyacrylates, polymethacrylates, polyureas, polystyrenes, and/or polyamines. In some embodiments, a polymeric matrix may comprise poly(lactic-co-glycolic acid)

(PLGA), polyethylene glycol (PEG), and/or copolymers thereof. In some embodiments, a polymeric matrix can comprise dendrimers, proteins, carbohydrates, and/or nucleic acids.

In some embodiments, particles can be non-polymeric particles (e.g. metal particles, quantum dots, ceramics, inorganic materials, bone, etc.). In some embodiments, a therapeutic agent and/or targeting moiety can be covalently associated with a non-polymeric particle. In some embodiments, a therapeutic agent and/or targeting moiety can be non-covalently associated with a non-polymeric particle. In some embodiments, a therapeutic agent and/or targeting moiety can be associated with the surface of, encapsulated within, surrounded by, and/or dispersed throughout a non-polymeric polymer.

In some embodiments, particles may optionally comprise one or more surfactants, sugars, lipids, or release-retarding ingredients.

In certain embodiments, targeted particles in accordance with the present invention comprise a targeting moiety which specifically binds to one or more targets associated with an organ, tissue, cell, extracellular matrix, and/or intracellular compartment. As used herein, the terms "target" and "marker" can be used interchangeably.

A targeting moiety may be a nucleic acid (e.g. aptamer), polypeptide (e.g. antibody), glycoprotein, small molecule, carbohydrate, lipid, etc. For example, a targeting moiety can be an aptamer, which is generally an oligonucleotide (e.g., DNA, RNA, or an analog or derivative thereof) that binds to a particular target, such as a polypeptide. In general, the targeting function of the aptamer is based on the three-dimensional structure of the aptamer. In some embodiments, a targeting moiety is a polypeptide (e.g. an antibody that specifically recognizes a tumor marker).

In some embodiments, a target may be a marker that is exclusively or primarily associated with one or a few tissue types, with one or a few cell types, with one or a few diseases, and/or with one or a few developmental stages. In some embodiments, a target can comprise a protein (e.g. cell surface receptor, transmembrane protein, etc.), a carbohydrate (e.g. glycan moiety, glycocalyx, etc.), a lipid (e.g. steroid, phospholipid, etc.), and/or a nucleic acid (e.g. DNA, RNA, etc.)

In some embodiments, a target (i.e. marker) is a molecule that is present exclusively or in higher amounts on a malignant cell, e.g., a tumor antigen. In some embodiments, a marker is a prostate cancer marker. In certain embodiments, the prostate cancer marker is prostate specific membrane antigen (PSMA), a 100 kDa transmembrane glycoprotein that is expressed in most prostatic tissues, but is more highly expressed in prostatic cancer tissue than in normal tissue.

The present invention provides methods for designing novel targeting moieties. The present invention further provides methods for isolating or identifying novel targeting moieties from a mixture of candidate targeting moieties. Nucleic acid targeting moieties (e.g. aptamers) may be designed and/or identified using any available method, including SELEX and PICO, as described herein.

According to the present invention, any agents, including, for example, therapeutic agents (e.g. anti-cancer agents), diagnostic agents (e.g. contrast agents; radionuclides; and fluorescent, luminescent, and magnetic moieties), prophylactic agents (e.g. vaccines), and/or nutraceutical agents (e.g. vitamins, minerals, etc.) may be delivered. Exemplary agents to be delivered in accordance with the present invention include, but are not limited to, small molecules (e.g. cytotoxic agents), nucleic acids (e.g. RNAi agents), proteins (e.g. antibodies), lipids, carbohydrates, hormones, metals, radioactive elements and compounds, drugs, vaccines, immunological agents, etc., and/or combinations thereof. In some embodiments, the agent to be delivered is an agent useful in the treatment of cancer (e.g. prostate cancer).

In some embodiments, the agent to be delivered may be a mixture of pharmaceutically active agents. In some embodiments, the agent to be delivered may be a mixture of anti-cancer agents. In some embodiments, inventive targeted particles are administered in combination with one or more of the anti-cancer agents described herein.

Inventive targeted particles may be manufactured using any available method which does not interfere with the targeting function of the targeting moiety. In some embodiments, targeting moieties and/or therapeutic agents are covalently associated with a particle, and release and delivery of the therapeutic agent to a target site occurs by disrupting the association. In some embodiments, targeting moieties and/or therapeutic agents are not covalently associated with a particle. For example, particles may comprise a polymeric matrix, and therapeutic agents may be associated with the surface of, encapsulated within, and/or distributed throughout the polymeric matrix. Therapeutic agents can be released by diffusion, degradation of the particle, and/or combination thereof.

Physical association can be achieved in a variety of different ways. Physical association may be covalent or non-covalent and may or may not involve a cross-linking step. The particle, targeting moiety, and/or therapeutic agent may be directly associated with one another, e.g., by one or more covalent bonds, or the association may be mediated by one or more linkers. In some embodiments, a linker is a cleavable linker. In some embodiments, a linker is an aliphatic or heteroaliphatic linker. In some embodiments, the linker is a polyalkyl linker. In certain embodiments, the linker is a polyether linker. In certain embodiments, the linker is a polyethylene linker. In certain specific embodiments, the linker is a polyethylene glycol (PEG) linker.

In some embodiments, targeted particles in accordance with the present invention may be used to treat, alleviate, ameliorate, relieve, delay onset of, inhibit progression of, reduce severity of, and/or reduce incidence of one or more symptoms or features of a disease, disorder, and/or condition. In some embodiments, inventive targeted particles may be used to treat cancer. In certain embodiments, inventive targeted particles may be used to treat prostate cancer. The compositions, according to the method of the present invention, may be administered using any amount and any route of administration effective for treatment.

In some embodiments, targeted particles of the present invention may be used to diagnose a disease, disorder, and/or condition. In some embodiments, inventive targeted particles may be used to diagnose cancer. In certain embodiments, inventive targeted particles may be used to diagnose prostate cancer. In some embodiments, such methods of diagnosis may involve the use of inventive targeted particles to physically detect and/or locate a tumor within the body of a subject. In some embodiments, inventive targeted particles comprise particles which have intrinsically detectable properties (e.g. magnetic particles). In some embodiments, inventive targeted particles comprise particles which do not have intrinsically detectable properties but are associated with a substance which is detectable (e.g. fluorescent or radioactive moiety).

The present invention provides kits useful for carrying out various aspects of the invention. In some embodiments, a kit may include, for example, (i) a targeted particle comprising a particle, a targeting moiety, and one or more particular therapeutic agents to be delivered; and (ii) instructions for administering the targeted particle to a subject in need thereof. In some embodiments, a kit may be provided which includes materials useful for identifying and/or screening for novel targeting moieties. Such a kit may include, for example, (i) a targeted particle comprising a particle, a library of targeting moieties, and one or more therapeutic agents to be delivered; (ii) a targeted particle that may serve as a positive control; and (iii) a targeted particle that may serve as a negative control.

This application refers to various issued patents, published patent applications, journal articles, and other publications, all of which are incorporated herein by reference.

DEFINITIONS

Figure 1:
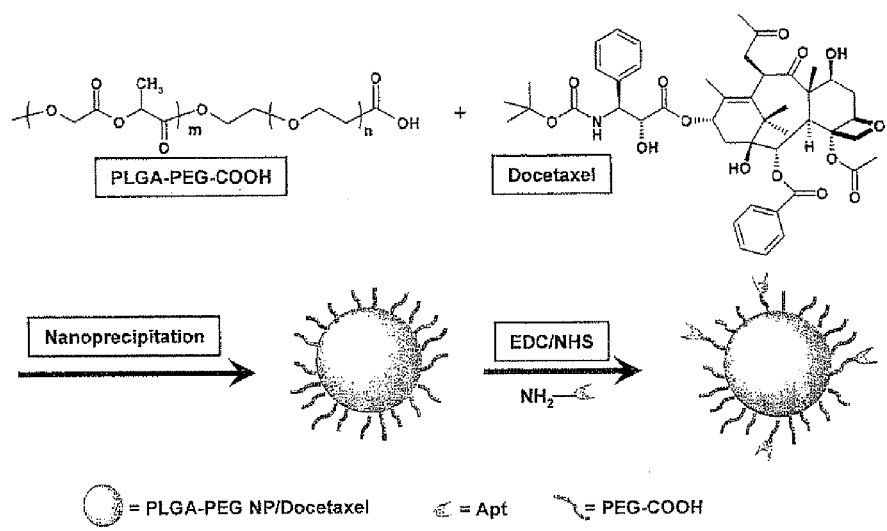
FIG. 1: Synthesis of PLGA-b-PEG-COOH nanoparticles (NP), and association of aptamer to nanoparticles. Docetaxel was encapsulated within PLGA-b-PEG-COOH NP using the nanoprecipitation method. PLGA-PEG NP/Docetaxel was covalently associated with amine-terminated A10 prostate-specific membrane antigen (PSMA) aptamer (Apt) in the presence of EDC.

Amino acid: As used herein, term "amino acid," in its broadest sense, refers to any compound and/or substance that can be incorporated into a polypeptide chain. In some embodiments, an amino acid has the general structure H$_2$N—C(H)(R)—COOH. In some embodiments, an amino acid is a naturally-occurring amino acid. In some embodiments, an amino acid is a synthetic amino acid; in some embodiments, an amino acid is a D-amino acid; in some embodiments, an amino acid is an L-amino acid. "Standard amino acid" or "natural amino acid" refers to any of the twenty standard L-amino acids commonly found in naturally occurring peptides. "Nonstandard amino acid" refers to any amino acid, other than the standard amino acids, regardless of whether it is prepared synthetically or obtained from a natural source. As used herein, "non-natural amino acid" encompasses chemically produced or modified amino acids, including but not limited to salts, amino acid derivatives (such as amides), and/or substitutions. Amino acids, including carboxy- and/or amino-terminal amino acids in peptides, can be modified by methylation, amidation, acetylation, and/or substitution with other chemical groups that can change the peptide's circulating half-life without adversely affecting their activity. Amino acids may participate in a disulfide bond. The term "amino acid" is used interchangeably with "amino acid residue," and may refer to a free amino acid and/or to an amino acid residue of a peptide. It will be apparent from the context in which the term is used whether it refers to a free amino acid or a residue of a peptide.

Animal: As used herein, the term "animal" refers to any member of the animal kingdom. In some embodiments, "animal" refers to humans, at any stage of development. In some embodiments, "animal" refers to non-human animals, at any stage of development. In certain embodiments, the non-human animal is a mammal (e.g., a rodent, a mouse, a rat, a rabbit, a monkey, a dog, a cat, a sheep, cattle, a primate, and/or a pig). In some embodiments, animals include, but are not limited to, mammals, birds, reptiles, amphibians, fish, and/or worms. In some embodiments, an animal may be a transgenic animal, genetically-engineered animal, and/or a clone.

Antibody: As used herein, the term "antibody" refers to any immunoglobulin, whether natural or wholly or partially synthetically produced. All derivatives thereof which maintain specific binding ability are also included in the term. The term also covers any protein having a binding domain which is homologous or largely homologous to an immunoglobulin binding domain. Such proteins may be derived from natural sources, or partly or wholly synthetically produced. An antibody may be monoclonal or polyclonal. An antibody may be a member of any immunoglobulin class, including any of the human classes: IgG, IgM, IgA, IgD, and IgE. As used herein, the terms "antibody fragment" or "characteristic portion of an antibody" are used interchangeably and refer to any derivative of an antibody which is less than full-length. In general, an antibody fragment retains at least a significant portion of the full-length antibody's specific binding ability. Examples of antibody fragments include, but are not limited to, Fab, Fab', F(ab')2, scFv, Fv, dsFv diabody, and Fd fragments. An antibody fragment may be produced by any means. For example, an antibody fragment may be enzymatically or chemically produced by fragmentation of an intact antibody and/or it may be recombinantly produced from a gene encoding the partial antibody sequence. Alternatively or additionally, an antibody fragment may be wholly or partially synthetically produced. An antibody fragment may optionally comprise a single chain antibody fragment. Alternatively or additionally, an antibody fragment may comprise multiple chains which are linked together, for example, by disulfide linkages. An antibody fragment may optionally comprise a multimolecular complex. A functional antibody fragment will typically comprise at least about 50 amino acids and more typically will comprise at least about 200 amino acids.

Approximately: As used herein, the terms "approximately" or "about" in reference to a number are generally taken to include numbers that fall within a range of 5%, 10%, 15%, or 20% in either direction (greater than or less than) of the number unless otherwise stated or otherwise evident from the context (except where such number would be less than 0% or exceed 100% of a possible value).

Associated with: As used herein, the term "associated with" refers to the state of two or more entities which are linked by a direct or indirect covalent or non-covalent interaction. In some embodiments, an association is covalent. In some embodiments, a covalent association is mediated by a linker moiety. In some embodiments, an association is non-covalent (e.g. charge interactions, affinity interactions, metal coordination, physical adsorption, host-guest interactions, hydrophobic interactions, TT stacking interactions, hydrogen bonding interactions, van der Waals interactions, magnetic interactions, electrostatic interactions, dipole-dipole interactions, etc.). For example, in some embodiments, an entity (e.g. targeting moiety or therapeutic agent to be delivered) may be covalently associated with a particle. In some embodiments, an entity (e.g. targeting moiety or therapeutic agent to be delivered) may be non-covalently associated with a particle, (e.g. the entity may be associated with the surface of, encapsulated within, surrounded by, and/or distributed throughout a polymeric matrix of an inventive particle).

Biocompatible: As used herein, the term "biocompatible" refers to substances that are not toxic to cells. In some embodiments, a substance is considered to be "biocompatible" if its addition to cells in vitro results in less than or equal to approximately 20% cell death. In some embodiments, a substance is considered to be "biocompatible" if its addition to cells in vivo does not induce inflammation and/or other adverse effects in vivo.

Biodegradable: As used herein, the term "biodegradable" refers to substances that are degraded under physiological conditions. In some embodiments, a biodegradable substance is a substance that is broken down by cellular machinery. In some embodiments, a biodegradable substance is a substance that is broken down by chemical processes.

Cell type: As used herein, the term "cell type" refers to a form of cell having a distinct set of morphological, biochemical, and/or functional characteristics that define the cell type. One of skill in the art will recognize that a cell type can be defined with varying levels of specificity. For example, prostate endothelial cells and circulatory system endothelial cells are distinct cell types, which can be distinguished from one another but share certain features that are characteristic of the broader "endothelial" cell type of which both are members. Typically, cells of different types may be distinguished from one another based on their differential expression of a variety of genes which are referred to in the art as "markers" of a particular cell type or types (e.g., cell types of a particular lineage). A "cell type specific marker" is a gene product or modified version thereof that is expressed at a significantly greater level by one or more cell types than by all or most other cell types and whose expression is characteristic of that cell type. Many cell type specific markers are recognized as such in the art. Similarly, a "tissue specific marker" is one that is expressed at a significantly greater level by cells of a type that is characteristic of a particular tissue than by cells that are characteristic of most or all other tissues.

Characteristic portion: As used herein, the phrase a "characteristic portion" of a substance, in the broadest sense, is one that shares some degree of sequence and/or structural identity and/or at least one functional characteristic with the relevant intact substance. For example, a "characteristic portion" of a polynucleotide is one that contains a continuous stretch of nucleotides, or a collection of continuous stretches of nucleotides, that together are characteristic of a polynucleotide. In some embodiments, each such continuous stretch generally will contain at least 2, 5, 10, 15, 20 or more nucleotides. In some embodiments, the characteristic portion may be biologically active.

Gene: As used herein, the term "gene" has its meaning as understood in the art. It will be appreciated by those of ordinary skill in the art that the term "gene" may include gene regulatory sequences (e.g., promoters, enhancers, etc.) and/or intron sequences. It will further be appreciated that definitions of gene include references to nucleic acids that do not encode proteins but rather encode RNA molecules (e.g., functional RNA molecules, such as rRNAs and/or tRNAs).

Gene product or expression product: As used herein, the term "gene product" or "expression product" generally refers to an RNA transcribed from the gene (pre- and/or post-processing) or a polypeptide (pre- and/or post-modification) encoded by an RNA transcribed from the gene.

Homology: As used herein, the term "homology" refers to to the overall relatedness between polymeric molecules, e.g. between nucleic acid molecules (e.g. DNA molecules and/or RNA molecules) and/or between polypeptide molecules. In some embodiments, polymeric molecules are considered to be "homologous" to one another if their sequences are at least 25%, 30%, 35%, 40%, 45%, 50%, 55%, 60%, 65%, 70%, 75%, 80%, 85%, 90%, 95%, or 99% identical. In some embodiments, polymeric molecules are considered to be "homologous" to one another if their sequences are at least 25%, 30%, 35%, 40%, 45%, 50%, 55%, 60%, 65%, 70%, 75%, 80%, 85%, 90%, 95%, or 99% similar.

Identity: As used herein, the term "identity" refers to the overall relatedness between polymeric molecules, e.g. between nucleic acid molecules (e.g. DNA molecules and/or RNA molecules) and/or between polypeptide molecules. Calculation of the percent identity of two nucleic acid sequences, for example, can be performed by aligning the two sequences for optimal comparison purposes (e.g., gaps can be introduced in one or both of a first and a second nucleic acid sequences for optimal alignment and non-identical sequences can be disregarded for comparison purposes). In certain embodiments, the length of a sequence aligned for comparison purposes is at least 30%, at least 40%, at least 50%, at least 60%, at least 70%, at least 80%, at least 90%, at least 95% or 100% of the length of the reference sequence. The nucleotides at corresponding nucleotide positions are then compared. When a position in the first sequence is occupied by the same nucleotide as the corresponding position in the second sequence, then the molecules are identical at that position. The percent identity between the two sequences is a function of the number of identical positions shared by the sequences, taking into account the number of gaps, and the length of each gap, which needs to be introduced for optimal alignment of the two sequences. The comparison of sequences and determination of percent identity between two sequences can be accomplished using a mathematical algorithm. For example, the percent identity between two nucleotide sequences can be determined using the algorithm of Meyers and Miller (CABIOS, 1989, 4: 11-17), which has been incorporated into the ALIGN program (version 2.0) using a PAM120 weight residue table, a gap length penalty of 12 and a gap penalty of 4. The percent identity between two nucleotide sequences can, alternatively, be determined using the GAP program in the GCG software package using a NWSgapdna.CMP matrix.

In vitro: As used herein, the term "in vitro" refers to events that occur in an artificial environment, e.g., in a test tube or reaction vessel, in cell culture, etc., rather than within an organism (e.g. animal, plant, and/or microbe).

In vivo: As used herein, the term "in vivo" refers to events that occur within an organism (e.g. animal, plant, and/or microbe).

Nucleic acid: As used herein, the term "nucleic acid," in its broadest sense, refers to any compound and/or substance that can be incorporated into an oligonucleotide chain. As used herein, the terms "nucleic acid" and "polynucleotide" can be used interchangeably. In some embodiments, "nucleic acid" encompasses RNA as well as single and/or double-stranded DNA and/or cDNA. Furthermore, the terms "nucleic acid," "DNA," "RNA," and/or similar terms include nucleic acid analogs, i.e. analogs having other than a phosphodiester backbone. For example, the so-called "peptide nucleic acids," which are known in the art and have peptide bonds instead of phosphodiester bonds in the backbone, are considered within the scope of the present invention. The term "nucleotide sequence encoding an amino acid sequence" includes all nucleotide sequences that are degenerate versions of each other and/or encode the same amino acid sequence. Nucleotide sequences that encode proteins and/or RNA may include introns. Nucleic acids can be purified from natural sources, produced using recombinant expression systems and optionally purified, chemically synthesized, etc. Where appropriate, e.g., in the case of chemically synthesized molecules, nucleic acids can comprise nucleoside analogs such as analogs having chemically modified bases or sugars, backbone modifications, etc. The term "nucleic acid sequence" as used herein can refer to the nucleic acid material itself and is not restricted to the sequence information (e.g. the succession of letters chosen, for example, among the five base letters A, G, C, T, or U) that biochemically characterizes a specific nucleic acid, e.g., a DNA or RNA molecule. A nucleic acid sequence is presented in the 5' to 3' direction unless otherwise indicated. The term "nucleic acid segment" is used herein to refer to a nucleic acid sequence that is a portion of a longer nucleic acid sequence. In some embodiments, a "nucleic acid" or "polynucleotide" comprises natural nucleosides (e.g. adenosine, thymidine, guanosine, cytidine, uridine, deoxyadenosine, deoxythymidine, deoxyguanosine, and deoxycytidine); nucleoside analogs (e.g., 2-aminoadenosine, 2-thiothymidine, inosine, pyrrolo-pyrimidine, 3-methyl adenosine, 5-methylcytidine, C-5 propynyl-cytidine, C-5 propynyl-uridine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, O(6)-methylguanine, and 2-thiocytidine); chemically modified bases; biologically modified bases (e.g., methylated bases); intercalated bases; modified sugars (e.g., 2'-fluororibose, ribose, 2'-deoxyribose, arabinose, and hexose); and/or modified phosphate groups (e.g., phosphorothioates and 5'-N-phosphoramidite linkages).

Particle: As used herein, a "particle" refers to any entity having a diameter of less than 100 microns (μm). Typically, particles have a longest dimension (e.g. diameter) of 1000 nm or less. In some embodiments, particles have a diameter of 300 nm or less. In some embodiments, nanoparticles have a diameter of 200 nm or less. In some embodiments, nanoparticles have a diameter of 100 nm or less. In general, particles are greater in size than the renal excretion limit, but are small enough to avoid accumulation in the liver. In some embodiments, a population of particles may be relatively uniform in terms of size, shape, and/or composition. In general, inventive particles are biodegradable and/or biocompatible. Inventive particles can be solid or hollow and can comprise one or more layers. In some embodiments, particles are spheres, spheroids, flat, plate-shaped, cubes, cuboids, ovals, ellipses, cylinders, cones, or pyramids. In some embodiments, particles can be a matrix of polymers. In some embodiments, the matrix is cross-linked. In some embodiments, formation of the matrix involves a cross-linking step. In some embodiments, the matrix is not substantially cross-linked. In some embodiments, formation of the matrix does not involve a cross-linking step. In some embodiments, particles can be a non-polymeric particle (e.g. a metal particle, quantum dot, ceramic, inorganic material, bone, etc.). Inventive particles may be microparticles, nanoparticles, liposomes, and/or micelles. As used herein, the term "nanoparticle" refers to any particle having a diameter of less than 1000 nm.

Pure: As used herein, a substance and/or entity is "pure" if it is substantially free of other components. For example, a preparation that contains more than about 90% of a particular substance and/or entity is typically considered to be a pure preparation. In some embodiments, a substance and/or entity is at least 91%, 92%, 93%, 94%, 95%, 96%, 97%, 98%, or 99% pure.

Similarity: As used herein, the term "similarity" refers to the overall relatedness between polymeric molecules, e.g. between nucleic acid molecules (e.g. DNA molecules and/or RNA molecules) and/or between polypeptide molecules. Calculation of percent similarity of polymeric molecules to one another can be performed in the same manner as a calculation of percent identity, except that calculation of percent similarity takes into account conservative substitutions as is understood in the art.

Small molecule: In general, a "small molecule" is understood in the art to be an organic molecule that is less than about 2000 g/mol in size. In some embodiments, the small molecule is less than about 1500 g/mol or less than about 1000 g/mol. In some embodiments, the small molecule is less than about 800 g/mol or less than about 500 g/mol. In some embodiments, small molecules are non-polymeric and/or non-oligomeric. In some embodiments, small molecules are not proteins, peptides, or amino acids. In some embodiments, small molecules are not nucleic acids or nucleotides. In some embodiments, small molecules are not saccharides or polysaccharides.

Specific binding: As used herein, the term "specific binding" refers to non-covalent physical association of a first and a second moiety wherein the association between the first and second moieties is at least 10 times as strong, at least 50 times as strong, or at least 100 times as strong as the association of either moiety with most or all other moieties present in the environment in which binding occurs. Binding of two or more entities may be considered specific if the equilibrium dissociation constant, $K_d$, is $10^{-3}$ M or less, $10^{-4}$ M or less, $10^{-5}$ M or less, $10^{-6}$ M or less, $10^{-7}$ M or less, $10^{-8}$ M or less, $10^{-9}$ M or less, $10^{-10}$ M or less, $10^{-11}$ M or less, or $10^{-12}$ M or less under the conditions employed, e.g., under physiological conditions such as those inside a cell or consistent with cell survival. In some embodiments, specific binding can be accomplished by a plurality of weaker interactions (e.g. a plurality of individual interactions, wherein each individual interaction is characterized by a $K_d$ of greater than $10^{-3}$ M). In some embodiments, specific binding, which can be referred to as "molecular recognition," is a saturable binding interaction between two entities that is dependent on complementary orientation of functional groups on each entity. Examples of specific binding interactions include aptamer-aptamer target interactions, antibody-antigen interactions, avidin-biotin interactions, ligand-receptor interactions, metal-chelate interactions, hybridization between complementary nucleic acids, etc.

Subject: As used herein, the term "subject" or "patient" refers to any organism to which a composition of this invention may be administered, e.g., for experimental, diagnostic, and/or therapeutic purposes. Typical subjects include animals (e.g., mammals such as mice, rats, rabbits, non-human primates, and humans) and/or plants.

Suffering from: An individual who is "suffering from" a disease, disorder, and/or condition has been diagnosed with or displays one or more symptoms of the disease, disorder, and/or condition.

Susceptible to: An individual who is "susceptible to" a disease, disorder, and/or condition has not been diagnosed with and/or may not exhibit symptoms of the disease, disorder, and/or condition. In some embodiments, an individual who is susceptible to a disease, disorder, and/or condition (for example, cancer) may be characterized by one or more of the following: (1) a genetic mutation associated with development of the disease, disorder, and/or condition (e.g. a mutation in an oncogene-encoding gene); (2) a genetic polymorphism associated with development of the disease, disorder, and/or condition (e.g. a polymorphism in the promoter region of an oncogene-encoding gene); (3) increased and/or decreased expression and/or activity of a protein associated with the disease, disorder, and/or condition (e.g. overexpression of the EGF receptor or TGF-α); (4) habits and/or lifestyles associated with development of the disease, disorder, and/or condition (e.g. heavy smoking or obesity); (5) a family history of the disease, disorder, and/or condition (e.g. parent with cancer); (6) infection by a microbe associated with development of the disease, disorder, and/or condition (e.g. infection by a virus such as HPV). In some embodiments, an individual who is susceptible to a disease, disorder, and/or condition will develop the disease, disorder, and/or condition. In some embodiments, an individual who is susceptible to a disease, disorder, and/or condition will not develop the disease, disorder, and/or condition.

Target: As used herein, the term "target" or "marker" refers to any entity that is capable of specifically binding to a particular targeting moiety. In some embodiments, targets are specifically associated with one or more particular tissue types. In some embodiments, targets are specifically associated with one or more particular cell types. In some embodiments, targets are specifically associated with one or more particular disease states. In some embodiments, targets are specifically associated with one or more particular developmental stages. For example, a cell type specific marker is typically expressed at levels at least 2 fold greater in that cell type than in a reference population of cells. In some embodiments, the cell type specific marker is present at levels at least 3 fold, at least 4 fold, at least 5 fold, at least 6 fold, at least 7 fold, at least 8 fold, at least 9 fold, at least 10 fold, at least 50 fold, at least 100 fold, or at least 1000 fold greater than its average expression in a reference population. Detection or measurement of a cell type specific marker may make it possible to distinguish the cell type or types of interest from cells of many, most, or all other types. In some embodiments, a target can comprise a protein, a carbohydrate, a lipid, and/or a nucleic acid, as described herein.

Targeted: A substance is considered to be "targeted" for the purposes described herein if it specifically binds to a targeting moiety. In some embodiments, a targeting moiety specifically binds to a target under stringent conditions. An inventive targeted particle comprising a targeting moiety is considered to be "targeted" if the targeting moiety specifically binds to a target, thereby delivering the entire targeted particle composition to a specific organ, tissue, cell, and/or intracellular compartment.

Targeting moiety: As used herein, the term "targeting moiety" refers to any moiety that binds to a component associated with a cell. Such a component is referred to as a "target" or a "marker." A targeting moiety may be a polypeptide, glycoprotein, nucleic acid, small molecule, carbohydrate, lipid, etc. In some embodiments, a targeting moiety is an antibody or characteristic portion thereof. In some embodiments, a targeting moiety is a receptor or characteristic portion thereof. In some embodiments, a targeting moiety is a ligand or characteristic portion thereof. In some embodiments, a targeting moiety is a nucleic acid targeting moiety (e.g. an aptamer) that binds to a cell type specific marker. In general, an aptamer is an oligonucleotide (e.g., DNA, RNA, or an analog or derivative thereof) that specifically binds to a particular target, such as a polypeptide. In some embodiments, a targeting moiety is a small molecule.

Therapeutically effective amount: As used herein, the term "therapeutically effective amount" means an amount of a therapeutic and/or diagnostic agent (e.g., inventive targeted particle) that is sufficient, when administered to a subject suffering from or susceptible to a disease, disorder, and/or condition, to treat and/or diagnose the disease, disorder, and/or condition.

Therapeutic agent: As used herein, the phrase "therapeutic agent" refers to any agent that, when administered to a subject, has a therapeutic and/or diagnostic effect and/or elicits a desired biological and/or pharmacological effect.

Treating: As used herein, the term "treating" refers to partially or completely alleviating, ameliorating, relieving, delaying onset of, inhibiting progression of, reducing severity of, and/or reducing incidence of one or more symptoms or features of a particular disease, disorder, and/or condition. For example, "treating" cancer may refer to inhibiting survival, growth, and/or spread of a tumor. Treatment may be administered to a subject who does not exhibit signs of a disease, disorder, and/or condition and/or to a subject who exhibits only early signs of a disease, disorder, and/or condition for the purpose of decreasing the risk of developing pathology associated with the disease, disorder, and/or condition. In some embodiments, treatment comprises delivery of an inventive targeted particle to a subject.

DETAILED DESCRIPTION OF CERTAIN PREFERRED EMBODIMENTS OF THE INVENTION

The present invention provides systems for selectively delivering therapeutic agents to particular organs, tissues, cells, and/or intracellular compartments. In certain embodiments, therapeutic agents are to be specifically delivered to diseased tissues. In certain specific embodiments, therapeutic agents are to be specifically delivered to tumors (e.g. malignant tumors or benign tumors). In specific embodiments, therapeutic agents are to be delivered to tumors associated with cancer (e.g. prostate cancer).

The present invention provides targeted particles comprising a particle, one or more targeting moieties, and one or more therapeutic agents to be delivered to an organ, tissue, cell, and/or intracellular compartment. In general, the organ, tissue, cell, and/or intracellular compartment is associated with a target which is able to specifically bind to the targeting moiety. The therapeutic agent is able to be delivered to the particular targeted organ, tissue, cell, and/or intracellular compartment once the target specifically binds to the targeting moiety.

Particles

In general, targeted particles of the present invention comprise a particle. Any particle can be used in accordance with the present invention. In some embodiments, particles are biodegradable and biocompatible. In general, a biocompatible substance is not toxic to cells. In some embodiments, a substance is considered to be biocompatible if its addition to cells results in less than a certain threshhold of cell death. In some embodiments, a substance is considered to be biocompatible if its addition to cells does not induce adverse effects. In general, a biodegradable substance is one that undergoes breakdown under physiological conditions over the course of a therapeutically relevant time period (e.g., weeks, months, or years). In some embodiments, a biodegradable substance is a substance that can be broken down by cellular machinery. In some embodiments, a biodegradable substance is a substance that can be broken down by chemical processes. In some embodiments, a particle is a substance that is both biocompatible and biodegradable. In some embodiments, a particle is a substance that is biocompatible, but not biodegradable. In some embodiments, a particle is a substance that is biodegradable, but not biocompatible.

In some embodiments, a particle which is biocompatible and/or biodegradable may be associated with a therapeutic agent that is not biocompatible, is not biodegradable, or is neither biocompatible nor biodegradable (e.g. a cytotoxic agent). In some embodiments, a particle which is biocompatible and/or biodegradable may be associated with a therapeutic agent that is also biocompatible and/or biodegradable.

In general, a particle in accordance with the present invention is any entity having a greatest dimension (e.g. diameter) of less than 100 microns (μm). In some embodiments, inventive particles have a greatest dimension of less than 10 μm. In some embodiments, inventive particles have a greatest dimension of less than 1000 nanometers (nm). In some embodiments, inventive particles have a greatest dimension of less than 900 nm, 800 nm, 700 nm, 600 nm, 500 nm, 400 nm, 300 nm, 200 nm, or 100 nm. Typically, inventive particles have a greatest dimension (e.g., diameter) of 300 nm or less. In some embodiments, inventive particles have a greatest dimension (e.g., diameter) of 250 nm or less. In some embodiments, inventive particles have a greatest dimension (e.g., diameter) of 200 nm or less. In some embodiments, inventive particles have a greatest dimension (e.g., diameter) of 150 nm or less. In some embodiments, inventive particles have a greatest dimension (e.g., diameter) of 100 nm or less. Smaller particles, e.g., having a greatest dimension of 50 nm or less are used in some embodiments of the invention. In some embodiments, inventive particles have a greatest dimension ranging between 25 nm and 200 nm.

In some embodiments, particles have a diameter of approximately 1000 nm. In some embodiments, particles have a diameter of approximately 750 nm. In some embodiments, particles have a diameter of approximately 500 nm. In some embodiments, particles have a diameter of approximately 450 nm. In some embodiments, particles have a diameter of approximately 400 nm. In some embodiments, particles have a diameter of approximately 350 nm. In some embodiments, particles have a diameter of approximately 300 nm. In some embodiments, particles have a diameter of approximately 275 nm. In some embodiments, particles have a diameter of approximately 250 nm. In some embodiments, particles have a diameter of approximately 225 nm. In some embodiments, particles have a diameter of approximately 200 nm. In some embodiments, particles have a diameter of approximately 175 nm. In some embodiments, particles have a diameter of approximately 150 nm. In some embodiments, particles have a diameter of approximately 125 nm. In some embodiments, particles have a diameter of approximately 100 nm. In some embodiments, particles have a diameter of approximately 75 nm. In some embodiments, particles have a diameter of approximately 50 nm. In some embodiments, particles have a diameter of approximately 25 nm.

In certain embodiments, particles are greater in size than the renal excretion limit (e.g. particles having diameters of greater than 6 nm). In certain embodiments, particles are small enough to avoid clearance of particles from the bloodstream by the liver (e.g. particles having diameters of less than 1000 nm). In general, physiochemical features of particles should allow a targeted particle to circulate longer in plasma by decreasing renal excretion and liver clearance.

It is often desirable to use a population of particles that is relatively uniform in terms of size, shape, and/or composition so that each particle has similar properties. For example, at least 80%, at least 90%, or at least 95% of the particles may have a diameter or greatest dimension that falls within 5%, 10%, or 20% of the average diameter or greatest dimension. In some embodiments, a population of particles may be herogeneous with respect to size, shape, and/or composition.

Zeta potential is a measurement of surface potential of a particle. In some embodiments, particles have a zeta potential ranging between −50 mV and +50 mV. In some embodiments, particles have a zeta potential ranging between −25 mV and +25 mV. In some embodiments, particles have a zeta potential ranging between −10 mV and +10 mV. In some embodiments, particles have a zeta potential ranging between −5 mV and +5 mV. In some embodiments, particles have a zeta potential ranging between 0 mV and +50 mV. In some embodiments, particles have a zeta potential ranging between 0 mV and +25 mV. In some embodiments, particles have a zeta potential ranging between 0 mV and +10 mV. In some embodiments, particles have a zeta potential ranging between 0 mV and +5 mV. In some embodiments, particles have a zeta potential ranging between −50 mV and 0 mV. In some embodiments, particles have a zeta potential ranging between −25 mV and 0 mV. In some embodiments, particles have a zeta potential ranging between −10 mV and 0 mV. In some embodiments, particles have a zeta potential ranging between −5 mV and 0 mV. In some embodiments, particles have a substantially neutral zeta potential (i.e. approximately 0 mV).

A variety of different particles can be used in accordance with the present invention. In some embodiments, particles are spheres or spheroids. In some embodiments, particles are spheres or spheroids. In some embodiments, particles are flat or plate-shaped. In some embodiments, particles are cubes or cuboids. In some embodiments, particles are ovals or ellipses. In some embodiments, particles are cylinders, cones, or pyramids.

In some embodiments, particles are microparticles (e.g. microspheres). In general, a "microparticle" refers to any particle having a diameter of less than 1000 μm. In some embodiments, particles are nanoparticles (e.g. nanospheres). In general, a "nanoparticle" refers to any particle having a diameter of less than 1000 nm. In some embodiments, particles are picoparticles (e.g. picospheres). In general, a "picoparticle" refers to any particle having a diameter of less than 1 nm. In some embodiments, particles are liposomes. In some embodiments, particles are micelles.

Particles can be solid or hollow and can comprise one or more layers (e.g., nanoshells, nanorings). In some embodiments, each layer has a unique composition and unique properties relative to the other layer(s). To give but one example, particles may have a core/shell structure, wherein the core is one layer and the shell is a second layer. Particles may comprise a plurality of different layers. In some embodiments, one layer may be substantially cross-linked, a second layer is not substantially cross-linked, and so forth. In some embodiments, one, a few, or all of the different layers may comprise one or more therapeutic agents to be delivered. In some embodiments, one layer comprises a therapeutic agent to be delivered, a second layer does not comprise a therapeutic agent to be delivered, and so forth. In some embodiments, each individual layer comprises a different therapeutic agent or set of therapeutic agents to be delivered.

In certain embodiments of the invention, a particle is porous, by which is meant that the particle contains holes or channels, which are typically small compared with the size of a particle. For example a particle may be a porous silica particle, e.g., a mesoporous silica nanoparticle or may have a coating of mesoporous silica (Lin et al., 2005, *J. Am. Chem. Soc.,* 17:4570). Particles may have pores ranging from about 1 nm to about 50 nm in diameter, e.g., between about 1 and 20 nm in diameter. Between about 10% and 95% of the volume of a particle may consist of voids within the pores or channels.

Particles may have a coating layer. Use of a biocompatible coating layer can be advantageous, e.g., if the particles contain materials that are toxic to cells. Suitable coating materials include, but are not limited to, natural proteins such as bovine serum albumin (BSA), biocompaticle hydrophilic polymers such as polyethylene glycol (PEG) or a PEG derivative, phospholipid-(PEG), silica, lipids, polymers, carbohydrates such as dextran, other nanoparticles that can be associated with inventive nanoparticles etc. Coatings may be applied or assembled in a variety of ways such as by dipping, using a layer-by-layer technique, by self-assembly, conjugation, etc. Self-assembly refers to a process of spontaneous assembly of a higher order structure that relies on the natural attraction of the components of the higher order structure (e.g., molecules) for each other. It typically occurs through random movements of the molecules and formation of bonds based on size, shape, composition, or chemical properties.

In some embodiments, particles may optionally comprise one or more dispersion media, surfactants, or release-retarding ingredients. In some embodiments, particles may optionally comprise one or more plasticizers or additives.

Particles Comprising a Polymeric Matrix

In some embodiments, particles can comprise a matrix of polymers. In some embodiments, a therapeutic agent and/or targeting moiety can be covalently associated with the surface of a polymeric matrix. In some embodiments, covalent association is mediated by a linker. In some embodiments, a therapeutic agent and/or targeting moiety can be non-covalently associated with the surface of a polymeric matrix. In some embodiments, a therapeutic agent and/or targeting moiety can be associated with the surface of, encapsulated within, surrounded by, and/or dispersed throughout a polymeric matrix.

A wide variety of polymers and methods for forming particles therefrom are known in the art of drug delivery. In some embodiments of the invention, the matrix of a particle comprises one or more polymers. Any polymer may be used in accordance with the present invention. Polymers may be natural or unnatural (synthetic) polymers. Polymers may be homopolymers or copolymers comprising two or more monomers. In terms of sequence, copolymers may be random, block, or comprise a combination of random and block sequences. Typically, polymers in accordance with the present invention are organic polymers.

Examples of polymers include polyethylenes, polycarbonates (e.g. poly(1,3-dioxan-2one)), polyanhydrides (e.g. poly(sebacic anhydride)), polyhydroxyacids (e.g. poly(β-hydroxyalkanoate)), polypropylfumerates, polycaprolactones, polyamides (e.g. polycaprolactam), polyacetals, polyethers, polyesters (e.g. polylactide, polyglycolide), poly(orthoesters), polycyanoacrylates, polyvinyl alcohols, polyurethanes, polyphosphazenes, polyacrylates, polymethacrylates, polyureas, polystyrenes, and polyamines. In some embodiments, polymers in accordance with the present invention include polymers which have been approved for use in humans by the U.S. Food and Drug Administration (FDA) under 21 C.F.R. §177.2600, including but not limited to polyesters (e.g. polylactic acid, poly(lactic-co-glycolic acid), polycaprolactone, polyvalerolactone, poly(1,3-dioxan-2one)); polyanhydrides (e.g. poly(sebacic anhydride)); polyethers (e.g., polyethylene glycol); polyurethanes; polymethacrylates; polyacrylates; and polycyanoacrylates.

In some embodiments, polymers can be hydrophilic. For example, polymers may comprise anionic groups (e.g. phosphate group, sulphate group, carboxylate group); cationic groups (e.g. quaternary amine group); or polar groups (e.g. hydroxyl group, thiol group, amine group).

In some embodiments, polymers may be modified with one or more moieties and/or functional groups. Any moiety or functional group can be used in accordance with the present invention. In some embodiments, polymers may be modified with polyethylene glycol (PEG), with a carbohydrate, and/or with acyclic polyacetals derived from polysaccharides (Papisov, 2001, *ACS Symposium Series,* 786:301).

In some embodiments, may be modified with a lipid or fatty acid group, properties of which are described in further detail below. In some embodiments, a fatty acid group may be one or more of butyric, caproic, caprylic, capric, lauric, myristic, palmitic, stearic, arachidic, behenic, or lignoceric acid. In some embodiments, a fatty acid group may be one or more of palmitoleic, oleic, vaccenic, linoleic, alpha-linoleic, gamma-linoleic, arachidonic, gadoleic, arachidonic, eicosapentaenoic, docosahexaenoic, or erucic acid.

In some embodiments, polymers may be polyesters, including copolymers comprising lactic acid and glycolic acid units, such as poly(lactic acid-co-glycolic acid) and poly(lactide-co-glycolide), collectively referred to herein as "PLGA"; and homopolymers comprising glycolic acid units, referred to herein as "PGA," and lactic acid units, such as poly-L-lactic acid, poly-D-lactic acid, poly-D,L-lactic acid, poly-L-lactide, poly-D-lactide, and poly-D,L-lactide, collectively referred to herein as "PLA." In some embodiments, exemplary polyesters include, for example, polyhydroxyacids; PEGylated polymers and copolymers of lactide and glycolide (e.g. PEGylated PLA, PEGylated PGA, PEGylated PLGA, and derivatives thereof. In some embodiments, polyesters include, for example, polyanhydrides, poly(ortho ester) PEGylated poly(ortho ester), poly(caprolactone), PEGylated poly(caprolactone), polylysine, PEGylated polylysine, poly(ethylene imine), PEGylated poly(ethylene imine), poly(L-lactide-co-L-lysine), poly(serine ester), poly (4-hydroxy-L-proline ester), poly[α-(4-aminobutyl)-L-glycolic acid], and derivatives thereof.

In some embodiments, a polymer may be PLGA. PLGA is a biocompatible and biodegradable co-polymer of lactic acid and glycolic acid, and various forms of PLGA are characterized by the ratio of lactic acid:glycolic acid. Lactic acid can be L-lactic acid, D-lactic acid, or D,L-lactic acid. The degradation rate of PLGA can be adjusted by altering the lactic acid:glycolic acid ratio. In some embodiments, PLGA to be used in accordance with the present invention is characterized by a lactic acid:glycolic acid ratio of approximately 85:15, approximately 75:25, approximately 60:40, approximately 50:50, approximately 40:60, approximately 25:75, or approximately 15:85.

In some embodiments, polymers may be one or more acrylic polymers. In certain embodiments, acrylic polymers include, for example, acrylic acid and methacrylic acid copolymers, methyl methacrylate copolymers, ethoxyethyl methacrylates, cyanoethyl methacrylate, aminoalkyl methacrylate copolymer, poly(acrylic acid), poly(methacrylic acid), methacrylic acid alkylamide copolymer, poly(methyl methacrylate), poly(methacrylic acid anhydride), methyl methacrylate, polymethacrylate, poly(methyl methacrylate) copolymer, polyacrylamide, aminoalkyl methacrylate copolymer, glycidyl methacrylate copolymers, polycyanoacrylates, and combinations comprising one or more of the foregoing polymers. The acrylic polymer may comprise fully-polymerized copolymers of acrylic and methacrylic acid esters with a low content of quaternary ammonium groups.

In some embodiments, polymers can be cationic polymers. In general, cationic polymers are able to condense and/or protect negatively charged strands of nucleic acids (e.g. DNA, RNA, or derivatives thereof). Amine-containing polymers such as poly(lysine) (Zauner et al., 1998, *Adv. Drug Del. Rev.,* 30:97; and Kabanov et al., 1995, *Bioconjugate Chem.,* 6:7); poly(ethylene imine) (PEI; Boussif et al., 1995, *Proc. Natl. Acad. Sci., USA,* 1995, 92:7297), and poly(amidoamine) dendrimers (Kukowska-Latallo et al., 1996, *Proc. Natl. Acad. Sci., USA,* 93:4897; Tang et al., 1996, *Bioconjugate Chem.,* 7:703; and Haensler et al., 1993, *Bioconjugate Chem.,* 4:372) are positively-charged at physiological pH, form ion pairs with nucleic acids, and mediate transfection in a variety of cell lines.

In some embodiments, polymers can be degradable polyesters bearing cationic side chains (Putnam et al., 1999, *Macromolecules,* 32:3658; Barrera et al., 1993, *J. Am. Chem. Soc.,* 115:11010; Kwon et al., 1989, *Macromolecules,* 22:3250; Lim et al., 1999, *J. Am. Chem. Soc.,* 121:5633; and Zhou et al., 1990, *Macromolecules,* 23:3399). Examples of these polyesters include poly(L-lactide-co-L-lysine) (Barrera et al., 1993, *J. Am. Chem. Soc.,* 115:11010), poly(serine ester) (Zhou et al., 1990, *Macromolecules,* 23:3399), poly(4-hydroxy-L-proline ester) (Putnam et al., 1999, *Macromolecules,* 32:3658; and Lim et al., 1999, *J. Am. Chem. Soc.,* 121:5633). Poly(4-hydroxy-L-proline ester) was recently demonstrated to condense plasmid DNA through electrostatic interactions, and to mediate gene transfer (Putnam et al., 1999, *Macromolecules,* 32:3658; and Lim et al., 1999, *J. Am. Chem. Soc.,* 121:5633). These new polymers are less toxic than poly(lysine) and PEI, and they degrade into non-toxic metabolites.

In some embodiments, a polymer in accordance with the present invention may be a carbohydrate, properties of which are described in further detail below. In some embodiments, a carbohydrate may be a polysaccharide comprising simple sugars (or their derivatives) connected by glycosidic bonds, as known in the art. In some embodiments, a carbohydrate may be one or more of pullulan, cellulose, microcrystalline cellulose, hydroxypropyl methylcellulose, hydroxycellulose, methylcellulose, dextran, cyclodextran, glycogen, starch, hydroxyethylstarch, carageenan, glycon, amylose, chitosan, N,O-carboxylmethylchitosan, algin and alginic acid, starch, chitin, heparin, konjac, glucommannan, pustulan, heparin, hyaluronic acid, curdlan, and xanthan.

In some embodiments, a polymer in accordance with the present invention may be a protein or peptide, properties of which are described in further detail below. Exemplary proteins that may be used in accordance with the present invention include, but are not limited to, albumin, collagen, a poly(amino acid) (e.g. polylysine), an antibody, etc.

In some embodiments, a polymer in accordance with the present invention may be a nucleic acid (i.e. polynucleotide), properties of which are described in further detail below. Exemplary polynucleotides that may be used in accordance with the present invention include, but are not limited to, DNA, RNA, etc.

The properties of these and other polymers and methods for preparing them are well known in the art (see, for example, U.S. Pat. Nos. 6,123,727; 5,804,178; 5,770,417; 5,736,372; 5,716,404; 6,095,148; 5,837,752; 5,902,599; 5,696,175; 5,514,378; 5,512,600; 5,399,665; 5,019,379; 5,010,167; 4,806,621; 4,638,045; and 4,946,929; Wang et al., 2001, *J. Am. Chem. Soc.,* 123:9480; Lim et al., 2001, *J. Am. Chem. Soc.,* 123:2460; Langer, 2000, *Am. Chem. Res.,* 33:94; Langer, 1999, *J. Control. Release,* 62:7; and Uhrich et al., 1999, *Chem. Rev.,* 99:3181). More generally, a variety of methods for synthesizing suitable polymers are described in *Concise Encyclopedia of Polymer Science and Polymeric Amines and Ammonium Salts,* Ed. by Goethals, Pergamon Press, 1980; *Principles of Polymerization* by Odian, John Wiley & Sons, Fourth Edition, 2004; *Contemporary Polymer Chemistry* by Allcock et al., Prentice-Hall, 1981; Deming et al., 1997, *Nature,* 390:386; and in U.S. Pat. Nos. 6,506,577, 6,632,922, 6,686,446, and 6,818,732.

In some embodiments, polymers can be linear or branched polymers. In some embodiments, polymers can be dendrimers. In some embodiments, polymers can be substantially cross-linked to one another. In some embodiments, polymers can be substantially free of cross-links. In some embodiments, polymers can be used in accordance with the present invention without undergoing a cross-linking step.

It is further to be understood that inventive targeted particles may comprise block copolymers, graft copolymers, blends, mixtures, and/or adducts of any of the foregoing and other polymers.

Those skilled in the art will recognize that the polymers listed herein represent an exemplary, not comprehensive, list of polymers that can be of use in accordance with the present invention.

Non-Polymeric Particles

In some embodiments, particles can be non-polymeric particles (e.g. metal particles, quantum dots, ceramic particles, polymers comprising inorganic materials, bone particles, viral particles, etc.). In some embodiments, a therapeutic agent to be delivered can be associated with the surface of such a non-polymeric particle. In some embodiments, a non-polymeric particle is an aggregate of non-polymeric components, such as an aggregate of metal atoms (e.g. gold atoms). In some embodiments, a therapeutic agent to be delivered can be associated with the surface of and/or encapsulated within, surrounded by, and/or dispersed throughout an aggregate of non-polymeric components.

In certain embodiments of the invention, non-polymeric particles comprise gradient or homogeneous alloys. In certain embodiments of the invention, particles are composite particles made of two or more materials, of which one, more than one, or all of the materials possess an optically or magnetically detectable property, as discussed in further detail below.

In certain embodiments of the invention, particles comprise silica ($SiO_2$). For example, a particle may consist at least in part of silica, e.g., it may consist essentially of silica or may have an optional coating layer composed of a different material. In some embodiments, a particle has a silica core and an outside layer composed of one or more other materials. In some embodiments, a particle has an outer layer of silica and a core composed of one or more other materials. The amount of silica in the particle, or in a core or coating layer comprising silica, can range from approximately 5% to 100% by mass, volume, or number of atoms, or can assume any value or range between 5% and 100%.

Preparation of Particles

Particles (e.g. nanoparticles, microparticles) may be prepared using any method known in the art. For example, particulate formulations can be formed by methods as nanoprecipitation, flow focusing using fluidic channels, spray drying, single and double emulsion solvent evaporation, solvent extraction, phase separation, milling, microemulsion procedures, microfabrication, nanofabrication, sacrificial layers, simple and complex coacervation, and other methods well known to those of ordinary skill in the art. Alternatively or additionally, aqueous and organic solvent syntheses for monodisperse semiconductor, conductive, magnetic, organic, and other nanoparticles have been described (Pellegrino et al., 2005, *Small*, 1:48; Murray et al., 2000, *Ann. Rev. Mat. Sci.*, 30:545; and Trindade et al., 2001, *Chem. Mat.*, 13:3843).

In certain embodiments, particles are prepared by the nanoprecipitation process or spray drying. Conditions used in preparing particles may be altered to yield particles of a desired size or property (e.g., hydrophobicity, hydrophilicity, external morphology, "stickiness," shape, etc.). The method of preparing the particle and the conditions (e.g., solvent, temperature, concentration, air flow rate, etc.) used may depend on the therapeutic agent to be delivered and/or the composition of the polymer matrix.

Methods for making microparticles for delivery of encapsulated agents are described in the literature (see, e.g., Doubrow, Ed., "Microcapsules and Nanoparticles in Medicine and Pharmacy," CRC Press, Boca Raton, 1992; Mathiowitz et al., 1987, *J. Control. Release,* 5:13; Mathiowitz et al., 1987, *Reactive Polymers,* 6:275; and Mathiowitz et al., 1988, *J. Appl. Polymer Sci.,* 35:755).

If particles prepared by any of the above methods have a size range outside of the desired range, particles can be sized, for example, using a sieve.

Surfactants

In some embodiments, particles may optionally comprise one or more surfactants. In some embodiments, a surfactant can promote the production of particles with increased stability, improved uniformity, or increased viscosity. Surfactants can be particularly useful in embodiments that utilize two or more dispersion media. The percent of surfactant in particles can range from 0% to 99% by weight, from 10% to 99% by weight, from 25% to 99% by weight, from 50% to 99% by weight, or from 75% to 99% by weight. In some embodiments, the percent of surfactant in particles can range from 0% to 75% by weight, from 0% to 50% by weight, from 0% to 25% by weight, or from 0% to 10% by weight. In some embodiments, the percent of surfactant in particles can be approximately 1% by weight, approximately 2% by weight, approximately 3% by weight, approximately 4% by weight, approximately 5% by weight, approximately 10% by weight, approximately 15% by weight, approximately 20% by weight, approximately 25% by weight, or approximately 30% by weight.

Any surfactant known in the art is suitable for use in making particles in accordance with the present invention. Such surfactants include, but are not limited to, phosphoglycerides; phosphatidylcholines; dipalmitoyl phosphatidylcholine (DPPC); dioleylphosphatidyl ethanolamine (DOPE); dioleyloxypropyltriethylammonium (DOTMA); dioleoylphosphatidylcholine; cholesterol; cholesterol ester; diacylglycerol; diacylglycerolsuccinate; diphosphatidyl glycerol (DPPG); hexanedecanol; fatty alcohols such as polyethylene glycol (PEG); polyoxyethylene-9-lauryl ether; a surface active fatty acid, such as palmitic acid or oleic acid; fatty acids; fatty acid monoglycerides; fatty acid diglycerides; fatty acid amides; sorbitan trioleate (Span 85) glycocholate; sorbitan monolaurate (Span 20); polysorbate 20 (Tween-20); polysorbate 60 (Tween-60); polysorbate 65 (Tween-65); polysorbate 80 (Tween-80); polysorbate 85 (Tween-85); polyoxyethylene monostearate; surfactin; a poloxomer; a sorbitan fatty acid ester such as sorbitan trioleate; lecithin; lysolecithin; phosphatidylserine; phosphatidylinositol; sphingomyelin; phosphatidylethanolamine (cephalin); cardiolipin; phosphatidic acid; cerebrosides; dicetylphosphate; dipalmitoylphosphatidylglycerol; stearylamine; dodecylamine; hexadecyl-amine; acetyl palmitate; glycerol ricinoleate; hexadecyl sterate; isopropyl myristate; tyloxapol; poly(ethylene glycol)5000-phosphatidylethanolamine; poly(ethylene glycol)400-monostearate; phospholipids; synthetic and/or natural detergents having high surfactant properties; deoxycholates; cyclodextrins; chaotropic salts; ion pairing agents; and combinations thereof. The surfactant component may be a mixture of different surfactants. These surfactants may be extracted and purified from a natural source or may be prepared synthetically in a laboratory. In certain specific embodiments, surfactants are commercially available.

Those skilled in the art will recognize that this is an exemplary, not comprehensive, list of substances with surfactant activity. Any surfactant may be used in the production of particles to be used in accordance with the present invention.

Lipids

In some embodiments, particles may optionally comprise one or more lipids. The percent of lipid in particles can range from 0% to 99% by weight, from 10% to 99% by weight, from 25% to 99% by weight, from 50% to 99% by weight, or from 75% to 99% by weight. In some embodiments, the percent of lipid in particles can range from 0% to 75% by weight, from 0% to 50% by weight, from 0% to 25% by weight, or from 0% to 10% by weight. In some embodiments, the percent of lipid in particles can be approximately 1% by weight, approximately 2% by weight, approximately 3% by weight, approximately 4% by weight, approximately 5% by weight, approximately 10% by weight, approximately 15% by weight, approximately 20% by weight, approximately 25% by weight, or approximately 30% by weight.

In some embodiments, lipids are oils. In general, any oil known in the art can be included in particles. In some embodiments, an oil may comprise one or more fatty acid groups or salts thereof. In some embodiments, a fatty acid group may comprise digestible, long chain (e.g., $C_8$-$C_{50}$), substituted or unsubstituted hydrocarbons. In some embodiments, a fatty acid group may be a $C_{10}$-$C_{20}$ fatty acid or salt thereof. In some embodiments, a fatty acid group may be a $C_{15}$-$C_{20}$ fatty acid or salt thereof. In some embodiments, a fatty acid group may be a $C_{15}$-$C_{25}$ fatty acid or salt thereof. In some embodiments, a fatty acid group may be unsaturated. In some embodiments, a fatty acid group may be monounsaturated. In some embodiments, a fatty acid group may be polyunsaturated. In some embodiments, a double bond of an unsaturated fatty acid group may be in the cis conformation. In some embodiments, a double bond of an unsaturated fatty acid may be in the trans conformation.

In some embodiments, a fatty acid group may be one or more of butyric, caproic, caprylic, capric, lauric, myristic, palmitic, stearic, arachidic, behenic, or lignoceric acid. In some embodiments, a fatty acid group may be one or more of palmitoleic, oleic, vaccenic, linoleic, alpha-linolenic, gamma-linoleic, arachidonic, gadoleic, arachidonic, eicosapentaenoic, docosahexaenoic, or erucic acid.

In some embodiments, the oil is a liquid triglyceride.

Suitable oils for use with the present invention include, but are not limited to, almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, jojoba, kukui nut, lavandin, lavender, lemon, litsea cubeba, macademia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils, and combinations thereof. Suitable oils for use with the present invention include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and combinations thereof.

In some embodiments, a lipid is a hormone (e.g. estrogen, testosterone), steroid (e.g., cholesterol, bile acid), vitamin (e.g. vitamin E), phospholipid (e.g. phosphatidyl choline), sphingolipid (e.g. ceramides), or lipoprotein (e.g. apolipoprotein).

Carbohydrates

In some embodiments, particles may optionally comprise one or more carbohydrates. The percent of carbohydrate in particles can range from 0% to 99% by weight, from 10% to 99% by weight, from 25% to 99% by weight, from 50% to 99% by weight, or from 75% to 99% by weight. In some embodiments, the percent of carbohydrate in particles can range from 0% to 75% by weight, from 0% to 50% by weight, from 0% to 25% by weight, or from 0% to 10% by weight. In some embodiments, the percent of carbohydrate in particles can be approximately 1% by weight, approximately 2% by weight, approximately 3% by weight, approximately 4% by weight, approximately 5% by weight, approximately 10% by weight, approximately 15% by weight, approximately 20% by weight, approximately 25% by weight, or approximately 30% by weight.

Carbohydrates may be natural or synthetic. A carbohydrate may be a derivatized natural carbohydrate. In certain embodiments, a carbohydrate is a monosaccharide, including but not limited to glucose, fructose, galactose, ribose, lactose, sucrose, maltose, trehalose, cellbiose, mannose, xylose, arabinose, glucoronic acid, galactoronic acid, mannuronic acid, glucosamine, galatosamine, and neuramic acid. In certain embodiments, a carbohydrate is a disaccharide, including but not limited to lactose, sucrose, maltose, trehalose, and cellobiose. In certain embodiments, a carbohydrate is a polysaccharide, including but not limited to pullulan, cellulose, microcrystalline cellulose, hydroxypropyl methylcellulose (HPMC), hydroxycellulose (HC), methylcellulose (MC), dextran, cyclodextran, glycogen, starch, hydroxyethylstarch, carageenan, glycon, amylose, chitosan, N,O-carboxylmethylchitosan, algin and alginic acid, starch, chitin, heparin, konjac, glucommannan, pustulan, heparin, hyaluronic acid, curdlan, and xanthan. In certain embodiments, the carbohydrate is a sugar alcohol, including but not limited to mannitol, sorbitol, xylitol, erythritol, maltitol, and lactitol.

Targeting Moieties

In general, inventive targeting particles comprise one or more targeting moieties. In certain embodiments of the invention, particles are associated with one or more targeting moieties. A targeting moiety is any moiety that binds to a component associated with an organ, tissue, cell, extracellular matrix, and/or intracellular compartment. In some embodiments, such a component is referred to as a "target" or a "marker," and these are discussed in further detail below.

A targeting moiety may be a nucleic acid, polypeptide, glycoprotein, carbohydrate, lipid, etc. For example, a targeting moiety can be a nucleic acid targeting moiety (e.g. an aptamer) that binds to a cell type specific marker. In general, an aptamer is an oligonucleotide (e.g., DNA, RNA, or an analog or derivative thereof) that binds to a particular target, such as a polypeptide. In some embodiments, a targeting moiety may be a naturally occurring or synthetic ligand for a cell surface receptor, e.g., a growth factor, hormone, LDL, transferrin, etc. A targeting moiety can be an antibody, which term is intended to include antibody fragments, characteristic portions of antibodies, single chain antibodies, etc. Synthetic binding proteins such as affibodies, etc., can be used. Peptide targeting moieties can be identified, e.g., using procedures such as phage display. This widely used technique has been used to identify cell specific ligands for a variety of different cell types.

In some embodiments, targeting moieties bind to an organ, tissue, cell, extracellular matrix component, and/or intracellular compartment that is associated with a specific developmental stage or a specific disease state. In some embodiments, a target is an antigen on the surface of a cell, such as a cell surface receptor, an integrin, a transmembrane protein, an ion channel, and/or a membrane transport protein. In some embodiments, a target is an intracellular protein. In some embodiments, a target is a soluble protein, such as immunoglobulin. In certain specific embodiments, a target is a tumor marker. In some embodiments, a tumor marker is an antigen that is present in a tumor that is not present in normal tissue. In some embodiments, a tumor marker is an antigen that is more prevalent in a tumor than in normal tissue. In some embodiments, a tumor marker is an antigen that is more prevalent in malignant cancer cells than in normal cells.

In some embodiments, a target is preferentially expressed in tumor tissues versus normal tissues. For example, when compared with expression in normal tissues, expression of prostate specific membrane antigen (PSMA) is at least 10-fold overexpressed in malignant prostate relative to normal tissue, and the level of PSMA expression is further up-regulated as the disease progresses into metastatic phases (Silver et al., 1997, *Clin. Cancer Res.*, 3:81).

In some embodiments, inventive targeted particles comprise less than 50% by weight, less than 40% by weight, less than 30% by weight, less than 20% by weight, less than 15% by weight, less than 10% by weight, less than 5% by weight, less than 1% by weight, or less than 0.5% by weight of the targeting moiety.

In some embodiments, targeting moieties are covalently associated with a particle. In some embodiments, covalent association is mediated by a linker. In some embodiments, targeting moieties are not covalently associated with a particle. For example, targeting moieties may be associated with the surface of, encapsulated within, surrounded by, and/or distributed throughout the polymeric matrix of an inventive particle. Association of targeting moieties with particles is discussed in further detail below, in the section entitled "Production of Targeted Particles."

Nucleic Acid Targeting Moieties

As used herein, a "nucleic acid targeting moiety" is a nucleic acid that binds selectively to a target. In some embodiments, a nucleic acid targeting moiety is a nucleic acid aptamer. An aptamer is usually a polynucleotide that binds to a specific target structure that is associated with a particular organ, tissue, cell, extracellular matrix component, and/or intracellular compartment. In general, the targeting function of the aptamer is based on the three-dimensional structure of the aptamer. In some embodiments, binding of an aptamer to a target is typically mediated by the interaction between the two- and/or three-dimensional structures of both the aptamer and the target. In some embodiments, binding of an aptamer to a target is not solely based on the primary sequence of the aptamer, but depends on the three-dimensional structure(s) of the aptamer and/or target. In some embodiments, aptamers bind to their targets via complementary Watson-Crick base pairing which is interrupted by structures (e.g. hairpin loops) that disrupt base pairing.

One of ordinary skill in the art will recognize that any aptamer that is capable of specifically binding to a target can be used in accordance with the present invention. In some embodiments, aptamers to be used in accordance with the present invention may target cancer-associated targets. In some embodiments, aptamers to be used in accordance with the present invention may target tumor markers.

In certain embodiments, aptamers to be used in accordance with the present invention may target prostate cancer associated antigens, such as PSMA. Exemplary PSMA-targeting aptamers to be used in accordance with the present invention include, but are not limited to, the A10 aptamer, having a nucleotide sequence of 5'-GGGAGGACGAUGCGGAUCAGCCAUGU-UUACGUCACUCCUUGUCAAUCCUCAUCG-GCAGACGACUCGCCCGA-3' (SEQ ID NO.: 1) (Lupold et al., 2002, Cancer Res., 62:4029), the A9 aptamer, having nucleotide sequence of 5'-GGGAGGACGAUGCGGACCGAAAAAGAC-CUGACUUCUAUACUAAGUCUACGUUC-CAGACGACUCGCCCGA-3' (SEQ ID NO.: 2) (Lupold et al., 2002, Cancer Res., 62:4029; and Chu et al., 2006, Nuc. Acid Res., 34:e73), derivatives thereof, and/or characteristic portions thereof.

In some embodiments, a nucleotide sequence that is homologous to a nucleic acid targeting moiety may be used in accordance with the present invention. In some embodiments, a nucleotide sequence is considered to be "homologous" to a nucleic acid targeting moiety if it comprises fewer than 30, 25, 20, 15, 10, 5, 4, 3, 2, or 1 nucleic acid substitutions relative to the aptamer. In some embodiments, a nucleotide sequence is considered to be "homologous" to a nucleic acid targeting moiety if their sequences are at least 25%, 30%, 35%, 40%, 45%, 50%, 55%, 60%, 65%, 70%, 75%, 80%, 85%, 90%, 95%, or 99% identical. In some embodiments, a nucleic acid sequence is considered to be "homologous" to a nucleic acid targeting moiety if their sequences are at least 25%, 30%, 35%, 40%, 45%, 50%, 55%, 60%, 65%, 70%, 75%, 80%, 85%, 90%, 95%, or 99% similar.

Nucleic acids of the present invention (including nucleic acid targeting moieties and/or functional RNAs to be delivered, e.g., RNAi agents, ribozymes, tRNAs, etc., described in further detail below) may be prepared according to any available technique including, but not limited to chemical synthesis, enzymatic synthesis, enzymatic or chemical cleavage of a longer precursor, etc. Methods of synthesizing RNAs are known in the art (see, e.g., Gait, M. J. (ed.) *Oligonucleotide synthesis: a practical approach*, Oxford [Oxfordshire], Washington, D.C.: IRL Press, 1984; and Herdewijn, P. (ed.) *Oligonucleotide synthesis: methods and applications*, Methods in molecular biology, v. 288 (Clifton, N.J.) Totowa, N.J.: Humana Press, 2005).

The nucleic acid that forms the nucleic acid targeting moiety may comprise naturally occurring nucleosides, modified nucleosides, naturally occurring nucleosides with hydrocarbon linkers (e.g., an alkylene) or a polyether linker (e.g., a PEG linker) inserted between one or more nucleosides, modified nucleosides with hydrocarbon or PEG linkers inserted between one or more nucleosides, or a combination of thereof. In some embodiments, nucleotides or modified nucleotides of the nucleic acid targeting moiety can be replaced with a hydrocarbon linker or a polyether linker provided that the binding affinity and selectivity of the nucleic acid targeting moiety is not substantially reduced by the substitution (e.g., the dissociation constant of the nucleic acid targeting moiety for the target should not be greater than about $1 \times 10^{-3}$ M).

It will be appreciated by those of ordinary skill in the art that nucleic acids in accordance with the present invention may comprise nucleotides entirely of the types found in naturally occurring nucleic acids, or may instead include one or more nucleotide analogs or have a structure that otherwise differs from that of a naturally occurring nucleic acid. U.S. Pat. Nos. 6,403,779; 6,399,754; 6,225,460; 6,127,533; 6,031,086; 6,005,087; 5,977,089; and references therein disclose a wide variety of specific nucleotide analogs and modifications that may be used. See Crooke, S. (ed.) *Antisense Drug Technology: Principles, Strategies, and Applications* (1$^{st}$ ed), Marcel Dekker; ISBN: 0824705661; 1st edition (2001) and references therein. For example, 2'-modifications include halo, alkoxy and allyloxy groups. In some embodiments, the 2'-OH group is replaced by a group selected from H, OR, R, halo, SH, $SR_1$, $NH_2$, $NH_R$, $NR_2$ or CN, wherein R is $C_1$-$C_6$ alkyl, alkenyl, or alkynyl, and halo is F, Cl, Br or I. Examples of modified linkages include phosphorothioate and 5'-N-phosphoramidite linkages.

Nucleic acids comprising a variety of different nucleotide analogs, modified backbones, or non-naturally occurring internucleoside linkages can be utilized in accordance with the present invention. Nucleic acids of the present invention may include natural nucleosides (i.e., adenosine, thymidine, guanosine, cytidine, uridine, deoxyadenosine, deoxythymidine, deoxyguanosine, and deoxycytidine) or modified nucleosides. Examples of modified nucleotides include base modified nucleoside (e.g., aracytidine, inosine, isoguanosine, nebularine, pseudouridine, 2,6-diaminopurine, 2-aminopurine, 2-thiothymidine, 3-deaza-5-azacytidine, 2'-deoxyuridine, 3-nitorpyrrole, 4-methylindole, 4-thiouridine, 4-thiothymidine, 2-aminoadenosine, 2-thiothymidine, 2-thiouridine, 5-bromocytidine, 5-iodouridine, inosine, 6-azauridine, 6-chloropurine, 7-deazaadenosine, 7-deazaguanosine, 8-azaadenosine, 8-azidoadenosine, benzimidazole, M1-methyladenosine, pyrrolo-pyrimidine, 2-amino-6-chloropurine, 3-methyl adenosine, 5-propynylcytidine, 5-propynyluridine, 5-bromouridine, 5-fluorouridine, 5-methylcytidine, 7-deazaadenosine, 7-deazaguanosine, 8-oxoadenosine, 8-oxoguanosine, O(6)-methylguanine, and 2-thiocytidine), chemically or biologically modified bases (e.g., methylated bases), modified sugars (e.g., 2'-fluororibose, 2'-aminoribose, 2'-azidoribose, 2'-O-methylribose, L-enantiomeric nucleosides arabinose, and hexose), modified phosphate groups (e.g., phosphorothioates and 5'-N-phosphoramidite linkages), and combinations thereof. Natural and modified nucleotide monomers for the chemical synthesis of nucleic acids are readily available. In some cases, nucleic acids comprising such modifications display improved properties relative to nucleic acids consisting only of naturally occurring nucleotides. In some embodiments, nucleic acid modifications described herein are utilized to reduce and/or prevent digestion by nucleases (e.g. exonucleases, endonucleases, etc.). For example, the structure of a nucleic acid may be stabilized by including nucleotide analogs at the 3' end of one or both strands order to reduce digestion.

Modified nucleic acids need not be uniformly modified along the entire length of the molecule. Different nucleotide modifications and/or backbone structures may exist at various positions in the nucleic acid. One of ordinary skill in the art will appreciate that the nucleotide analogs or other modification(s) may be located at any position(s) of a nucleic acid such that the function of the nucleic acid is not substantially affected. To give but one example, modifications may be located at any position of an aptamer such that the ability of the aptamer to specifically bind to the aptamer target is not substantially affected. The modified region may be at the 5'-end and/or the 3'-end of one or both strands. For example, modified aptamers in which approximately 1-5 residues at the 5' and/or 3' end of either of both strands are nucleotide analogs and/or have a backbone modification have been employed. The modification may be a 5' or 3' terminal modification. One or both nucleic acid strands may comprise at least 50% unmodified nucleotides, at least 80% unmodified nucleotides, at least 90% unmodified nucleotides, or 100% unmodified nucleotides.

Nucleic acids in accordance with the present invention may, for example, comprise a modification to a sugar, nucleoside, or internucleoside linkage such as those described in U.S. Patent Publications 2003/0175950, 2004/0192626, 2004/0092470, 2005/0020525, and 2005/0032733. The present invention encompasses the use of any nucleic acid having any one or more of the modification described therein. For example, a number of terminal conjugates, e.g., lipids such as cholesterol, lithocholic acid, aluric acid, or long alkyl branched chains have been reported to improve cellular uptake. Analogs and modifications may be tested using, e.g., using any appropriate assay known in the art, for example, to select those that result in improved delivery of a therapeutic agent, improved specific binding of an aptamer to an aptamer target, etc. In some embodiments, nucleic acids in accordance with the present invention may comprise one or more non-natural nucleoside linkages. In some embodiments, one or more internal nucleotides at the 3'-end, 5'-end, or both 3'- and 5'-ends of the aptamer are inverted to yield a such as a 3'-3' linkage or a 5'-5' linkage.

In some embodiments, nucleic acids in accordance with the present invention are not synthetic, but are naturally-occurring entities that have been isolated from their natural environments.

Small Molecule Targeting Moieties

In some embodiments, a targeting moiety in accordance with the present invention may be a small molecule. In certain embodiments, small molecules are less than about 2000 g/mol in size. In some embodiments, small molecules are less than about 1500 g/mol or less than about 1000 g/mol. In some embodiments, small molecules are less than about 800 g/mol or less than about 500 g/mol.

One of ordinary skill in the art will appreciate that any small molecule that specifically binds to a desired target can be used in accordance with the present invention. One exemplary small molecule targeting moiety is folic acid. Folic acid (i.e., pteroylglutamic acid, Vitamin B9) specifically binds to the folate receptor (FR), which is preferentially expressed in tumor tissues relative to healthy tissues (Low et al., 2004, *Adv. Drug Deliv. Rev.*, 56:1055).

In some embodiments, small molecule targeting moieties that may be used to target cells associated with prostate cancer tumors include PSMA peptidase inhibitors, such as 2-PMPA, GPI5232, VA-033, phenylalkylphosphonamidates (Jackson et al., 2001, *Curr. Med. Chem.*, 8:949; Bennett et al., 1998, *J. Am. Chem. Soc.*, 120:12139; Jackson et al., 2001, *J. Med. Chem.*, 44:4170; Tsukamoto et al., 2002, *Bioorg. Med. Chem. Lett.*, 12:2189; Tang et al., 2003, *Biochem. Biophys. Res. Commun.*, 307:8; Oliver et al., 2003, *Bioorg. Med. Chem.*, 11:4455; and Maung et al., 2004, *Bioorg. Med. Chem.*, 12:4969), and/or analogs and derivatives thereof. In some embodiments, small molecule targeting moieties that may be used to target cells associated with prostate cancer tumors include thiol and indole thiol derivatives, such as 2-MPPA and 3-(2-mercaptoethyl)-1H-indole-2-carboxylic acid derivatives (Majer et al., 2003, *J. Med. Chem.*, 46:1989; and U.S. Patent Publication 2005/0080128). In some embodiments, small molecule targeting moieties that may be used to target cells associated with prostate cancer tumors include hydroxamate derivatives (Stoermer et al., 2003, *Bioorg. Med. Chem. Lett.*, 13:2097). In some embodiments, small molecule targeting moieties that may be used to target cells associated with prostate cancer tumors include PBDA- and urea-based inhibitors, such as ZJ 43, ZJ 11, ZJ 17, ZJ 38 (Nan et al., 2000, *J. Med. Chem.*, 43:772; and Kozikowski et al., 2004, *J. Med. Chem.*, 47:1729), and/or and analogs and derivatives thereof. In some embodiments, small molecule targeting moieties that may be used to target cells associated with prostate cancer tumors include androgen receptor targeting agents (ARTAs), such as those described in U.S. Pat. Nos. 7,026,500; 7,022,870; 6,998,500; 6,995,284; 6,838,484; 6,569,896; 6,492,554; and in U.S. Patent Publications 2006/0287547; 2006/0276540; 2006/0258628; 2006/0241180; 2006/0183931; 2006/0035966; 2006/0009529; 2006/0004042; 2005/0033074; 2004/0260108; 2004/0260092; 2004/0167103; 2004/0147550; 2004/0147489; 2004/0087810; 2004/0067979; 2004/0052727; 2004/0029913; 2004/0014975; 2003/0232792; 2003/0232013; 2003/0225040; 2003/0162761; 2004/0087810; 2003/0022868; 2002/0173495; 2002/0099096; 2002/0099036. In some embodiments, small molecule targeting moieties that may be used to target cells associated with prostate cancer tumors include polyamines, such as putrescine, spermine, and spermidine (U.S. Patent Publications 2005/0233948 and 2003/0035804).

Protein Targeting Moieties

In some embodiments, a targeting moiety in accordance with the present invention may be a protein or peptide. In certain embodiments, peptides range from about 5 to 100, 10 to 75, 15 to 50, or 20 to 25 amino acids in size. In some embodiments, a peptide sequence can be based on the sequence of a protein. In some embodiments, a peptide sequence can be a random arrangement of amino acids.

The terms "polypeptide" and "peptide" are used interchangeably herein, with "peptide" typically referring to a polypeptide having a length of less than about 100 amino acids. Polypeptides may contain L-amino acids, D-amino acids, or both and may contain any of a variety of amino acid modifications or analogs known in the art. Useful modifications include, e.g., terminal acetylation, amidation, lipidation, phosphorylation, glycosylation, acylation, farnesylation, sulfation, etc.

Exemplary proteins that may be used as targeting moieties in accordance with the present invention include, but are not limited to, antibodies, receptors, cytokines, peptide hormones, proteins derrived from combinatorial libraries (e.g. avimers, affibodies, etc.), and characteristic portions thereof.

In some embodiments, any protein targeting moiety can be utilized in accordance with the present invention. To give but a few examples, IL-2, transferrin, GM-CSF, α-CD25, α-CD22, TGF-α, folic acid, α-CEA, α-EpCAM scFV, VEGF, LHRH, bombesin, somatostin, Gal, α-GD2, α-EpCAM, α-CD20, MOv19 scFv, α-Her-2, and α-CD64 can be used to target a variety of cancers, such as lymphoma, glioma, leukemia, brain tumors, melanoma, ovarian cancer, neuroblastoma, folate receptor-expressing tumors, CEA-expressing tumors, EpCAM-expressing tumors, VEGF-expressing tumors, etc. (Eklund et al., 2005, *Expert Rev. Anticancer Ther.*, 5:33; Kreitman et al., 2000, *J. Clin. Oncol.*, 18:1622; Kreitman et al., 2001, *N. Engl. J. Med.*, 345:241; Sampson et al., 2003, *J. Neurooncol.*, 65:27; Weaver et al., 2003, *J. Neurooncol.*, 65:3; Leamon et al., 1993, *J. Biol. Chem.*, 268:24847; Leamon et al., 1994, *J. Drug Target.*, 2:101; Atkinson et al., 2001, *J. Biol. Chem.*, 276:27930; Frankel et al., 2002, *Clin. Cancer Res.*, 8:1004; Francis et al., 2002, *Br. J. Cancer,* 87:600; de Graaf et al., 2002, *Br. J. Cancer,* 86:811; Spooner et al., 2003, *Br. J. Cancer,* 88:1622; Liu et al., 1999, *J. Drug Target.,* 7:43; Robinson et al., 2004, *Proc. Natl. Acad. Sci., USA,* 101:14527; Sondel et al., 2003, *Curr. Opin. Investig. Drugs,* 4:696; Connor et al., 2004, *J. Immunother.,* 27:211; Gillies et al., 2005, *Blood,* 105:3972; Melani et al., 1998, *Cancer Res.,* 58:4146; Metelitsa et al., 2002, *Blood,* 99:4166; Lyu et al., 2005, *Mol. Cancer Ther.,* 4:1205; and Notter et al., 2001, *Blood,* 97:3138).

In some embodiments, protein targeting moieties can be peptides. One of ordinary skill in the art will appreciate that any peptide that specifically binds to a desired target can be used in accordance with the present invention.

In some embodiments, peptide targeting moieties which target tumor vasculature can be used in accordance with the present invention. In some embodiments, peptides targeting tumor vasculature are antagonists or inhibitors of angiogenic proteins that include VEGFR (Binetruy-Tournaire et al, 2000, *EMBO J.,* 19:1525), CD36 (Reiher et al, 2002, *Int. J. Cancer,* 98:682) integrins $a_vps$ and $a_vps$ (Koivunen et al, 1995, *Biotechnology* (NY), 13:265; and Kumar et al, 2001, *Cancer Res.,* 61:2232) aminopeptidase N (Pasqualini et al, 2000, *Cancer Res.,* 60:722), and matrix metalloproteinases (Koivunen et al., 1999, *Nat. Biotechnol,* 17:768). For instance, ATWLPPR (SEQ ID NO: 4) peptide is a potent antagonist of VEGF (Binetruy-Tournaire et al, 2000, *EMBO J.,* 19:1525); thrombospondin-1 (TSP-1) mimetics can induce apoptosis in endothelial cells (Reiher et al, 2002, *Int. J. Cancer,* 98:682); RGD-motif mimics (e.g. cyclic peptide ACDCRGDCFCG (SEQ ID NO: 5) and ROD peptidomimetic SCH 221153) block integrin receptors (Koivunen et al, 1995, *Biotechnology* (NY), 13:265; and Kumar et al, 2001, *Cancer Res.,* 61:2232); NGR-containing peptides (e.g. cyclic CNGRC (SEQ ID NO: 6)) inhibit aminopeptidase N (Pasqualini et al, 2000, *Cancer Res.,* 60:722); and cyclic peptides containing the sequence of HWGF (SEQ ID NO: 7) (e.g. CTTHWGFTLC (SEQ ID NO: 8)) selectively inhibit MMP-2 and MMP-9 (Koivunen et al., 1999, *Nat. Biotechnol.,* 17:768); and a LyP-1 peptide has been identified (CGNKRTRGC (SEQ ID NO: 9)) which specifically binds to tumor lymphatic vessels and induces apoptosis of endothelial cells (Laakkonen et al, 2004, *Proc. Nail Acad. Sci., USA,* 101:9381).

In some embodiments, peptide targeting moieties include peptide analogs that block binding of peptide hormones to receptors expressed in human cancers (Bauer et al., 1982, *Life Sci.,* 31:1133). Exemplary hormone receptors (Reubi et al., 2003, *Endocr. Rev.,* 24:389) include (1) somatostatin receptors (e.g. octreotide, vapreotide, and lanretode) (Froidevaux et al., 2002, *Biopolymers,* 66:161); (2) bombesin/gastrin-releasing peptide (GRP) receptor (e.g. RC-3940 series) (Kanashiro et al., 2003, *Proc. Natl. Acad. Sci., USA,* 100:15836); and (3) LHRH receptor (e.g. Decapeptyl®, Lupron®, Zoladex®, and Cetrorelix®) (Schally et al., 2000, *Prostate,* 45:158).

In some embodiments, peptides which recognize IL-11 receptor-α can be used to target cells associated with prostate cancer tumors (see, e.g., U.S. Patent Publication 2005/0191294).

In some embodiments, protein targeting moieties can be antibodies. One of ordinary skill in the art will appreciate that any antibody that specifically binds to a desired target can be used in accordance with the present invention.

In some embodiments, antibodies which recognize PSMA can be used to target cells associated with prostate cancer tumors. Such antibodies include, but are not limited to, scFv antibodies A5, G0, G1, G2, and G4 and mAbs 3/E7, 3/F11, 3/A12, K7, K12, and D20 (Elsässer-Beile et al., 2006, *Prostate,* 66:1359); mAbs E99, J591, J533, and J415 (Liu et al., 1997, *Cancer Res.,* 57:3629; Liu et al., 1998, *Cancer Res.,* 58:4055; Fracasso et al., 2002, *Prostate,* 53:9; McDevitt et al., 2000, *Cancer Res.,* 60:6095; McDevitt et al., 2001, *Science,* 294:1537; Smith-Jones et al., 2000, *Cancer Res.,* 60:5237; Vallabhajosula et al., 2004, *Prostate,* 58:145; Bander et al., 2003, *J. Urol.,* 170:1717; Patri et al., 2004, *Bioconj. Chem.,* 15:1174; and U.S. Pat. No. 7,163,680); mAb 7E11-C5.3 (Horoszewicz et al., 1987, *Anticancer Res.,* 7:927); antibody 7E11 (Horoszewicz et al., 1987, *Anticancer Res.,* 7:927; and U.S. Pat. No. 5,162,504); and antibodies described in Chang et al., 1999, *Cancer Res.,* 59:3192; Murphy et al., 1998, *J. Urol.,* 160:2396; Grauer et al., 1998, *Cancer Res.,* 58:4787; and Wang et al., 2001, *Int. J. Cancer,* 92:871. One of ordinary skill in the art will appreciate that any antibody that recognizes and/or specifically binds to PSMA may be used in accordance with the present invention.

In some embodiments, antibodies which recognize other prostate tumor-associated antigens are known in the art and can be used in accordance with the present invention to target cells associated with prostate cancer tumors (see, e.g., Vihko et al., 1985, *Biotechnology in Diagnostics,* 131; Babaian et al., 1987, *J. Urol.,* 137:439; Leroy et al., 1989, *Cancer,* 64:1; Meyers et al., 1989, *Prostate,* 14:209; and U.S. Pat. Nos. 4,970,299; 4,902,615; 4,446,122 and Re 33,405; 4,862,851; 5,055,404). To give but a few examples, antibodies have been identified which recognize transmembrane protein 24P4C12 (U.S. Patent Publication 2005/0019870); calveolin (U.S. Patent Publications 2003/0003103 and 2001/0012890); L6 (U.S. Patent Publication 2004/0156846); prostate specific reductase polypeptide (U.S. Pat. No. 5,786,204; and U.S. Patent Publication 2002/0150578); and prostate stem cell antigen (U.S. Patent Publication 2006/0269557).

In some embodiments, protein targeting moieties that may be used to target cells associated with prostate cancer tumors include conformationally constricted dipeptide mimetics (Ding et al., 2004, *Org. Lett.,* 6:1805).

In some embodiments, a targeting moiety may be an antibody and/or characteristic portion thereof. The term "antibody" refers to any immunoglobulin, whether natural or wholly or partially synthetically produced and to derivatives thereof and characteristic portions thereof. An antibody may be monoclonal or polyclonal. An antibody may be a member of any immunoglobulin class, including any of the human classes: IgG, IgM, IgA, IgD, and IgE.

As used herein, an antibody fragment (i.e. characteristic portion of an antibody) refers to any derivative of an antibody which is less than full-length. In general, an antibody fragment retains at least a significant portion of the full-length antibody's specific binding ability. Examples of antibody fragments include, but are not limited to, Fab, Fab', F(ab')2, scFv, Fv, dsFv diabody, and Fd fragments.

An antibody fragment may be produced by any means. For example, an antibody fragment may be enzymatically or chemically produced by fragmentation of an intact antibody and/or it may be recombinantly produced from a gene encoding the partial antibody sequence. Alternatively or additionally, an antibody fragment may be wholly or partially synthetically produced. An antibody fragment may optionally comprise a single chain antibody fragment. Alternatively or additionally, an antibody fragment may comprise multiple chains which are linked together, for example, by disulfide linkages. An antibody fragment may optionally comprise a multimolecular complex. A functional antibody fragment will typically comprise at least about 50 amino acids and more typically will comprise at least about 200 amino acids.

In some embodiments, antibodies may include chimeric (e.g. "humanized") and single chain (recombinant) antibodies. In some embodiments, antibodies may have reduced effector functions and/or bispecific molecules. In some embodiments, antibodies may include fragments produced by a Fab expression library.

Single-chain Fvs (scFvs) are recombinant antibody fragments consisting of only the variable light chain (VL) and variable heavy chain (VH) covalently connected to one another by a polypeptide linker. Either VL or VH may comprise the NH2-terminal domain. The polypeptide linker may be of variable length and composition so long as the two variable domains are bridged without significant steric interference. Typically, linkers primarily comprise stretches of glycine and serine residues with some glutamic acid or lysine residues interspersed for solubility.

Diabodies are dimeric scFvs. Diabodies typically have shorter peptide linkers than most scFvs, and they often show a preference for associating as dimers.

An Fv fragment is an antibody fragment which consists of one VH and one VL domain held together by noncovalent interactions. The term "dsFv" as used herein refers to an Fv with an engineered intermolecular disulfide bond to stabilize the VH-VL pair.

A F(ab')2 fragment is an antibody fragment essentially equivalent to that obtained from immunoglobulins by digestion with an enzyme pepsin at pH 4.0-4.5. The fragment may be recombinantly produced.

A Fab' fragment is an antibody fragment essentially equivalent to that obtained by reduction of the disulfide bridge or bridges joining the two heavy chain pieces in the F(ab')2 fragment. The Fab' fragment may be recombinantly produced.

A Fab fragment is an antibody fragment essentially equivalent to that obtained by digestion of immunoglobulins with an enzyme (e.g. papain). The Fab fragment may be recombinantly produced. The heavy chain segment of the Fab fragment is the Fd piece.

Carbohydrate Targeting Moieties

In some embodiments, a targeting moiety in accordance with the present invention may comprise a carbohydrate. To give but one example, lactose and/or galactose can be used for targeting hepatocytes.

In some embodiments, a carbohydrate may be a polysaccharide comprising simple sugars (or their derivatives) connected by glycosidic bonds, as known in the art. Such sugars may include, but are not limited to, glucose, fructose, galactose, ribose, lactose, sucrose, maltose, trehalose, cellbiose, mannose, xylose, arabinose, glucoronic acid, galactoronic acid, mannuronic acid, glucosamine, galatosamine, and neuramic acid. In some embodiments, a carbohydrate may be one or more of pullulan, cellulose, microcrystalline cellulose, hydroxypropyl methylcellulose, hydroxycellulose, methylcellulose, dextran, cyclodextran, glycogen, starch, hydroxyethylstarch, carageenan, glycon, amylose, chitosan, N,O-carboxylmethylchitosan, algin and alginic acid, starch, chitin, heparin, konjac, glucommannan, pustulan, heparin, hyaluronic acid, curdlan, and xanthan.

In some embodiments, the carbohydrate may be aminated, carboxylated, and/or sulfated. In some embodiments, hydrophilic polysaccharides can be modified to become hydrophobic by introducing a large number of side-chain hydrophobic groups. In some embodiments, a hydrophobic carbohydrate may include cellulose acetate, pullulan acetate, konjac acetate, amylose acetate, and dextran acetate.

Lipid Targeting Moieties

In some embodiments, a targeting moiety in accordance with the present invention may comprise one or more fatty acid groups or salts thereof. In some embodiments, a fatty acid group may comprise digestible, long chain (e.g., $C_8$-$C_{50}$), substituted or unsubstituted hydrocarbons. In some embodiments, a fatty acid group may be a $C_{10}$-$C_{20}$ fatty acid or salt thereof. In some embodiments, a fatty acid group may be a $C_{15}$-$C_{20}$ fatty acid or salt thereof. In some embodiments, a fatty acid group may be a $C_{15}$-$C_{25}$ fatty acid or salt thereof. In some embodiments, a fatty acid group may be unsaturated. In some embodiments, a fatty acid group may be monounsaturated. In some embodiments, a fatty acid group may be polyunsaturated. In some embodiments, a double bond of an unsaturated fatty acid group may be in the cis conformation. In some embodiments, a double bond of an unsaturated fatty acid may be in the trans conformation.

In some embodiments, a fatty acid group may be one or more of butyric, caproic, caprylic, capric, lauric, myristic, palmitic, stearic, arachidic, behenic, or lignoceric acid. In some embodiments, a fatty acid group may be one or more of palmitoleic, oleic, vaccenic, linoleic, alpha-linoleic, gamma-linoleic, arachidonic, gadoleic, arachidonic, eicosapentaenoic, docosahexaenoic, or erucic acid.

Targets

In certain embodiments, targeted particles in accordance with the present invention comprise a targeting moiety which specifically binds to one or more targets (e.g. antigens) associated with an organ, tissue, cell, extracellular matrix, and/or intracellular compartment. In some embodiments, targeted particles comprise a targeting moiety which specifically binds to targets associated with a particular organ or organ system. In some embodiments, targeted particles in accordance with the present invention comprise a targeting moiety which specifically binds to one or more intracellular targets (e.g. organelle, intracellular protein). In some embodiments, targeted particles comprise a targeting moiety which specifically binds to targets associated with diseased tissues. In some embodiments, targeted particles comprise a targeting moiety which specifically binds to targets associated with particular cell types (e.g. endothelial cells, cancer cells, malignant cells, prostate cancer cells, etc.).

In some embodiments, targeted particles in accordance with the present invention comprise a targeting moiety which binds to a target that is specific for one or more particular tissue types (e.g. liver tissue vs. prostate tissue). In some embodiments, targeted particles in accordance with the present invention comprise a targeting moiety which binds to a target that is specific for one or more particular cell types (e.g. T cells vs. B cells). In some embodiments, targeted particles in accordance with the present invention comprise a targeting moiety which binds to a target that is specific for one or more particular disease states (e.g. tumor cells vs. healthy cells). In some embodiments, targeted particles in accordance with the present invention comprise a targeting moiety which binds to a target that is specific for one or more particular developmental stages (e.g. stem cells vs. differentiated cells).

In some embodiments, a target may be a marker that is exclusively or primarily associated with one or a few cell types, with one or a few diseases, and/or with one or a few developmental stages. A cell type specific marker is typically expressed at levels at least 2 fold greater in that cell type than in a reference population of cells which may consist, for example, of a mixture containing cells from a plurality (e.g., 5-10 or more) of different tissues or organs in approximately equal amounts. In some embodiments, the cell type specific marker is present at levels at least 3 fold, at least 4 fold, at least 5 fold, at least 6 fold, at least 7 fold, at least 8 fold, at least 9 fold, at least 10 fold, at least 50 fold, at least 1000 fold, or at least 1000 fold greater than its average expression in a reference population. Detection or measurement of a cell type specific marker may make it possible to distinguish the cell type or types of interest from cells of many, most, or all other types.

In some embodiments, a target can comprise a protein, a carbohydrate, a lipid, and/or a nucleic acid. In certain embodiments, a target can comprise a protein and/or characteristic portion thereof, such as a tumor-marker, integrin, cell surface receptor, transmembrane protein, intercellular protein, ion channel, membrane transporter protein, enzyme, antibody, chimeric protein, glycoprotein, etc. In certain embodiments, a target can comprise a carbohydrate and/or characteristic portion thereof, such as a glycoprotein, sugar (e.g., monosaccharide, disaccharide, polysaccharide), glycocalyx (i.e., the carbohydrate-rich peripheral zone on the outside surface of most eukaryotic cells) etc. In certain embodiments, a target can comprise a lipid and/or characteristic portion thereof, such as an oil, fatty acid, glyceride, hormone, steroid (e.g., cholesterol, bile acid), vitamin (e.g. vitamin E), phospholipid, sphingolipid, lipoprotein, etc. In certain embodiments, a target can comprise a nucleic acid and/or characteristic portion thereof, such as a DNA nucleic acid; RNA nucleic acid; modified DNA nucleic acid; modified RNA nucleic acid; nucleic acid that includes any combination of DNA, RNA, modified DNA, and modified RNA; etc.

Numerous markers are known in the art. Typical markers include cell surface proteins, e.g., receptors. Exemplary receptors include, but are not limited to, the transferrin receptor; LDL receptor; growth factor receptors such as epidermal growth factor receptor family members (e.g., EGFR, HER-2, HER-3, HER-4, HER-2/neu) or vascular endothelial growth factor receptors; cytokine receptors; cell adhesion molecules; integrins; selectins; CD molecules; etc. The marker can be a molecule that is present exclusively or in higher amounts on a malignant cell, e.g., a tumor antigen. For example, prostate-specific membrane antigen (PSMA) is expressed at the surface of prostate cancer cells. In certain embodiments of the invention the marker is an endothelial cell marker.

In certain embodiments of the invention a marker is a tumor marker. The marker may be a polypeptide that is expressed at higher levels on dividing than on non-dividing cells. For example, Her-2/neu (also known as ErbB-2) is a member of the EGF receptor family and is expressed on the cell surface of tumors associated with breast cancer. To give another example, a peptide known as F3 is a suitable targeting agent for directing a nanoparticle to nucleolin (Porkka et al., 2002, *Proc. Natl. Acad. Sci., USA,* 99:7444; and Christian et al., 2003, *J. Cell Biol.,* 163:871). As described in the Examples, targeted particles comprising a nanoparticle and the A10 aptamer (which specifically binds to PSMA) were able to specifically and effectively deliver docetaxel to prostate cancer tumors.

In some embodiments, a marker is a prostate cancer marker. In some embodiments, a prostate cancer marker is expressed by prostate cells but not by other cell types. In some embodiments, a prostate cancer marker is expressed by prostate cancer tumor cells but not by other cell types. Any prostate cancer marker can be used in accordance with the present invention. To give but one non-limiting example, in certain embodiments, a prostate cancer marker is prostate specific membrane antigen (PSMA), a 100 kDa transmembrane glycoprotein that is expressed in most prostatic tissues, but is more highly expressed in prostatic cancer tissue than in normal tissue.

In some embodiments, a prostate cancer marker is transmembrane protein 24P4C12 (U.S. Patent Publication 2005/0019870). In some embodiments, a prostate cancer marker is prostate stem cell antigen (U.S. Patent Publication 2006/0269557). In some embodiments, a prostate cancer marker is the androgen receptor (see, e.g., U.S. Pat. Nos. 7,026,500; 7,022,870; 6,998,500; 6,995,284; 6,838,484; 6,569,896; 6,492,554; and U.S. Patent Publications 2006/0287547; 2006/0276540; 2006/0258628; 2006/0241180; 2006/0183931; 2006/0035966; 2006/0009529; 2006/0004042; 2005/0033074; 2004/0260108; 2004/0260092; 2004/0167103; 2004/0147550; 2004/0147489; 2004/0087810; 2004/0067979; 2004/0052727; 2004/0029913; 2004/0014975; 2003/0232792; 2003/0232013; 2003/0225040; 2003/0162761; 2004/0087810; 2003/0022868; 2002/0173495; 2002/0099096; and 2002/0099036). In some embodiments, a prostate cancer marker is calveolin (U.S. Pat. No. 7,029,859; and U.S. Patent Publications 2003/0003103 and 2001/0012890). In some embodiments, a prostate cancer marker is prostate specific antigen. In some embodiments, a prostate cancer marker is human glandular kallikrein 2. In some embodiments, a prostate cancer marker is prostatic acid phosphatase. In some embodiments, a prostate cancer marker is insulin-like growth factor and/or insulin-like growth factor binding protein. In some embodiments, a prostate cancer marker is PHOR-1 (U.S. Patent Publication 2004/0248088). In some embodiments, a prostate cancer marker is C-type lectin transmembrane antigen (U.S. Patent Publication 2005/0019872). In some embodiments, a prostate cancer marker is a protein encoded by 103P2D6 (U.S. Patent Publication 2003/0219766). In some embodiments, a prostate cancer marker is a prostatic specific reductase polypeptide (U.S. Pat. No. 5,786,204; and U.S. Patent Publication 2002/0150578). In some embodiments, a prostate cancer marker is an IL-11 receptor-α (U.S. Patent Publication 2005/0191294).

Novel Targeting Moieties

The present invention provides methods for designing novel targeting moieties. The present invention further provides methods for isolating or identifying novel targeting moieties from a mixture of candidate targeting moieties.

Targeting moieties that bind to a protein, a carbohydrate, a lipid, and/or a nucleic acid can be designed and/or identified. In some embodiments, targeting moieties can be designed and/or identified for use in the targeted particles of the invention that bind to proteins and/or characteristic portions thereof, such as tumor-markers, integrins, cell surface receptors, transmembrane proteins, intercellular proteins, ion channels, membrane transporter proteins, enzymes, antibodies, chimeric proteins etc. In some embodiments, targeting moieties can be designed and/or identified for use in the targeted particles of the invention that bind to carbohydrates and/or characteristic portions thereof, such as glycoproteins, sugars (e.g., monosaccharides, disaccharides and polysaccharides), glycocalyx (i.e., the carbohydrate-rich peripheral zone on the outside surface of most eukaryotic cells) etc. In some embodiments, targeting moieties can be designed and/or identified for use in the targeted particles of the invention that bind to lipids and/or characteristic portions thereof, such as oils, saturated fatty acids, unsaturated fatty acids, glycerides, hormones, steroids (e.g., cholesterol, bile acids), vitamins (e.g. vitamin E), phospholipids, sphingolipids, lipoproteins etc. In some embodiments, targeting moieties can be designed and/or identified for use in the targeted particles of the invention that bind to nucleic acids and/or characteristic portions thereof, such as DNA nucleic acids; RNA nucleic acids; modified DNA nucleic acids; modified RNA nucleic acids; and nucleic acids that include any combination of DNA, RNA, modified DNA, and modified RNA; etc.

Nucleic acid targeting moieties (e.g. aptamers) may be designed and/or identified using any available method. In some embodiments, nucleic acid targeting moieties are designed and/or identified by identifying nucleic acid targeting moieties from a candidate mixture of nucleic acids. Systemic Evolution of Ligands by Exponential Enrichment (SELEX), or a variation thereof, is a commonly used method of identifying nucleic acid targeting moieties that bind to a target from a candidate mixture of nucleic acids.

The SELEX process for designing and/or identifying nucleic acid targeting moieties is described in U.S. Pat. Nos. 6,482,594; 6,458,543; 6,458,539; 6,376,190; 6,344,318; 6,242,246; 6,184,364; 6,001,577; 5,958,691; 5,874,218; 5,853,984; 5,843,732; 5,843,653; 5,817,785; 5,789,163; 5,763,177; 5,696,249; 5,660,985; 5,595,877; 5,567,588; and 5,270,163. Briefly, the basic SELEX process may be defined by the following series of steps:

1) A candidate mixture of nucleic acids of differing sequence is prepared. A candidate mixture generally includes regions of fixed sequences (i.e., each of the members of the candidate mixture contains the same sequences in the same location) and regions of randomized sequences. Fixed sequence regions are selected to assist in the amplification steps described below; to mimic a sequence known to bind to the target; and/or to enhance the potential of a given structural arrangement of the nucleic acids in the candidate mixture. Randomized sequences can be totally randomized (i.e., the probability of finding a base at any position being one in four) or only partially randomized (i.e., the probability of finding a base at any location can be selected at any level between 0% and 100%).

2) The candidate mixture is contacted with a selected target under conditions favorable for binding between the target and members of the candidate mixture. Under these circumstances, the interaction between the target and the nucleic acids of the candidate mixture can be considered as forming nucleic acid-target pairs between the target and the nucleic acids having the strongest affinity for the target.

3) Nucleic acids with the highest affinity for the target are partitioned from those nucleic acids with lesser affinity to the target. Because only an extremely small number of sequences (and possibly only one molecule of nucleic acid) corresponding to the highest affinity targeting moieties exist in the candidate mixture, it is generally desirable to set the partitioning criteria so that a significant amount of the targeting moieties in the candidate mixture (approximately 0.1%-10%) is retained during partitioning.

4) Those targeting moieties selected during partitioning as having the relatively higher affinity to the target are then amplified to create a new candidate mixture that is enriched in targeting moieties having a relatively higher affinity for the target.

5) By repeating the partitioning and amplifying steps above, the newly formed candidate mixture contains fewer and fewer unique sequences, and the average degree of affinity of the nucleic acid mixture to the target will generally increase. Taken to its extreme, the SELEX process will yield a candidate mixture containing one or a small number of unique targeting moieties representing those targeting moieties from the original candidate mixture having the highest affinity to the target. In general, targeting moieties identified will have a dissociation constant with the target of about $1\times10^{-6}$ M or less. Typically, the dissociation constant of the nucleic acid targeting moiety and the target will be in the range of between about $1\times10-8$ M and about $1\times10-12$ M.

Nucleic acid targeting moieties that bind selectively to any target can be isolated by the SELEX process, or a variation thereof, provided that the target can be used as a target in the SELEX process.

Alternatively or additionally, Polyplex In Vivo Combinatorial Optimization (PICO) is a method that can be used to identify nucleic acid targeting moieties (e.g. aptamers) that bind to a target from a candidate mixture of nucleic acids in vivo and/or in vitro and is described in co-pending PCT Application US06/47975, entitled "System for Screening Particles," filed Dec. 15, 2006. Briefly, the basic PICO process may be defined by the following series of steps:

1) A library comprising a plurality of nucleic acids is provided and associated with particles (e.g. nanoparticles).

2) The targeted particles are administered to an animal (e.g. mouse) under conditions in which the particles can migrate to a tissue of interest (e.g. tumor).

3) A first population of targeted particles that have migrated to the cells, tissue, or organ of interest is recovered. The nucleic acid targeting moieties associated with the first population of targeted particles are amplified and associated with new particles.

4) Selection is repeated several times to yield a set of nucleic acid targeting moieties with specificity for the target tissue that is increased relative to the original library.

Nucleic acid targeting moieties that bind selectively to any in vivo and/or in vitro target can be isolated by the PICO process, provided that the target can be used as a target in the PICO process.

Agents to be Delivered

According to the present invention, inventive targeted particles may be used for delivery of any agent, including, for example, therapeutic, diagnostic, and/or prophylactic agents. Exemplary agents to be delivered in accordance with the present invention include, but are not limited to, small molecules, organometallic compounds, nucleic acids, proteins (including multimeric proteins, protein complexes, etc.), peptides, lipids, carbohydrates, hormones, metals, radioactive elements and compounds, drugs, vaccines, immunological agents, etc., and/or combinations thereof.

In some embodiments, inventive targeted particles comprise less than 50% by weight, less than 40% by weight, less than 30% by weight, less than 20% by weight, less than 15% by weight, less than 10% by weight, less than 5% by weight, less than 1% by weight, or less than 0.5% by weight of the therapeutic agent to be delivered.

In some embodiments, the agent to be delivered may be a mixture of pharmaceutically active agents. For example, a local anesthetic may be delivered in combination with an anti-inflammatory agent such as a steroid. To give but another example, an antibiotic may be combined with an inhibitor of the enzyme commonly produced by bacteria to inactivate the antibiotic (e.g., penicillin and clavulanic acid).

In some embodiments, the agent to be delivered may be a mixture of anti-cancer agents. In some embodiments, inventive targeted particles are administered in combination with one or more of the anti-cancer agents described herein. Combination therapy is described in further detail below, in the section entitled, "Administration." To give but one example, in some embodiments, inventive compositions comprising an anti-cancer agent to be delivered are administered in combination with hormonal therapy. The growth of some types of tumors can be inhibited by providing or blocking certain hormones. For example, steroids (e.g. dexamethasone) can inhibit tumor growth or associated edema and may cause regression of lymph node malignancies. In some cases, prostate cancer is often sensitive to finasteride, an agent that blocks the peripheral conversion of testosterone to dihydrotestosterone. Breast cancer cells often highly express the estrogen and/or progesterone receptor. Inhibiting the production (e.g. with aromatase inhibitors) or function (e.g. with tamoxifen) of these hormones can often be used in breast cancer treatments. In some embodiments, gonadotropin-releasing hormone agonists (GnRH), such as goserelin possess a paradoxic negative feedback effect followed by inhibition of the release of follicle stimulating hormone (FSH) and leuteinizing hormone (LH), when given continuously.

Small Molecule Agents

In some embodiments, the agent to be delivered is a small molecule and/or organic compound with pharmaceutical activity. In some embodiments, the agent is a clinically-used drug. In some embodiments, the drug is an anti-cancer agent, antibiotic, anti-viral agent, anti-HIV agent, anti-parasite agent, anti-protozoal agent, anesthetic, anticoagulant, inhibitor of an enzyme, steroidal agent, steroidal or non-steroidal anti-inflammatory agent, antihistamine, immunosuppressant agent, anti-neoplastic agent, antigen, vaccine, antibody, decongestant, sedative, opioid, analgesic, anti-pyretic, birth control agent, hormone, prostaglandin, progestational agent, anti-glaucoma agent, ophthalmic agent, anti-cholinergic, analgesic, anti-depressant, anti-psychotic, neurotoxin, hypnotic, tranquilizer, anti-convulsant, muscle relaxant, anti-Parkinson agent, anti-spasmodic, muscle contractant, channel blocker, miotic agent, anti-secretory agent, anti-thrombotic agent, anticoagulant, anti-cholinergic, β-adrenergic blocking agent, diuretic, cardiovascular active agent, vasoactive agent, vasodilating agent, anti-hypertensive agent, angiogenic agent, modulators of cell-extracellular matrix interactions (e.g. cell growth inhibitors and anti-adhesion molecules), inhibitors of DNA, RNA, or protein synthesis, etc.

In certain embodiments, the therapeutic agent to be delivered is an anti-cancer agent (i.e. cytotoxic agents). Most anti-cancer agents can be divided in to the following categories: alkylating agents, antimetabolites, natural products, and hormones and antagonists.

Anti-cancer agents typically affect cell division and/or DNA synthesis. However, some chemotherapeutic agents do not directly interfere with DNA. To give but one example, tyrosine kinase inhibitors (imatinib mesylate/Gleevec®) directly target a molecular abnormality in certain types of cancer (chronic myelogenous leukemia, gastrointestinal stromal tumors, etc.).

Alkylating agents are so named because of their ability to add alkyl groups to many electronegative groups under conditions present in cells. Alkylating agents typically function by chemically modifying cellular DNA. Exemplary alkylating agents include nitrogen mustards (e.g. mechlorethamine, cyclophosphamide, ifosfamide, melphalan (1-sarcolysin), chlorambucil), ethylenimines and methylmelamines (e.g. altretamine (hexamethylmelamine; HMM), thiotepa (triethylene thiophosphoramide), triethylenemelamine (TEM)), alkyl sulfonates (e.g. busulfan), nitrosureas (e.g. carmustine (BCNU), lomustine (CCMU), semustine (methyl-CCNU), streptozocin (streptozotocin)), and triazenes (e.g. dacarbazine (DTIC; dimethyltriazenoimidazolecarboxamide)).

Antimetabolites act by mimicking small molecule metabolites (e.g. folic acid, pyrimidines, and purines) in order to be incorporated into newly synthesized cellular DNA. Such agents also affect RNA synthesis. An exemplary folic acid analog is methotrexate (amethopterin). Exemplary pyrimidine analogs include fluorouracil (5-fluorouracil; 5-FU), floxuridine (fluorodeoxyuridine; FUdR), and cytarabine (cytosine arabinoside). Exemplary purine analogs include mercaptopurine (6-mercaptopurine; 6-MP), azathioprine, thioguanine (6-thioguanine; TG), fludarabine phosphate, pentostatin (2'-deoxycoformycin), cladribine (2-chlorodeoxyadenosine; 2-CdA), and erythrohydroxynonyladenine (EHNA).

Natural small molecule products which can be used as anti-cancer agents include plant alkaloids and antibiotics. Plant alkaloids and terpenoids (e.g. vinca alkaloids, podophyllotoxin, taxanes, etc.) typically block cell division by preventing microtubule function. Vinca alkaloids (e.g. vincristine, vinblastine (VLB), vinorelbine, vindesine, etc.) bind to tubulin and inhibit assembly of tubulin into microtubules. Vinca alkaloids are derived from the Madagascar periwinkle, *Catharanthus roseus* (formerly known as *Vinca rosea*). Podophyllotoxin is a plant-derived compound used to produce two other cytostatic therapeutic agents, etoposide and teniposide, which prevent cells from entering the G1 and S phases of the cell cycle. Podophyllotoxin is primarily obtained from the American Mayapple (*Podophyllum peltatum*) and a Himalayan Mayapple (*Podophyllum hexandrum*). Taxanes (e.g. paclitaxel, docetaxel, etc.) are derived from the Yew Tree. Taxanes enhance stability of microtubules, preventing the separation of chromosomes during anaphase.

Antibiotics which can be used as anti-cancer agents include dactinomycin (actinomycin D), daunorubicin (daunomycin; rubidomycin), doxorubicin, idarubicin, bleomycin, plicamycin (mithramycin), and mitomycin (mytomycin C).

Other small molecules which can be used as anti-cancer agents include platinum coordination complexes (e.g. cisplatin (cis-DDP), carboplatin), anthracenedione (e.g. mitoxantrone), substituted urea (e.g. hydroxyurea), methylhydrazine derivatives (e.g. procarbazine (N-methylhydrazine, MIH), and adrenocortical suppressants (e.g. mitotane (o,p'-DDD), aminoglutethimide).

Hormones which can be used as anti-cancer agents include adrenocorticosteroids (e.g. prednisone), aminoglutethimide, progestins (e.g. hydroxyprogesterone caproate, medroxyprogesterone acetate, megestrol acetate), estrogens (e.g. diethylstilbestrol, ethinyl estradiol), antiestrogen (e.g. tamoxifen), androgens (e.g. testosterone propionate, fluoxymesterone), antiandrogens (e.g. flutamide), and gonadotropin-releasing hormone analog (e.g. leuprolide).

Topoisomerase inhibitors act by inhibiting the function of topoisomerases, which are enzymes that maintain the topology of DNA. Inhibition of type I or type II topoisomerases interferes with both transcription and replication of DNA by upsetting proper DNA supercoiling. Some exemplary type I topoisomerase inhibitors include camptothecins (e.g. irinotecan, topotecan, etc.). Some exemplary type II topoisomerase inhibitors include amsacrine, etoposide, etoposide phosphate, teniposide, etc., which are semisynthetic derivatives of epipodophyllotoxins, discussed herein.

In certain embodiments, a small molecule agent can be any drug. In some embodiments, the drug is one that has already been deemed safe and effective for use in humans or animals by the appropriate governmental agency or regulatory body. For example, drugs approved for human use are listed by the FDA under 21 C.F.R. §§330.5, 331 through 361, and 440 through 460, incorporated herein by reference; drugs for veterinary use are listed by the FDA under 21 C.F.R. §§500 through 589, incorporated herein by reference. All listed drugs are considered acceptable for use in accordance with the present invention.

A more complete listing of classes and specific drugs suitable for use in the present invention may be found in *Pharmaceutical Drugs: Syntheses, Patents, Applications* by Axel Kleemann and Jurgen Engel, Thieme Medical Publishing, 1999 and the *Merck Index: An Encyclopedia of Chemicals, Drugs and Biologicals*, Ed. by Budavari et al., CRC Press, 1996, both of which are incorporated herein by reference.

Nucleic Acid Agents

In certain embodiments of the invention, an inventive targeted particle is used to deliver one or more nucleic acids (e.g. functional RNAs, functional DNAs, etc.) to a specific location such as a tissue, cell, or subcellular locale.

Functional RNA

In general, a "functional RNA" is an RNA that does not code for a protein but instead belongs to a class of RNA molecules whose members characteristically possess one or more different functions or activities within a cell. It will be appreciated that the relative activities of functional RNA molecules having different sequences may differ and may depend at least in part on the particular cell type in which the RNA is present. Thus the term "functional RNA" is used herein to refer to a class of RNA molecule and is not intended to imply that all members of the class will in fact display the activity characteristic of that class under any particular set of conditions. In some embodiments, functional RNAs include RNAi agents (e.g. short interfering RNAs (siRNAs), short hairpin RNAs (shRNAs), and microRNAs), ribozymes, tRNAs, rRNAs, RNAs useful for triple helix formation, etc.

RNAi is an evolutionarily conserved process in which presence of an at least partly double-stranded RNA molecule in a eukaryotic cell leads to sequence-specific inhibition of gene expression. RNAi was originally described as a phenomenon in which the introduction of long dsRNA (typically hundreds of nucleotides) into a cell results in degradation of mRNA containing a region complementary to one strand of the dsRNA (U.S. Pat. No. 6,506,559; and Fire et al., 1998, *Nature*, 391:806). Subsequent studies in *Drosophila* showed that long dsRNAs are processed by an intracellular RNase III-like enzyme called Dicer into smaller dsRNAs primarily comprised of two approximately 21 nucleotide (nt) strands that form a 19 base pair duplex with 2 nt 3' overhangs at each end and 5'-phosphate and 3'-hydroxyl groups (see, e.g., PCT Publication WO 01/75164; U.S. Patent Publications 2002/0086356 and 2003/0108923; Zamore et al., 2000, *Cell*, 101: 25; and Elbashir et al., 2001, *Genes Dev.*, 15:188).

Short dsRNAs having structures such as this, referred to as siRNAs, silence expression of genes that include a region that is substantially complementary to one of the two strands. This strand is referred to as the "antisense" or "guide" strand, with the other strand often being referred to as the "sense" strand. The siRNA is incorporated into a ribonucleoprotein complex termed the RNA-induced silencing complex (RISC) that contains member(s) of the Argonaute protein family. Following association of the siRNA with RISC, a helicase activity unwinds the duplex, allowing an alternative duplex to form the guide strand and a target mRNA containing a portion substantially complementary to the guide strand. An endonuclease activity associated with the Argonaute protein(s) present in RISC is responsible for "slicing" the target mRNA, which is then further degraded by cellular machinery.

Considerable progress towards the practical application of RNAi was achieved with the discovery that exogenous introduction of siRNAs into mammalian cells can effectively reduce the expression of target genes in a sequence-specific manner via the mechanism described above. A typical siRNA structure includes a 19 nucleotide double-stranded portion, comprising a guide strand and an antisense strand. Each strand has a 2 nt 3' overhang. Typically the guide strand of the siRNA is perfectly complementary to its target gene and mRNA transcript over at least 17-19 contiguous nucleotides, and typically the two strands of the siRNA are perfectly complementary to each other over the duplex portion. However, as will be appreciated by one of ordinary skill in the art, perfect complementarity is not required. Instead, one or more mismatches in the duplex formed by the guide strand and the target mRNA is often tolerated, particularly at certain positions, without reducing the silencing activity below useful levels. For example, there may be 1, 2, 3, or even more mismatches between the target mRNA and the guide strand (disregarding the overhangs). Thus, as used herein, two nucleic acid portions such as a guide strand (disregarding overhangs) and a portion of a target mRNA that are "substantially complementary" may be perfectly complementary (i.e., they hybridize to one another to form a duplex in which each nucleotide is a member of a complementary base pair) or they may have a lesser degree of complementarity sufficient for hybridization to occur. One of ordinary skill in the art will appreciate that the two strands of the siRNA duplex need not be perfectly complementary. Typically at least 80%, preferably at least 90%, or more of the nucleotides in the guide strand of an effective siRNA are complementary to the target mRNA over at least about 19 contiguous nucleotides. The effect of mismatches on silencing efficacy and the locations at which mismatches may most readily be tolerated are areas of active study (see, e.g., Reynolds et al., 2004, *Nat. Biotechnol.*, 22:326).

It will be appreciated that molecules having the appropriate structure and degree of complementarity to a target gene will exhibit a range of different silencing efficiencies. A variety of additional design criteria have been developed to assist in the selection of effective siRNA sequences. Numerous software programs that can be used to choose siRNA sequences that are predicted to be particularly effective to silence a target gene of choice are available (see, e.g., Yuan et al., 2004, *Nucl. Acids. Res.*, 32:W130; and Santoyo et al., 2005, *Bioinformatics*, 21:1376).

As will be appreciated by one of ordinary skill in the art, RNAi may be effectively mediated by RNA molecules having a variety of structures that differ in one or more respects from that described above. For example, the length of the duplex can be varied (e.g., from about 17-29 nucleotides); the overhangs need not be present and, if present, their length and the identity of the nucleotides in the overhangs can vary (though most commonly symmetric dTdT overhangs are employed in synthetic siRNAs).

Additional structures, referred to as short hairpin RNAs (shRNAs), are capable of mediating RNA interference. An shRNA is a single RNA strand that contains two complementary regions that hybridize to one another to form a double-stranded "stem," with the two complementary regions being connected by a single-stranded loop. shRNAs are processed intracellularly by Dicer to form an siRNA structure containing a guide strand and an antisense strand. While shRNAs can be delivered exogenously to cells, more typically intracellular synthesis of shRNA is achieved by introducing a plasmid or vector containing a promoter operably linked to a template for transcription of the shRNA into the cell, e.g., to create a stable cell line or transgenic organism.

While sequence-specific cleavage of target mRNA is currently the most widely used means of achieving gene silencing by exogenous delivery of short RNAi agents to cells, additional mechanisms of sequence-specific silencing mediated by short RNA species are known. For example, post-transcriptional gene silencing mediated by small RNA molecules can occur by mechanisms involving translational repression. Certain endogenously expressed RNA molecules form hairpin structures containing an imperfect duplex portion in which the duplex is interrupted by one or more mismatches and/or bulges. These hairpin structures are processed intracellularly to yield single-stranded RNA species referred to as known as microRNAs (miRNAs), which mediate translational repression of a target transcript to which they hybridize with less than perfect complementarity. siRNA-like molecules designed to mimic the structure of miRNA precursors have been shown to result in translational repression of target genes when administered to mammalian cells.

Thus the exact mechanism by which a short RNAi agent inhibits gene expression appears to depend, at least in part, on the structure of the duplex portion of the RNAi agent and/or the structure of the hybrid formed by one strand of the RNAi agent and a target transcript. RNAi mechanisms and the structure of various RNA molecules known to mediate RNAi, e.g., siRNA, shRNA, miRNA and their precursors, have been extensively reviewed (see, e.g., Dykxhhorn et al., 2003, *Nat. Rev. Mol. Cell Biol.*, 4:457; Hannon et al., 2004, *Nature*, 431:3761; and Meister et al., 2004, *Nature*, 431:343). It is to be expected that future developments will reveal additional mechanisms by which RNAi may be achieved and will reveal additional effective short RNAi agents. Any currently known or subsequently discovered short RNAi agents are within the scope of the present invention.

A short RNAi agent that is delivered according to the methods of the invention and/or is present in a composition of the invention may be designed to silence any eukaryotic gene. The gene can be a mammalian gene, e.g., a human gene. The gene can be a wild type gene, a mutant gene, an allele of a polymorphic gene, etc. The gene can be disease-associated, e.g., a gene whose over-expression, under-expression, or mutation is associated with or contributes to development or progression of a disease. For example, the gene can be oncogene. The gene can encode a receptor or putative receptor for an infectious agent such as a virus (see, e.g., Dykxhhorn et al., 2003, *Nat. Rev. Mol. Cell Biol.*, 4:457 for specific examples).

In some embodiments, tRNAs are functional RNA molecules whose delivery to eukaryotic cells can be monitored using the compositions and methods of the invention. The structure and role of tRNAs in protein synthesis is well known (Soll and Rajbhandary, (eds.) tRNA: *Structure, Biosynthesis, and Function*, ASM Press, 1995). The cloverleaf shape of tRNAs includes several double-stranded "stems" that arise as a result of formation of intramolecular base pairs between complementary regions of the single tRNA strand. There is considerable interest in the synthesis of polypeptides that incorporate unnatural amino acids such as amino acid analogs or labeled amino acids at particular positions within the polypeptide chain (see, e.g., Köhrer and RajBhandary, "Proteins carrying one or more unnatural amino acids," Chapter 33, In Ibba et al., (eds.), *Aminoacyl-tRNA Synthetases*, Landes Bioscience, 2004). One approach to synthesizing such polypeptides is to deliver a suppressor tRNA that is aminoacylated with an unnatural amino acid to a cell that expresses an mRNA that encodes the desired polypeptide but includes a nonsense codon at one or more positions. The nonsense codon is recognized by the suppressor tRNA, resulting in incorporation of the unnatural amino acid into a polypeptide encoded by the mRNA (Kohrer et al., 2001, *Proc. Natl. Acad. Sci., USA*, 98:14310; and Kohrer et al., 2004, *Nucleic Acids Res.*, 32:6200). However, as in the case of siRNA delivery, existing methods of delivering tRNAs to cells result in variable levels of delivery, complicating efforts to analyze such proteins and their effects on cells.

The invention contemplates the delivery of tRNAs, e.g., suppressor tRNAs, and optically or magnetically detectable particles to eukaryotic cells in order to achieve the synthesis of proteins that incorporate an unnatural amino acid with which the tRNA is aminoacylated. The analysis of proteins that incorporate one or more unnatural amino acids has a wide variety of applications. For example, incorporation of amino acids modified with detectable (e.g., fluorescent) moieties can allow the study of protein trafficking, secretion, etc., with minimal disturbance to the native protein structure. Alternatively or additionally, incorporation of reactive moieties (e.g., photoactivatable and/or cross-linkable groups) can be used to identify protein interaction partners and/or to define three-dimensional structural motifs. Incorporation of phosphorylated amino acids such as phosphotyrosine, phosphothreonine, or phosphoserine, or analogs thereof, into proteins can be used to study cell signaling pathways and requirements.

In one embodiment of the invention, the functional RNA is a ribozyme. A ribozyme is designed to catalytically cleave target mRNA transcripts may be used to prevent translation of a target mRNA and/or expression of a target (see, e.g., PCT publication WO 90/11364; and Sarver et al., 1990, *Science* 247:1222).

In some embodiments, endogenous target gene expression may be reduced by targeting deoxyribonucleotide sequences complementary to the regulatory region of the target gene (i.e., the target gene's promoter and/or enhancers) to form triple helical structures that prevent transcription of the target gene in target muscle cells in the body (see generally, Helene, 1991, *Anticancer Drug Des.* 6:569; Helene et al., 1992, *Ann, N.Y. Acad. Sci.* 660:27; and Maher, 1992, *Bioassays* 14:807).

RNAs such as RNAi agents, tRNAs, ribozymes, etc., for delivery to eukaryotic cells may be prepared according to any available technique including, but not limited to chemical synthesis, enzymatic synthesis, enzymatic or chemical cleavage of a longer precursor, etc. Methods of synthesizing RNA molecules are known in the art (see, e.g., Gait, M. J. (ed.) *Oligonucleotide synthesis: a practical approach*, Oxford (Oxfordshire), Washington, D.C.: IRL Press, 1984; and Herdewijn, P. (ed.) *Oligonucleotide synthesis: methods and applications*, Methods in Molecular Biology, v. 288 (Clifton, N.J.) Totowa, N.J.: Humana Press, 2005). Short RNAi agents such as siRNAs are commercially available from a number of different suppliers. Pre-tested siRNAs targeted to a wide variety of different genes are available, e.g., from Ambion (Austin, Tex.), Dharmacon (Lafayette, Colo.), Sigma-Aldrich (St. Louis, Mo.).

When siRNAs are synthesized in vitro the two strands are typically allowed to hybridize before contacting them with cells. It will be appreciated that the resulting siRNA composition need not consist entirely of double-stranded (hybridized) molecules. For example, an RNAi agent commonly includes a small proportion of single-stranded RNA. Generally, at least approximately 50%, at least approximately 90%, at least approximately 95%, or even at least approximately 99%-100% of the RNAs in an siRNA composition are double-stranded when contacted with cells. However, a composition containing a lower proportion of dsRNA may be used, provided that it contains sufficient dsRNA to be effective.

Vectors

In some embodiments, a nucleic acid to be delivered is a vector. As used herein, the term "vector" refers to a nucleic acid molecule (typically, but not necessarily, a DNA molecule) which can transport another nucleic acid to which it has been linked. A vector can achieve extra-chromosomal replication and/or expression of nucleic acids to which they are linked in a host cell (e.g. a cell targeted by targeted particles of the present invention). In some embodiments, a vector can achieve integration into the genome of the host cell.

In some embodiments, vectors are used to direct protein and/or RNA expression. In some embodiments, the protein and/or RNA to be expressed is not normally expressed by the cell. In some embodiments, the protein and/or RNA to be expressed is normally expressed by the cell, but at lower levels than it is expressed when the vector has not been delivered to the cell.

In some embodiments, a vector directs expression of any of the proteins described herein. In some embodiments, a vector directs expression of a protein with anti-cancer activity. In some embodiments, a vector directs expression of any of the functional RNAs described herein, such as RNAi agents, ribozymes, etc. In some embodiments, a vector directs expression of a functional RNA with anti-cancer activity.

Protein Agents

In some embodiments, the agent to be delivered may be a protein or peptide. In certain embodiments, peptides range from about 5 to 500, 5 to 250, 5 to 100, or 5 to 50, or 5 to 25 amino acids in size. Peptides from panels of peptides comprising random sequences and/or sequences which have been varied consistently to provide a maximally diverse panel of peptides may be used.

The terms "protein," "polypeptide," and "peptide" are used interchangeably herein, typically referring to a polypeptide having a length of less than about 500 to about 1000 amino acids. Polypeptides may contain L-amino acids, D-amino acids, or both and may contain any of a variety of amino acid modifications or analogs known in the art. Useful modifications include, e.g., terminal acetylation, amidation, etc. In some embodiments, polypeptides may comprise standard amino acids, non-standard amino acids, synthetic amino acids, and combinations thereof, as described herein.

In some embodiments, the agent to be delivered may be a peptide, hormone, erythropoietin, insulin, cytokine, antigen for vaccination, etc. In some embodiments, the agent to be delivered may be an antibody and/or characteristic portion thereof. In some embodiments, antibodies may include, but are not limited to, polyclonal, monoclonal, chimeric (i.e. "humanized"), single chain (recombinant) antibodies. In some embodiments, antibodies may have reduced effector functions and/or bispecific molecules. In some embodiments, antibodies may include Fab fragments and/or fragments produced by a Fab expression library, as described in further detail above.

In some embodiments, the agent to be delivered may be an anti-cancer agent. Exemplary protein anti-cancer agents are enzymes (e.g. L-asparaginase) and biological response modifiers, such as interferons (e.g. interferon-α), interleukins (e.g. interleukin 2; IL-2), granulocyte colony-stimulating factor (G-CSF), and granulocyte/macrophage colony-stimulating factor (GM-CSF). In some embodiments, a protein anti-cancer agent is an antibody or characteristic portion thereof which is cytotoxic to tumor cells.

Carbohydrate Agents

In some embodiments, the agent to be delivered is a carbohydrate, such as a carbohydrate that is associated with a protein (e.g. glycoprotein, proteogycan, etc.). A carbohydrate may be natural or synthetic. A carbohydrate may also be a derivatized natural carbohydrate. In certain embodiments, a carbohydrate may be a simple or complex sugar. In certain embodiments, a carbohydrate is a monosaccharide, including but not limited to glucose, fructose, galactose, and ribose. In certain embodiments, a carbohydrate is a disaccharide, including but not limited to lactose, sucrose, maltose, trehalose, and cellobiose. In certain embodiments, a carbohydrate is a polysaccharide, including but not limited to cellulose, microcrystalline cellulose, hydroxypropyl methylcellulose (HPMC), methylcellulose (MC), dextrose, dextran, glycogen, xanthan gum, gellan gum, starch, and pullulan. In certain embodiments, a carbohydrate is a sugar alcohol, including but not limited to mannitol, sorbitol, xylitol, erythritol, malitol, and lactitol.

Lipid Agents

In some embodiments, the agent to be delivered is a lipid, such as a lipid that is associated with a protein (e.g. lipoprotein). Exemplary lipids that may be used in accordance with the present invention include, but are not limited to, oils, fatty acids, saturated fatty acid, unsaturated fatty acids, essential fatty acids, cis fatty acids, trans fatty acids, glycerides, monoglycerides, diglycerides, triglycerides, hormones, steroids (e.g., cholesterol, bile acids), vitamins (e.g. vitamin E), phospholipids, sphingolipids, and lipoproteins.

In some embodiments, the lipid may comprise one or more fatty acid groups or salts thereof. In some embodiments, the fatty acid group may comprise digestible, long chain (e.g., $C_8$-$C_{50}$), substituted or unsubstituted hydrocarbons. In some embodiments, the fatty acid group may be a $C_{10}$-$C_{20}$ fatty acid or salt thereof. In some embodiments, the fatty acid group may be a $C_{15}$-$C_{20}$ fatty acid or salt thereof. In some embodiments, the fatty acid group may be a $C_{15}$-$C_{25}$ fatty acid or salt thereof. In some embodiments, the fatty acid group may be unsaturated. In some embodiments, the fatty acid group may be monounsaturated. In some embodiments, the fatty acid group may be polyunsaturated. In some embodiments, a double bond of an unsaturated fatty acid group may be in the cis conformation. In some embodiments, a double bond of an unsaturated fatty acid may be in the trans conformation.

In some embodiments, the fatty acid group may be one or more of butyric, caproic, caprylic, capric, lauric, myristic, palmitic, stearic, arachidic, behenic, or lignoceric acid. In some embodiments, the fatty acid group may be one or more of palmitoleic, oleic, vaccenic, linoleic, alpha-linolenic, gamma-linoleic, arachidonic, gadoleic, arachidonic, eicosapentaenoic, docosahexaenoic, or erucic acid.

Diagnostic Agents

In some embodiments, the agent to be delivered is a diagnostic agent. In some embodiments, diagnostic agents include gases; commercially available imaging agents used in positron emissions tomography (PET), computer assisted tomography (CAT), single photon emission computerized tomography, x-ray, fluoroscopy, and magnetic resonance imaging (MRI); anti-emetics; and contrast agents. Examples of suitable materials for use as contrast agents in MRI include gadolinium chelates, as well as iron, magnesium, manganese, copper, and chromium. Examples of materials useful for CAT and x-ray imaging include iodine-based materials.

In some embodiments, inventive targeted particles may comprise a diagnostic agent used in magnetic resonance imaging (MRI), such as iron oxide particles or gadolinium complexes. Gadolinium complexes that have been approved for clinical use include gadolinium chelates with DTPA, DTPA-BMA, DOTA and HP-DO3A (reviewed in Aime et al., 1998, *Chemical Society Reviews*, 27:19).

In some embodiments, inventive targeted particles may comprise radionuclides as therapeutic and/or diagnostic agents. Among the radionuclides used, gamma-emitters, positron-emitters, and X-ray emitters are suitable for diagnostic and/or therapy, while beta emitters and alpha-emitters may also be used for therapy. Suitable radionuclides for forming the targeted particle of the invention include, but are not limited to, $^{123}$I, $^{125}$I, $^{130}$I, $^{131}$I, $^{133}$I, $^{135}$I, $^{47}$Sc, $^{72}$As, $^{72}$Se, $^{90}$Y, $^{88}$Y, $^{97}$Ru, $^{100}$Pd, $^{101}$mRh, $^{119}$Sb, $^{128}$Ba, $^{197}$Hg, $^{211}$At, $^{212}$Bi, $^{212}$Pb, $^{109}$Pd, $^{111}$In, $^{67}$Ga, $^{68}$Ga, $^{67}$Cu, $^{75}$Br, $^{77}$Br, $^{99}$mTc, $^{14}$C, $^{13}$N, $^{15}$O, $^{32}$P, $^{33}$P, and $^{18}$F.

In some embodiments, a diagnostic agent may be a fluorescent, luminescent, or magnetic moiety. In some embodiments, a detectable moiety such as a fluorescent or luminescent dye, etc., is entrapped, embedded, or encapsulated by a particle core and/or coating layer.

Fluorescent and luminescent moieties include a variety of different organic or inorganic small molecules commonly referred to as "dyes," "labels," or "indicators." Examples include fluorescein, rhodamine, acridine dyes, Alexa dyes, cyanine dyes, etc. Fluorescent and luminescent moieties may include a variety of naturally occurring proteins and derivatives thereof, e.g., genetically engineered variants. For example, fluorescent proteins include green fluorescent protein (GFP), enhanced GFP, red, blue, yellow, cyan, and sapphire fluorescent proteins, reef coral fluorescent protein, etc. Luminescent proteins include luciferase, aequorin and derivatives thereof. Numerous fluorescent and luminescent dyes and proteins are known in the art (see, e.g., U.S. Patent Publication 2004/0067503; Valeur, B., "Molecular Fluorescence: Principles and Applications," John Wiley and Sons, 2002; *Handbook of Fluorescent Probes and Research Products*, Molecular Probes, 9$^{th}$ edition, 2002; and *The Handbook—A Guide to Fluorescent Probes and Labeling Technologies*, Invitrogen, 10$^{th}$ edition, available at the Invitrogen web site).

Prophylactic Agents

In some embodiments, the agent to be delivered is a prophylactic agent. In some embodiments, prophylactic agents include vaccines. Vaccines may comprise isolated proteins or peptides, inactivated organisms and viruses, dead organisms and virus, genetically altered organisms or viruses, and cell extracts. Prophylactic agents may be combined with interleukins, interferon, cytokines, and adjuvants such as cholera toxin, alum, Freund's adjuvant, etc. Prophylactic agents may include antigens of such bacterial organisms as *Streptococcus pnuemoniae, Haemophilus influenzae, Staphylococcus aureus, Streptococcus pyrogenes, Corynebacterium diphtheriae, Listeria monocytogenes, Bacillus anthracis, Clostridium tetani, Clostridium botulinum, Clostridium perfringens, Neisseria meningitidis, Neisseria gonorrhoeae, Streptococcus mutans, Pseudomonas aeruginosa, Salmonella typhi, Haemophilus parainfluenzae, Bordetella pertussis, Francisella tularensis, Yersinia pestis, Vibrio cholerae, Legionella pneumophila, Mycobacterium tuberculosis, Mycobacterium leprae, Treponema pallidum, Leptospirosis interrogans, Borrelia burgdorferi, Camphylobacter jejuni*, and the like; antigens of such viruses as smallpox, influenza A and B, respiratory syncytial virus, parainfluenza, measles, HIV, varicella-zoster, herpes simplex 1 and 2, cytomegalovirus, Epstein-Ban virus, rotavirus, rhinovirus, adenovirus, papillomavirus, poliovirus, mumps, rabies, rubella, coxsackieviruses, equine encephalitis, Japanese encephalitis, yellow fever, Rift Valley fever, hepatitis A, B, C, D, and E virus, and the like; antigens of fungal, protozoan, and parasitic organisms such as *Cryptococcus neoformans, Histoplasma capsulatum, Candida albicans, Candida tropicalis, Nocardia asteroides, Rickettsia ricketsii, Rickettsia typhi, Mycoplasma pneumoniae, Chlamydial psittaci, Chlamydial trachomatis, Plasmodium falciparum, Trypanosoma brucei, Entamoeba histolytica, Toxoplasma gondii, Trichomonas vaginalis, Schistosoma mansoni*, and the like. These antigens may be in the form of whole killed organisms, peptides, proteins, glycoproteins, carbohydrates, or combinations thereof.

Nutraceutical Agents

In some embodiments, the therapeutic agent to be delivered is a nutraceutical agent. In some embodiments, the nutraceutical agent provides basic nutritional value, provides health or medical benefits, and/or is a dietary supplement. In some embodiments, the nutraceutical agent is a vitamin (e.g. vitamins A, B, C, D, E, K, etc.), mineral (e.g. iron, magnesium, potassium, calcium, etc.), or essential amino acid (e.g. lysine, glutamine, leucine, etc.).

In some embodiments, nutraceutical agents may include plant or animal extracts, such as fatty acids and/or omega-3 fatty acids (e.g. DHA or ARA), fruit and vegetable extracts, lutein, phosphatidylserine, lipoid acid, melatonin, glucosamine, chondroitin, aloe vera, guggul, green tea, lycopene, whole foods, food additives, herbs, phytonutrients, antioxidants, flavonoid constituents of fruits, evening primrose oil, flaxseeds, fish and marine animal oils (e.g. cod liver oil), and probiotics.

Exemplary nutraceutical agents and dietary supplements are disclosed, for example, in Roberts et al., (*Nutriceuticals: The Complete Encyclopedia of Supplements, Herbs, Vitamins, and Healing Foods*, American Nutriceutical Association, 2001). Nutraceutical agents and dietary supplements are also disclosed in *Physicians' Desk Reference for Nutritional Supplements*, 1st Ed. (2001) and *The Physicians' Desk Reference for Herbal Medicines*, 1st Ed. (2001).

Those skilled in the art will recognize that this is an exemplary, not comprehensive, list of therapeutic agents that can be delivered using the targeted particles of the present invention. Any therapeutic agent may be associated with particles for targeted delivery in accordance with the present invention.

Production of Targeted Particles

In some embodiments, inventive targeted particles comprise a particle and one or more targeting moieties (e.g. aptamers). In certain embodiments, inventive targeted particles comprise a particle, one or more targeting moieties, and one or more therapeutic agents to be delivered.

Inventive targeted particles may be manufactured using any available method. When associating nucleic acid targeting moieties to particles, it is desirable to have a particle which can be efficiently linked to a negatively charged nucleic acid ligand using simple chemistry without adversely affecting the 3-dimensional characteristic and conformation of the nucleic acid ligand. It is desirable that the targeted particle should be able to avoid uptake by the mononuclear phagocytic system after systemic administration so that it is able to reach specific tissues and cells in the body.

In some embodiments, therapeutic agents are not covalently associated with a particle. For example, particles may comprise polymers, and therapeutic agents may be associated with the surface of, encapsulated within, and/or distributed throughout the polymer of an inventive particle. Therapeutic agents are released by diffusion, degradation of the particle, and/or combination thereof. In some embodiments, polymers degrade by bulk erosion. In some embodiments, polymers degrade by surface erosion.

In some embodiments, therapeutic agents are covalently associated with a particle. For such targeted particles, release and delivery of the therapeutic agent to a target site occurs by disrupting the association. For example, if a therapeutic agent is associated with a particle by a cleavable linker, the therapeutic agent is released and delivered to the target site upon cleavage of the linker.

In some embodiments, targeting moieties are not covalently associated with a particle. For example, particles may comprise polymers, and targeting moieties may be associated with the surface of, encapsulated within, surrounded by, and/or distributed throughout the polymer of an inventive particle. In some embodiments, targeting moieties are physically associated with a particle.

Physical association can be achieved in a variety of different ways. Physical association may be covalent or non-covalent. The particle, targeting moiety, and/or therapeutic agent may be directly associated with one another, e.g., by one or more covalent bonds, or may be associated by means of one or more linkers. In one embodiment, a linker forms one or more covalent or non-covalent bonds with the particle and one or more covalent or non-covalent bonds with the targeting moiety, thereby attaching them to one another. In some embodiments, a first linker forms a covalent or non-covalent bond with the particle and a second linker forms a covalent or non-covalent bond with the targeting moiety. The two linkers form one or more covalent or non-covalent bond(s) with each other.

In one embodiment, the linker forms one or more covalent or non-covalent bonds with the particle and one or more covalent or non-covalent bonds with the therapeutic agent, thereby attaching them to one another. In some embodiments, a first linker forms a covalent or non-covalent bond with the particle and a second linker forms a covalent or non-covalent bond with the therapeutic agent. The two linkers form one or more covalent or non-covalent bond(s) with each other.

In one embodiment, the linker forms one or more covalent or non-covalent bonds with the therapeutic agent and one or more covalent or non-covalent bonds with the targeting moiety, thereby attaching them to one another. In some embodiments, a first linker forms a covalent or non-covalent bond with the therapeutic agent and a second linker forms a covalent or non-covalent bond with the targeting moiety. The two linkers form one or more covalent or non-covalent bond(s) with each other.

Any suitable linker can be used in accordance with the present invention. Linkers may be used to form amide linkages, ester linkages, disulfide linkages, etc. Linkers may contain carbon atoms or heteroatoms (e.g., nitrogen, oxygen, sulfur, etc.). Typically, linkers are 1 to 50 atoms long, 1 to 40 atoms long, 1 to 25 atoms long, 1 to 20 atoms long, 1 to 15 atoms long, 1 to 10 atoms long, or 1 to 10 atoms long. Linkers may be substituted with various substituents including, but not limited to, hydrogen atoms, alkyl, alkenyl, alkynl, amino, alkylamino, dialkylamino, trialkylamino, hydroxyl, alkoxy, halogen, aryl, heterocyclic, aromatic heterocyclic, cyano, amide, carbamoyl, carboxylic acid, ester, thioether, alkylthioether, thiol, and ureido groups. As would be appreciated by one of skill in this art, each of these groups may in turn be substituted.

In some embodiments, a linker is an aliphatic or heteroaliphatic linker. In some embodiments, the linker is a polyalkyl linker. In certain embodiments, the linker is a polyether linker. In certain embodiments, the linker is a polyethylene linker. In certain specific embodiments, the linker is a polyethylene glycol (PEG) linker.

In some embodiments, the linker is a cleavable linker. To give but a few examples, cleavable linkers include protease cleavable peptide linkers, nuclease sensitive nucleic acid linkers, lipase sensitive lipid linkers, glycosidase sensitive carbohydrate linkers, pH sensitive linkers, hypoxia sensitive linkers, photo-cleavable linkers, heat-labile linkers, enzyme cleavable linkers (e.g. esterase cleavable linker), ultrasound-sensitive linkers, x-ray cleavable linkers, etc. In some embodiments, the linker is not a cleavable linker.

Any of a variety of methods can be used to associate a linker with a particle. General strategies include passive adsorption (e.g., via electrostatic interactions), multivalent chelation, high affinity non-covalent binding between members of a specific binding pair, covalent bond formation, etc. (Gao et al., 2005, *Curr. Op. Biotechnol.*, 16:63). In some embodiments, click chemistry can be used to associate a linker with a particle (e.g. Diels-Alder reaction, Huigsen 1,3-dipolar cycloaddition, nucleophilic substitution, carbonyl chemistry, epoxidation, dihydroxylation, etc.).

A bifunctional cross-linking reagent can be employed. Such reagents contain two reactive groups, thereby providing a means of covalently associating two target groups. The reactive groups in a chemical cross-linking reagent typically belong to various classes of functional groups such as succinimidyl esters, maleimides, and pyridyldisulfides. Exemplary cross-linking agents include, e.g., carbodiimides, N-hydroxysuccinimidyl-4-azidosalicylic acid (NHS-ASA), dimethyl pimelimidate dihydrochloride (DMP), dimethylsuberimidate (DMS), 3,3'-dithiobispropionimidate (DTBP), N-Succinimidyl 3-[2-pyridyldithio]-propionamido (SPDP), succinimidyl α-methylbutanoate, biotinamidohexanoyl-6-amino-hexanoic acid N-hydroxy-succinimide ester (SMCC), succinimidyl-[(N-maleimidopropionamido)-dodecaethyleneglycol] ester (NHS-PEO12), etc. For example, carbodiimide-mediated amide formation and active ester maleimide-mediated amine and sulfhydryl coupling are widely used approaches.

Common schemes for forming a targeted particle involve the coupling of an amine group on one molecule to a thiol group on a second molecule, sometimes by a two- or three-step reaction sequence. A thiol-containing molecule may be reacted with an amine-containing molecule using a heterobifunctional cross-linking reagent, e.g., a reagent containing both a succinimidyl ester and either a maleimide, a pyridyldisulfide, or an iodoacetamide. Amine-carboxylic acid and thiol-carboxylic acid cross-linking, maleimide-sulfhydryl coupling chemistries (e.g., the maleimidobenzoyl-N-hydroxysuccinimide ester (MBS) method), etc., may be used. Polypeptides can conveniently be attached to particles via amine or thiol groups in lysine or cysteine side chains respectively, or by an N-terminal amino group. Nucleic acids such as RNAs can be synthesized with a terminal amino group. A variety of coupling reagents (e.g., succinimidyl 3-(2-pyridyldithio)propionate (SPDP) and sulfosuccinimidyl-4-(N-maleimidomethyl)cyclohexane-1-carboxylate (sulfo-SMCC) may be used to associatethe various components of targeted particles. Particles can be prepared with functional groups, e.g., amine or carboxyl groups, available at the surface to facilitate association with a biomolecule.

Non-covalent specific binding interactions can be employed. For example, either a particle or a biomolecule can be functionalized with biotin with the other being functionalized with streptavidin. These two moieties specifically bind to each other non-covalently and with a high affinity, thereby associating the particle and the biomolecule. Other specific binding pairs could be similarly used. Alternately, histidine-tagged biomolecules can be associated with particles conjugated to nickel-nitrolotriaceteic acid (Ni-NTA).

Any biomolecule to be attached to a particle, targeting moiety, and/or therapeutic agent. The spacer can be, for example, a short peptide chain, e.g., between 1 and 10 amino acids in length, e.g., 1, 2, 3, 4, or 5 amino acids in length, a nucleic acid, an alkyl chain, etc.

For additional general information on association and/or conjugation methods and cross-linkers, see the journal *Bioconjugate Chemistry*, published by the American Chemical Society, Columbus Ohio, PO Box 3337, Columbus, Ohio, 43210; "Cross-Linking," Pierce Chemical Technical Library, available at the Pierce web site and originally published in the 1994-95 Pierce Catalog, and references cited therein; Wong S S, *Chemistry of Protein Conjugation and Cross-linking*, CRC Press Publishers, Boca Raton, 1991; and Hermanson, G. T., *Bioconjugate Techniques*, Academic Press, Inc., San Diego, 1996.

Alternatively or additionally, particles can be attached to targeting moieties directly or indirectly via non-covalent interactions. Non-covalent interactions include but are not limited to charge interactions, affinity interactions, metal coordination, physical adsorption, host-guest interactions, hydrophobic interactions, TT stacking interactions, hydrogen bonding interactions, van der Waals interactions, magnetic interactions, electrostatic interactions, dipole-dipole interactions, etc.

In some embodiments, a particle may be associated with a targeting moiety via charge interactions. For example, a particle may have a cationic surface or may be reacted with a cationic polymer, such as poly(lysine) or poly(ethylene imine), to provide a cationic surface. The particle surface can then bind via charge interactions with a negatively charged nucleic acid ligand. One end of the nucleic acid ligand is, typically, attached to a negatively charged polymer (e.g., a poly(carboxylic acid)) or an additional oligonucleotide sequence that can interact with the cationic polymer surface without disrupting the binding affinity of the nucleic acid ligand for its target.

In some embodiments, a particle may be associated with a targeting moiety and/or a therapeutic agent to be delivered via affinity interactions. For example, biotin may be attached to the surface of the controlled release polymer system and streptavidin may be attached to the nucleic acid ligand; or conversely, biotin may be attached to the nucleic acid ligand and the streptavidin may be attached to the surface of the controlled release polymer system. The biotin group and streptavidin are typically attached to the controlled release polymer system or to the nucleic acid ligand via a linker, such as an alkylene linker or a polyether linker. Biotin and streptavidin bind via affinity interactions, thereby binding the controlled release polymer system to the nucleic acid ligand.

In some embodiments, a particle may be associated with a targeting moiety and/or a therapeutic agent to be delivered via metal coordination. For example, a polyhistidine may be attached to one end of the nucleic acid ligand, and a nitrilotriacetic acid can be attached to the surface of the controlled release polymer system. A metal, such as $Ni^{2+}$, will chelate the polyhistidine and the nitrilotriacetic acid, thereby binding the nucleic acid ligand to the controlled release polymer system.

In some embodiments, a particle may be associated with a targeting moiety and/or a therapeutic agent to be delivered via physical adsorption. For example, a hydrophobic tail, such as polymethacrylate or an alkyl group having at least about 10 carbons, may be attached to one end of the nucleic acid ligand. The hydrophobic tail will adsorb onto the surface of a hydrophobic controlled release polymer system, such as a controlled release polymer system made of or coated with a polyorthoester, polysebacic anhydride, or polycaprolactone, thereby binding the nucleic acid ligand to the controlled release polymer system.

In some embodiments, a particle may be associated with a targeting moiety and/or a therapeutic agent to be delivered via host-guest interactions. For example, a macrocyclic host, such as cucurbituril or cyclodextrin, may be attached to the surface of the controlled release polymer system and a guest group, such as an alkyl group, a polyethylene glycol, or a diaminoalkyl group, may be attached to the nucleic acid ligand; or conversely, the host group may be attached to the nucleic acid ligand and the guest group may be attached to the surface of the controlled release polymer system. In one embodiment, the host and/or the guest molecule may be attached to the nucleic acid ligand or the controlled release polymer system via a linker, such as an alkylene linker or a polyether linker.

In some embodiments, a particle may be associated with a targeting moiety and/or a therapeutic agent to be delivered via hydrogen bonding interactions. For example, an oligonucleotide having a particular sequence may be attached to the surface of the controlled release polymer system, and an essentially complementary sequence may be attached to one or both ends of the nucleic acid ligand such that it does not disrupt the binding affinity of the nucleic acid ligand for its target. The nucleic acid ligand will then bind to the controlled release polymer system via complementary base pairing with the oligonucleotide attached to the controlled release polymer system. Two oligonucleotides are essentially complimentary if about 80% of the nucleic acid bases on one oligonucleotide form hydrogen bonds via an oligonucleotide base pairing system, such as Watson-Crick base pairing, reverse Watson-Crick base pairing, Hoogsten base pairing, etc., with a base on the second oligonucleotide. Typically, it is desirable for an oligonucleotide sequence attached to the controlled release polymer system to form at least about 6 complementary base pairs with a complementary oligonucleotide attached to the nucleic acid ligand.

It is to be understood that the compositions of the invention can be made in any suitable manner, and the invention is in no way limited to compositions that can be produced using the methods described herein. Selection of an appropriate method may require attention to the properties of the particular moieties being associated.

If desired, various methods may be used to separate targeted particles with an attached targeting moiety and/or therapeutic agent from targeted particles to which the targeting moiety and/or therapeutic agent has not become attached, or to separate targeted particles having different numbers of targeting moieties, or therapeutic agents attached thereto. For example, size exclusion chromatography, agarose gel electrophoresis, or filtration can be used to separate populations of targeted particles having different numbers of moieties attached thereto and/or to separate targeted particles from other entities. Some methods include size-exclusion or anion-exchange chromatography.

Any method may be used to determine whether targeted particle aggregates have formed, including measuring extinction coefficients, atomic force microscopy (AFM), etc. An extinction coefficient, generally speaking, is a measure of a substance's turbidity and/or opacity. If EM radiation can pass through a substance very easily, the substance has a low extinction coefficient. Conversely, if EM radiation hardly penetrates a substance, but rather quickly becomes "extinct" within it, the extinction coefficient is high. For example, to determine whether targeted particle aggregates have formed, EM radiation is directed toward and allowed to pass through a sample. If the sample contains primarily targeted particle aggregates, EM radiation will deflect and scatter in a pattern that is different from the pattern produced by a sample containing primarily individual targeted particles.

In general, AFM utilizes a high-resolution type of scanning probe microscope and attains resolution of fractions of an Angstrom. The microscope has a microscale cantilever with a sharp tip (probe) at its end that is used to scan a specimen surface. The cantilever is frequently silicon or silicon nitride with a tip radius of curvature on the order of nanometers. When the tip is brought into proximity of a sample surface, forces between the tip and the sample lead to a deflection of the cantilever according to Hooke's law. Typically, a feedback mechanism is employed to adjust the tip-to-sample distance to maintain a constant force between the tip and the sample. Samples are usually spread in a thin layer across a surface (e.g. mica), which is mounted on a piezoelectric tube that can move the sample in the z direction for maintaining a constant force, and the x and y directions for scanning the sample.

In general, forces that are measured in AFM may include mechanical contact force, Van der Waals forces, capillary forces, chemical bonding, electrostatic forces, magnetic forces, Casimir forces, solvation forces, etc. Typically, deflection is measured using a laser spot reflected from the top of the cantilever into an array of photodiodes. Alternatively or additionally, deflection can be measured using optical interferometry, capacitive sensing, or piezoresistive AFM probes.

Therapeutic Applications

The compositions and methods described herein can be used for the treatment and/or diagnosis of any disease, disorder, and/or condition which is associated with a tissue specific and/or cell type specific marker. Subjects include, but are not limited to, humans and/or other primates; mammals, including commercially relevant mammals such as cattle, pigs, horses, sheep, cats, and/or dogs; and/or birds, including commercially relevant birds such as chickens, ducks, geese, and/or turkeys.

Methods of Treatment

In some embodiments, targeted particles in accordance with the present invention may be used to treat, alleviate, ameliorate, relieve, delay onset of, inhibit progression of, reduce severity of, and/or reduce incidence of one or more symptoms or features of a disease, disorder, and/or condition. In some embodiments, inventive targeted particles may be used to treat cancer. In certain embodiments, inventive targeted particles may be used to treat prostate cancer.

Cancer can be associated with a variety of physical symptoms. Symptoms of cancer generally depend on the type and location of the tumor. For example, lung cancer can cause coughing, shortness of breath, and chest pain, while colon cancer often causes diarrhea, constipation, and blood in the stool. However, to give but a few examples, the following symptoms are often generally associated with many cancers: fever, chills, night sweats, cough, dyspnea, weight loss, loss of appetite, anorexia, nausea, vomiting, diarrhea, anemia, jaundice, hepatomegaly, hemoptysis, fatigue, malaise, cognitive dysfunction, depression, hormonal disturbances, neutropenia, pain, non-healing sores, enlarged lymph nodes, peripheral neuropathy, and sexual dysfunction.

In one aspect of the invention, a method for the treatment of cancer (e.g. prostate cancer) is provided. In some embodiments, the treatment of cancer comprises administering a therapeutically effective amount of inventive targeted particles to a subject in need thereof, in such amounts and for such time as is necessary to achieve the desired result. In certain embodiments of the present invention a "therapeutically effective amount" of an inventive targeted particle is that amount effective for treating, alleviating, ameliorating, relieving, delaying onset of, inhibiting progression of, reducing severity of, and/or reducing incidence of one or more symptoms or features of cancer.

In one aspect of the invention, a method for administering inventive compositions to a subject suffering from cancer (e.g. prostate cancer) is provided. In some embodiments, such methods comprise administering a therapeutically effective amount of inventive targeted particles to a subject in such amounts and for such time as is necessary to achieve the desired result (i.e. treatment of cancer). In certain embodiments of the present invention a "therapeutically effective amount" of an inventive targeted particle is that amount effective for treating, alleviating, ameliorating, relieving, delaying onset of, inhibiting progression of, reducing severity of, and/or reducing incidence of one or more symptoms or features of cancer.

Inventive therapeutic protocols involve administering a therapeutically effective amount of an inventive targeted particle to a healthy individual (i.e. a subject who does not display any symptoms of cancer and/or who has not been diagnosed with cancer). For example, healthy individuals may be "immunized" with an inventive targeted particle prior to development of cancer and/or onset of symptoms of cancer; at risk individuals (e.g., patients who have a family history of cancer; patients carrying one or more genetic mutations associated with development of cancer; patients having a genetic polymorphism associated with development of cancer; patients infected by a virus associated with development of cancer; patients with habits and/or lifestyles associated with development of cancer; etc.) can be treated substantially contemporaneously with (e.g., within 48 hours, within 24 hours, or within 12 hours of) the onset of symptoms of cancer. Of course individuals known to have cancer may receive inventive treatment at any time.

Methods of Diagnosis

In some embodiments, targeted particles of the present invention may be used to diagnose a disease, disorder, and/or condition. In some embodiments, inventive targeted particles may be used to diagnose cancer. In certain embodiments, inventive targeted particles may be used to diagnose prostate cancer. In some embodiments, such methods of diagnosis may involve the use of inventive targeted particles to physically detect and/or locate a tumor within the body of a subject.

In one aspect of the invention, a method for the diagnosis of cancer (e.g. prostate cancer) is provided. In some embodiments, the diagnosis of cancer comprises administering a therapeutically effective amount of inventive targeted particles to a subject, in such amounts and for such time as is necessary to achieve the desired result. In certain embodiments of the present invention a "therapeutically effective amount" of an inventive targeted particle is that amount effective for diagnosing cancer.

In some embodiments, inventive targeted particles comprise particles which have intrinsically detectable properties (described in further detail below). In some embodiments, inventive targeted particles comprise particles which do not have intrinsically detectable properties but are associated with a substance which is detectable.

A. Targeted Particles Comprising a Detectable Agent

In certain embodiments of the invention, the particle comprises a bulk material that is not intrinsically detectable. The particle comprises one or more fluorescent, luminescent, or magnetic moieties. For example, the particle may comprise fluorescent or luminescent substances or smaller particles of a magnetic material. In some embodiments, an optically detectable moiety such as a fluorescent or luminescent dye, etc., is entrapped, embedded, or encapsulated by a particle core and/or coating layer. Fluorescent and luminescent moieties include a variety of different organic or inorganic small molecules, as described in further detail above.

Fluorescence or luminescence can be detected using any approach known in the art including, but not limited to, spectrometry, fluorescence microscopy, flow cytometry, etc. Spectrofluorometers and microplate readers are typically used to measure average properties of a sample while fluorescence microscopes resolve fluorescence as a function of spatial coordinates in two or three dimensions for microscopic objects (e.g., less than approximately 0.1 mm diameter). Microscope-based systems are thus suitable for detecting and optionally quantitating particles inside individual cells.

Flow cytometry measures properties such as light scattering and/or fluorescence on individual cells in a flowing stream, allowing subpopulations within a sample to be identified, analyzed, and optionally quantitated (see, e.g., Mattheakis et al., 2004, *Analytical Biochemistry*, 327:200). Multiparameter flow cytometers are available. In certain embodiments of the invention, laser scanning cytometery is used (Kamentsky, 2001, *Methods Cell Biol.*, 63:51). Laser scanning cytometry can provide equivalent data to a flow cytometer but is typically applied to cells on a solid support such as a slide. It allows light scatter and fluorescence measurements and records the position of each measurement. Cells of interest may be re-located, visualized, stained, analyzed, and/or photographed. Laser scanning cytometers are available, e.g., from CompuCyte (Cambridge, Mass.).

In certain embodiments of the invention, an imaging system comprising an epifluorescence microscope equipped with a laser (e.g., a 488 nm argon laser) for excitation and appropriate emission filter(s) is used. The filters should allow discrimination between different populations of particles used in the particular assay. For example, in one embodiment, the microscope is equipped with fifteen 10 nm bandpass filters spaced to cover portion of the spectrum between 520 and 660 nm, which would allow the detection of a wide variety of different fluorescent particles. Fluorescence spectra can be obtained from populations of particles using a standard UV/visible spectrometer.

B. Targeted Particles Comprising Particles with Intrinsically Detectable Properties In some embodiments, particles have detectable optical and/or magnetic properties, though particles that may be detected by other approaches could be used. An optically detectable particle is one that can be detected within a living cell using optical means compatible with cell viability. Optical detection is accomplished by detecting the scattering, emission, and/or absorption of light that falls within the optical region of the spectrum, i.e., that portion of the spectrum extending from approximately 180 nm to several microns. Optionally a sample containing cells is exposed to a source of electromagnetic energy. In some embodiments of the invention, absorption of electromagnetic energy (e.g., light of a given wavelength) by the particle or a component thereof is followed by the emission of light at longer wavelengths, and the emitted light is detected. In some embodiments, scattering of light by the particles is detected. In certain embodiments of the invention, light falling within the visible portion of the electromagnetic spectrum, i.e., the portion of the spectrum that is detectable by the human eye (approximately 400 nm to approximately 700 nm) is detected. In some embodiments of the invention, light that falls within the infrared or ultraviolet region of the spectrum is detected.

An optical property can be a feature of an absorption, emission, or scattering spectrum or a change in a feature of an absorption, emission, or scattering spectrum. An optical property can be a visually detectable feature such as, for example, color, apparent size, or visibility (i.e. simply whether or not the particle is visible under particular conditions). Features of a spectrum include, for example, peak wavelength or frequency (wavelength or frequency at which maximum emission, scattering intensity, extinction, absorption, etc. occurs), peak magnitude (e.g., peak emission value, peak scattering intensity, peak absorbance value, etc.), peak width at half height, or metrics derived from any of the foregoing such as ratio of peak magnitude to peak width. Certain spectra may contain multiple peaks, of which one is typically the major peak and has significantly greater intensity than the others. Each spectral peak has associated features. Typically, for any particular spectrum, spectral features such as peak wavelength or frequency, peak magnitude, peak width at half height, etc., are determined with reference to the major peak. The features of each peak, number of peaks, separation between peaks, etc., can be considered to be features of the spectrum as a whole. The foregoing features can be measured as a function of the direction of polarization of light illuminating the particles; thus polarization dependence can be measured. Features associated with hyper-Rayleigh scattering can be measured. Fluorescence detection can include detection of fluorescence modes and any of the methods described herein.

Intrinsically fluorescent or luminescent particles, particles that comprise fluorescent or luminescent moieties, plasmon resonant particles, and magnetic particles are among the detectable particles that are used in various embodiments of the invention. Such particles can have a variety of different shapes including spheres, oblate spheroids, cylinders, shells, cubes, pyramids, rods (e.g., cylinders or elongated structures having a square or rectangular cross-section), tetrapods (particles having four leg-like appendages), triangles, prisms, etc. In general, the particles should have dimensions small enough to allow their uptake by eukaryotic cells. Typically the particles have a longest straight dimension (e.g., diameter) of 200 nm or less. In some embodiments, the particles have a diameter of 100 nm or less. Smaller particles, e.g., having diameters of 50 nm or less, e.g., 5-30 nm, are used in some embodiments of the invention. In some embodiments, the term "particle" encompasses atomic clusters, which have a typical diameter of 1 nm or less and generally contain from several (e.g., 3-4) up to several hundred atoms.

In certain embodiments of the invention, the particles can be quantum dots (QDs). QDs are bright, fluorescent nanocrystals with physical dimensions small enough such that the effect of quantum confinement gives rise to unique optical and electronic properties. Semiconductor QDs are often composed of atoms from groups II-VI or III-V in the periodic table, but other compositions are possible (see, e.g., Zheng et al., 2004, *Phys. Rev. Lett.*, 93:7, describing gold QDs). By varying their size and composition, the emission wavelength can be tuned (i.e., adjusted in a predictable and controllable manner) from the blue to the near infrared. QDs generally have a broad absorption spectrum and a narrow emission spectrum. Thus different QDs having distinguishable optical properties (e.g., peak emission wavelength) can be excited using a single source. QDs are brighter than most conventional fluorescent dyes by approximately 10-fold (Wu et al., 2003, *Nat. Biotechnol.*, 21:41; and Gao et al., 2004, *Nat. Biotechnol.*, 22:969) and have been significantly easier to detect than GFP among background autofluorescence in vivo (Gao et al., 2004, *Nat. Biotechnol.*, 22:969). Furthermore, QDs are less susceptible to photobleaching, fluorescing more than 20 times longer than conventional fluorescent dyes under continuous mercury lamp exposure (Derfus et al., 2004, *Advanced Materials*, 16:961).

In certain embodiments of the invention, optically detectable particles are metal particles. Metals of use in the particles include, but are not limited to, gold, silver, iron, cobalt, zinc, cadmium, nickel, gadolinium, chromium, copper, manganese, palladium, tin, and alloys thereof. Oxides of any of these metals can be used.

Noble metals (e.g., gold, silver, copper, platinum, palladium) are preferred for plasmon resonant particles, which are discussed in further detail below. For example, gold, silver, or an alloy comprising gold, silver, and optionally one or more other metals can be used. Core/shell particles (e.g., having a silver core with an outer shell of gold, or vice versa) can be used. Particles containing a metal core and a nonmetallic inorganic or organic outer shell, or vice versa, can be used. In certain embodiments, the nonmetallic core or shell comprises a dielectric material such as silica. Composite particles in which a plurality of metal particles are embedded or trapped in a nonmetal (e.g., a polymer or a silica shell) may be used. Hollow metal particles (e.g., hollow nanoshells) having an interior space or cavity are used in some embodiments. In some embodiments, a nanoshell comprising two or more concentric hollow spheres is used. Such a particle optionally comprises a core, e.g., made of a dielectric material.

In certain embodiments of the invention, at least 1%, or typically at least 5% of the mass or volume of the particle or number of atoms in the particle is contributed by metal atoms. In certain embodiments of the invention, the amount of metal in the particle, or in a core or coating layer comprising a metal, ranges from approximately 5% to 100% by mass, volume, or number of atoms, or can assume any value or range between 5 and 100%.

Certain metal particles, referred to as plasmon resonant particles, exhibit the well known phenomenon of plasmon resonance. When a metal particle (usually made of a noble metal such as gold, silver, copper, platinum, etc.) is subjected to an external electric field, its conduction electrons are displaced from their equilibrium positions with respect to the nuclei, which in turn exert an attractive, restoring force. If the electric field is oscillating (as in the case of electromagnetic radiation such as light), the result is a collective oscillation of the conduction electrons in the particle, known as plasmon resonance (Kelly et al., 2003, *J. Phys. Chem. B.*, 107:668; Schultz et al., 2000, *Proc. Natl. Acad. Sci., USA*, 97:996; and Schultz, 2003, *Curr. Op. Biotechnol.*, 14:13). The plasmon resonance phenomenon results in extremely efficient wavelength-dependent scattering and absorption of light by the particles over particular bands of frequencies, often in the visible range. Scattering and absorption give rise to a number of distinctive optical properties that can be detected using various approaches including visually (i.e., by the naked eye or using appropriate microscopic techniques) and/or by obtaining a spectrum, e.g., a scattering spectrum, extinction (scattering+absorption) spectrum, or absorption spectrum from the particle(s).

Certain lanthanide ion-doped particles exhibit strong fluorescence and are of use in certain embodiments of the invention. A variety of different dopant molecules can be used. For example, fluorescent europium-doped yttrium vanadate ($YVO_4$) particles have been produced (Beaureparie et al., 2004, *Nano Letters*, 4:2079). These particles may be synthesized in water and are readily functionalized with biomolecules.

Magnetic particles are of use in the invention. "Magnetic particles" refers to magnetically responsive particles that contain one or more metals or oxides or hydroxides thereof. Such particles typically react to magnetic force resulting from a magnetic field. The field can attract or repel the particle towards or away from the source of the magnetic field, respectively, optionally causing acceleration or movement in a desired direction in space. A magnetically detectable particle is a magnetic particle that can be detected within a living cell as a consequence of its magnetic properties. Magnetic particles may comprise one or more ferrimagnetic, ferromagnetic, paramagnetic, and/or superparamagnetic materials. Useful particles may be made entirely or in part of one or more materials selected from the group consisting of: iron, cobalt, nickel, niobium, magnetic iron oxides, hydroxides such as maghemite ($\gamma$-$Fe_2O_3$), magnetite ($Fe_3O_4$), feroxyhyte (FeO(OH)), double oxides or hydroxides of two- or three-valent iron with two- or three-valent other metal ions such as those from the first row of transition metals such as Co(II), Mn(II), Cu(II), Ni(II), Cr(III), Gd(III), Dy(III), Sm(III), mixtures of the afore-mentioned oxides or hydroxides, and mixtures of any of the foregoing. See, e.g., U.S. Pat. No. 5,916,539 for suitable synthesis methods for certain of these particles. Additional materials that may be used in magnetic particles include yttrium, europium, and vanadium.

A magnetic particle may contain a magnetic material and one or more nonmagnetic materials, which may be a metal or a nonmetal. In certain embodiments of the invention, the particle is a composite particle comprising an inner core or layer containing a first material and an outer layer or shell containing a second material, wherein at least one of the materials is magnetic. Optionally both of the materials are metals. In one embodiment, the particle is an iron oxide particle, e.g., the particle has a core of iron oxide. Optionally the iron oxide is monocrystalline. In one embodiment, the particle is a superparamagnetic iron oxide particle, e.g., the particle has a core of superparamagnetic iron oxide.

Detection of magnetic particles may be performed using any method known in the art. For example, a magnetometer or a detector based on the phenomenon of magnetic resonance (NMR) can be employed. Superconducting quantum interference devices (SQUID), which use the properties of electron-pair wave coherence and Josephson junctions to detect very small magnetic fields can be used. Magnetic force microscopy or handheld magnetic readers can be used. U.S. Patent Publication 2003/009029 describes various suitable methods. Magnetic resonance microscopy offers one approach (Wind et al., 2000, *J. Magn. Reson.*, 147:371).

In some embodiments, the use of magnetic particles allows for the use of a magnet to position the targeted particle in the vicinity of the target cell or tissue. For example, a targeted particle comprising a magnetic particle can be administered to a subject intravenously, and external magnets can be positioned so that a magnetic field is created within the body at the site of a target tissue. The magnetic particle is then drawn to the magnetic field and retained there until the magnet is removed.

Pharmaceutical Compositions

The present invention provides novel targeted particles comprising: a therapeutically effective amount of a particle, one or more targeting moieties (e.g. aptamers), and one or more therapeutic agents to be delivered; and one or more pharmaceutically acceptable excipients. In some embodiments, the present invention provides for pharmaceutical compositions comprising inventive targeted particles as described herein. Such pharmaceutical compositions may optionally comprise one or more additional therapeutically-active substances. In accordance with some embodiments, a method of administering a pharmaceutical composition comprising inventive compositions to a subject in need thereof is provided. In some embodiments, inventive compositions are administered to humans. For the purposes of the present invention, the phrase "active ingredient" generally refers to an inventive targeted particle comprising a particle, one or more targeting moieties (e.g. aptamers), and one or more therapeutic agents to be delivered.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with merely ordinary, if any, experimentation. Subjects to which administration of the pharmaceutical compositions of the invention is contemplated include, but are not limited to, humans and/or other primates; mammals, including commercially relevant mammals such as cattle, pigs, horses, sheep, cats, and/or dogs; and/or birds, including commercially relevant birds such as chickens, ducks, geese, and/or turkeys.

The formulations of the pharmaceutical compositions described herein may be prepared by any method known or hereafter developed in the art of pharmaceutics. In general, such preparatory methods include the step of bringing the active ingredient into association with one or more excipients and/or one or more other accessory ingredients, and then, if necessary and/or desirable, shaping and/or packaging the product into a desired single- or multi-dose unit.

A pharmaceutical composition of the invention may be prepared, packaged, and/or sold in bulk, as a single unit dose, and/or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

The relative amounts of the active ingredient, the pharmaceutically acceptable excipient(s), and/or any additional ingredients in a pharmaceutical composition of the invention will vary, depending upon the identity, size, and/or condition of the subject treated and further depending upon the route by which the composition is to be administered. By way of example, the composition may comprise between 0.1% and 100% (w/w) active ingredient.

Pharmaceutical formulations of the present invention may additionally comprise a pharmaceutically acceptable excipient, which, as used herein, includes any and all solvents, dispersion media, diluents, or other liquid vehicles, dispersion or suspension aids, surface active agents, isotonic agents, thickening or emulsifying agents, preservatives, solid binders, lubricants and the like, as suited to the particular dosage form desired. Remington's *The Science and Practice of Pharmacy,* 21$^{st}$ Edition, A. R. Gennaro, (Lippincott, Williams & Wilkins, Baltimore, Md., 2006) discloses various excipients used in formulating pharmaceutical compositions and known techniques for the preparation thereof. Except insofar as any conventional excipient is incompatible with a substance or its derivatives, such as by producing any undesirable biological effect or otherwise interacting in a deleterious manner with any other component(s) of the pharmaceutical composition, its use is contemplated to be within the scope of this invention.

In some embodiments, the pharmaceutically acceptable excipient is at least 95%, 96%, 97%, 98%, 99%, or 100% pure. In some embodiments, the excipient is approved for use in humans and for veterinary use. In some embodiments, the excipient is approved by United States Food and Drug Administration. In some embodiments, the excipient is pharmaceutical grade. In some embodiments, the excipient meets the standards of the United States Pharmacopoeia (USP), the European Pharmacopoeia (EP), the British Pharmacopoeia, and/or the International Pharmacopoeia.

Pharmaceutically acceptable excipients used in the manufacture of pharmaceutical compositions include, but are not limited to, inert diluents, dispersing and/or granulating agents, surface active agents and/or emulsifiers, disintegrating agents, binding agents, preservatives, buffering agents, lubricating agents, and/or oils. Such excipients may optionally be included in the inventive formulations. Excipients such as cocoa butter and suppository waxes, coloring agents, coating agents, sweetening, flavoring, and perfuming agents can be present in the composition, according to the judgment of the formulator.

Exemplary diluents include, but are not limited to, calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, etc., and combinations thereof Exemplary granulating and/or dispersing agents include, but are not limited to, potato starch, corn starch, tapioca starch, sodium starch glycolate, clays, alginic acid, guar gum, citrus pulp, agar, bentonite, cellulose and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, etc., and combinations thereof.

Exemplary surface active agents and/or emulsifiers include, but are not limited to, natural emulsifiers (e.g. acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g. bentonite [aluminum silicate] and Veegum [magnesium aluminum silicate]), long chain amino acid derivatives, high molecular weight alcohols (e.g. stearyl alcohol, cetyl alcohol, oleyl alcohol, triacetin monostearate, ethylene glycol distearate, glyceryl monostearate, and propylene glycol monostearate, polyvinyl alcohol), carbomers (e.g. carboxy polymethylene, polyacrylic acid, acrylic acid polymer, and carboxyvinyl polymer), carrageenan, cellulosic derivatives (e.g. carboxymethylcellulose sodium, powdered cellulose, hydroxymethyl cellulose, hydroxypropyl cellulose, hydroxypropyl methylcellulose, methylcellulose), sorbitan fatty acid esters (e.g. polyoxyethylene sorbitan monolaurate [Tween 20], polyoxyethylene sorbitan [Tween 60], polyoxyethylene sorbitan monooleate [Tween 80], sorbitan monopalmitate [Span 40], sorbitan monostearate [Span 60], sorbitan tristearate [Span 65], glyceryl monooleate, sorbitan monooleate [Span 80]), polyoxyethylene esters (e.g. polyoxyethylene monostearate [Myrj 45], polyoxyethylene hydrogenated castor oil, polyethoxylated castor oil, polyoxymethylene stearate, and Solutol), sucrose fatty acid esters, polyethylene glycol fatty acid esters (e.g. Cremophor), polyoxyethylene ethers, (e.g. polyoxyethylene lauryl ether [Brij 30]), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic F 68, Poloxamer 188, cetrimonium bromide, cetylpyridinium chloride, benzalkonium chloride, docusate sodium, etc. and/or combinations thereof.

Exemplary binding agents include, but are not limited to, starch (e.g. cornstarch and starch paste); gelatin; sugars (e.g.

sucrose, glucose, dextrose, dextrin, molasses, lactose, lactitol, mannitol,); natural and synthetic gums (e.g. acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum), and larch arabogalactan); alginates; polyethylene oxide; polyethylene glycol; inorganic calcium salts; silicic acid; polymethacrylates; waxes; water; alcohol; etc.; and combinations thereof.

Exemplary preservatives may include antioxidants, chelating agents, antimicrobial preservatives, antifungal preservatives, alcohol preservatives, acidic preservatives, and other preservatives. Exemplary antioxidants include, but are not limited to, alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite. Exemplary chelating agents include ethylenediaminetetraacetic acid (EDTA), citric acid monohydrate, disodium edetate, dipotassium edetate, edetic acid, fumaric acid, malic acid, phosphoric acid, sodium edetate, tartaric acid, and trisodium edetate. Exemplary antimicrobial preservatives include, but are not limited to, benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal. Exemplary antifungal preservatives include, but are not limited to, butyl paraben, methyl paraben, ethyl paraben, propyl paraben, benzoic acid, hydroxybenzoic acid, potassium benzoate, potassium sorbate, sodium benzoate, sodium propionate, and sorbic acid. Exemplary alcohol preservatives include, but are not limited to, ethanol, polyethylene glycol, phenol, phenolic compounds, bisphenol, chlorobutanol, hydroxybenzoate, and phenylethyl alcohol. Exemplary acidic preservatives include, but are not limited to, vitamin A, vitamin C, vitamin E, beta-carotene, citric acid, acetic acid, dehydroacetic acid, ascorbic acid, sorbic acid, and phytic acid. Other preservatives include, but are not limited to, tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant Plus, Phenonip, methylparaben, Germall 115, Germaben II, Neolone, Kathon, and Euxyl. In certain embodiments, the preservative is an anti-oxidant. In other embodiments, the preservative is a chelating agent.

Exemplary buffering agents include, but are not limited to, citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, etc., and combinations thereof.

Exemplary lubricating agents include, but are not limited to, magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, etc., and combinations thereof.

Exemplary oils include, but are not limited to, almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, litsea cubeba, macadamia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and combinations thereof.

Liquid dosage forms for oral and parenteral administration include, but are not limited to, pharmaceutically acceptable emulsions, microemulsions, solutions, suspensions, syrups and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the targeted particles of the invention are mixed with solubilizing agents such as Cremophor, alcohols, oils, modified oils, glycols, polysorbates, cyclodextrins, polymers, and combinations thereof.

Injectable preparations, for example, sterile injectable aqueous or oleaginous suspensions may be formulated according to the known art using suitable dispersing or wetting agents and suspending agents. The sterile injectable preparation may be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Compositions for rectal or vaginal administration are typically suppositories which can be prepared by mixing the targeted particles of this invention with suitable non-irritating excipients such as cocoa butter, polyethylene glycol or a suppository wax which are solid at ambient temperature but liquid at body temperature and therefore melt in the rectum or vaginal cavity and release the active ingredient.

Solid dosage forms for oral administration include capsules, tablets, pills, powders, and granules. In such solid dosage forms, the active ingredient is mixed with at least one inert, pharmaceutically acceptable excipient such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may comprise buffering agents.

Solid compositions of a similar type may be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally comprise opacifying agents and can be of a composition that they release the active ingredient(s) only, or preferentially, in a certain part of the intestinal tract, optionally, in a delayed manner. Examples of embedding compositions which can be used include polymeric substances and waxes. Solid compositions of a similar type may be employed as fillers in soft and hard-filled gelatin capsules using such excipients as lactose or milk sugar as well as high molecular weight polethylene glycols and the like.

The active ingredients can be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active ingredient may be admixed with at least one inert diluent such as sucrose, lactose or starch. Such dosage forms may comprise, as is normal practice, additional substances other than inert diluents, e.g., tableting lubricants and other tableting aids such a magnesium stearate and microcrystalline cellulose. In the case of capsules, tablets and pills, the dosage forms may comprise buffering agents. They may optionally comprise opacifying agents and can be of a composition that they release the active ingredient(s) only, or preferentially, in a certain part of the intestinal tract, optionally, in a delayed manner. Examples of embedding compositions which can be used include polymeric substances and waxes.

Dosage forms for topical and/or transdermal administration of a targeted particle of this invention may include ointments, pastes, creams, lotions, gels, powders, solutions, sprays, inhalants and/or patches. Generally, the active component is admixed under sterile conditions with a pharmaceutically acceptable excipient and/or any needed preservatives and/or buffers as may be required. Additionally, the present invention contemplates the use of transdermal patches, which often have the added advantage of providing controlled delivery of an active ingredient to the body. Such dosage forms may be prepared, for example, by dissolving and/or dispensing the active ingredient in the proper medium. Alternatively or additionally, the rate may be controlled by either providing a rate controlling membrane and/or by dispersing the active ingredient in a polymer matrix and/or gel.

Suitable devices for use in delivering intradermal pharmaceutical compositions described herein include short needle devices such as those described in U.S. Pat. Nos. 4,886,499; 5,190,521; 5,328,483; 5,527,288; 4,270,537; 5,015,235; 5,141,496; and 5,417,662. Intradermal compositions may be administered by devices which limit the effective penetration length of a needle into the skin, such as those described in PCT publication WO 99/34850 and functional equivalents thereof. Jet injection devices which deliver liquid vaccines to the dermis via a liquid jet injector and/or via a needle which pierces the stratum corneum and produces a jet which reaches the dermis are suitable. Jet injection devices are described, for example, in U.S. Pat. Nos. 5,480,381; 5,599,302; 5,334,144; 5,993,412; 5,649,912; 5,569,189; 5,704,911; 5,383,851; 5,893,397; 5,466,220; 5,339,163; 5,312,335; 5,503,627; 5,064,413; 5,520,639; 4,596,556; 4,790,824; 4,941,880; 4,940,460; and PCT publications WO 97/37705 and WO 97/13537. Ballistic powder/particle delivery devices which use compressed gas to accelerate vaccine in powder form through the outer layers of the skin to the dermis are suitable. Alternatively or additionally, conventional syringes may be used in the classical mantoux method of intradermal administration.

Formulations suitable for topical administration include, but are not limited to, liquid and/or semi liquid preparations such as liniments, lotions, oil in water and/or water in oil emulsions such as creams, ointments and/or pastes, and/or solutions and/or suspensions. Topically-administrable formulations may, for example, comprise from about 1% to about 10% (w/w) active ingredient, although the concentration of the active ingredient may be as high as the solubility limit of the active ingredient in the solvent. Formulations for topical administration may further comprise one or more of the additional ingredients described herein.

A pharmaceutical composition of the invention may be prepared, packaged, and/or sold in a formulation suitable for pulmonary administration via the buccal cavity. Such a formulation may comprise dry particles which comprise the active ingredient and which have a diameter in the range from about 0.5 µm to about 7 µm or from about 1 µm to about 6 µm. Such compositions are conveniently in the form of dry powders for administration using a device comprising a dry powder reservoir to which a stream of propellant may be directed to disperse the powder and/or using a self propelling solvent/powder dispensing container such as a device comprising the active ingredient dissolved and/or suspended in a low-boiling propellant in a sealed container. Such powders comprise particles wherein at least 98% of the particles by weight have a diameter greater than 0.5 μm and at least 95% of the particles by number have a diameter less than 7 μm. Alternatively, at least 95% of the particles by weight have a diameter greater than 1 μm and at least 90% of the particles by number have a diameter less than 6 μm. Dry powder compositions may include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic and/or solid anionic surfactant and/or a solid diluent (which may have a particle size of the same order as particles comprising the active ingredient).

Pharmaceutical compositions of the invention formulated for pulmonary delivery may provide the active ingredient in the form of droplets of a solution and/or suspension. Such formulations may be prepared, packaged, and/or sold as aqueous and/or dilute alcoholic solutions and/or suspensions, optionally sterile, comprising the active ingredient, and may conveniently be administered using any nebulization and/or atomization device. Such formulations may further comprise one or more additional ingredients including, but not limited to, a flavoring agent such as saccharin sodium, a volatile oil, a buffering agent, a surface active agent, and/or a preservative such as methylhydroxybenzoate. The droplets provided by this route of administration may have an average diameter in the range from about 0.1 μm to about 200 μm.

The formulations described herein as being useful for pulmonary delivery are useful for intranasal delivery of a pharmaceutical composition of the invention. Another formulation suitable for intranasal administration is a coarse powder comprising the active ingredient and having an average particle from about 0.2 to 500 micrometers. Such a formulation is administered in the manner in which snuff is taken, i.e. by rapid inhalation through the nasal passage from a container of the powder held close to the nares.

Formulations suitable for nasal administration may, for example, comprise from about as little as 0.1% (w/w) and as much as 100% (w/w) of the active ingredient, and may comprise one or more of the additional ingredients described herein. A pharmaceutical composition of the invention may be prepared, packaged, and/or sold in a formulation suitable for buccal administration. Such formulations may, for example, be in the form of tablets and/or lozenges made using conventional methods, and may, for example, 0.1 to 20% (w/w) active ingredient, the balance comprising an orally dissolvable and/or degradable composition and, optionally, one or more of the additional ingredients described herein. Alternately, formulations suitable for buccal administration may comprise a powder and/or an aerosolized and/or atomized solution and/or suspension comprising the active ingredient. Such powdered, aerosolized, and/or aerosolized formulations, when dispersed, may have an average particle and/or droplet size in the range from about 0.1 to about 200 nanometers, and may further comprise one or more of the additional ingredients described herein.

A pharmaceutical composition of the invention may be prepared, packaged, and/or sold in a formulation suitable for ophthalmic administration. Such formulations may, for example, be in the form of eye drops including, for example, a 0.1/1.0% (w/w) solution and/or suspension of the active ingredient in an aqueous or oily liquid excipient. Such drops may further comprise buffering agents, salts, and/or one or more other of the additional ingredients described herein. Other opthalmically-administrable formulations which are useful include those which comprise the active ingredient in microcrystalline form and/or in a liposomal preparation. Ear drops and/or eye drops are contemplated as being within the scope of this invention.

General considerations in the formulation and/or manufacture of pharmaceutical agents may be found, for example, in *Remington: The Science and Practice of Pharmacy* 21$^{st}$ ed., Lippincott Williams & Wilkins, 2005.

Administration

In some embodiments, a therapeutically effective amount of an inventive composition is delivered to a patient and/or organism prior to, simultaneously with, and/or after diagnosis with a disease, disorder, and/or condition. In some embodiments, a therapeutic amount of an inventive composition is delivered to a patient and/or organism prior to, simultaneously with, and/or after onset of symptoms of a disease, disorder, and/or condition. In some embodiments, the amount of inventive targeted particle is sufficient to treat, alleviate, ameliorate, relieve, delay onset of, inhibit progression of, reduce severity of, and/or reduce incidence of one or more symptoms or features of the disease, disorder, and/or condition.

The compositions, according to the method of the present invention, may be administered using any amount and any route of administration effective for treatment. The exact amount required will vary from subject to subject, depending on the species, age, and general condition of the subject, the severity of the infection, the particular composition, its mode of administration, its mode of activity, and the like. The compositions of the invention are typically formulated in dosage unit form for ease of administration and uniformity of dosage. It will be understood, however, that the total daily usage of the compositions of the present invention will be decided by the attending physician within the scope of sound medical judgment. The specific therapeutically effective dose level for any particular subject or organism will depend upon a variety of factors including the disorder being treated and the severity of the disorder; the activity of the specific active ingredient employed; the specific composition employed; the age, body weight, general health, sex and diet of the subject; the time of administration, route of administration, and rate of excretion of the specific active ingredient employed; the duration of the treatment; drugs used in combination or coincidental with the specific active ingredient employed; and like factors well known in the medical arts.

The pharmaceutical compositions of the present invention may be administered by any route. In some embodiments, the pharmaceutical compositions of the present invention are administered by a variety of routes, including oral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), transdermal, mucosal, nasal, buccal, enteral, sublingual; by intratracheal instillation, bronchial instillation, and/or inhalation; and/or as an oral spray, nasal spray, and/or aerosol. Specifically contemplated routes are systemic intravenous injection, regional administration via blood and/or lymph supply, and/or direct administration to an affected site. In some embodiments, inventive targeted particles are administered parenterally. In some embodiments, inventive targeted particles are administered intravenously. In some embodiments, inventive targeted particles are administered orally.

In some embodiments, inventive targeted particles are administered directly to an affected site. For example, inventive targeted particles may be administered locally near a tumor and/or may be administered directly to a tumor. In some embodiments, local administration refers to administration of targeted particles directly to a specific organ (e.g. injection into the prostate). In some embodiments, local administration refers to administration of targeted particles directly to a particular tissue. Local administration may be achieved via injection of targeted particles directly into a tumor or in the vicinity of a tumor. Local administration may be achieved by topical administration of targeted particles at or near the site of a tumor. Local administration may be achieved by implantation of targeted particles at or near a site of a tumor by stereotactic surgery. Local administration may be achieved by implantation of targeted particles at or near the site of a tumor during surgical removal of the tumor. In some embodiments, local administration refers to administration of targeted particles to a specific cell or population of cells (e.g. prostate cancer cells).

In general the most appropriate route of administration will depend upon a variety of factors including the nature of the agent (e.g., its stability in the environment of the gastrointestinal tract), the condition of the subject (e.g., whether the subject is able to tolerate oral administration), etc. At present the oral and/or nasal spray and/or aerosol route is most commonly used to deliver therapeutic agents directly to the lungs and/or respiratory system. However, the invention encompasses the delivery of the inventive pharmaceutical composition by any appropriate route taking into consideration likely advances in the sciences of drug delivery.

In certain embodiments, the targeted particles of the invention may be administered at therapeutic agent in amounts ranging from about 0.001 mg/kg to about 100 mg/kg, from about 0.01 mg/kg to about 50 mg/kg, from about 0.1 mg/kg to about 40 mg/kg, from about 0.5 mg/kg to about 30 mg/kg, from about 0.01 mg/kg to about 10 mg/kg, from about 0.1 mg/kg to about 10 mg/kg, or from about 1 mg/kg to about 25 mg/kg, of subject body weight per day, one or more times a day, to obtain the desired therapeutic effect. The desired dosage may be delivered three times a day, two times a day, once a day, every other day, every third day, every week, every two weeks, every three weeks, or every four weeks. In certain embodiments, the desired dosage may be delivered using multiple administrations (e.g., two, three, four, five, six, seven, eight, nine, ten, eleven, twelve, thirteen, fourteen, or more administrations).

In some embodiments, the present invention encompasses "therapeutic cocktails" comprising inventive targeted particles. In some embodiments, the targeted particles comprise a single species of targeting moiety which can bind to multiple targets. In some embodiments, different targeted particles comprise different targeting moiety species, and all of the different targeting moiety species can bind to the same target. In some embodiments, different targeted particles comprise different targeting moiety species, and all of the different targeting moiety species can bind to different targets. In some embodiments, such different targets may be associated with the same cell type. In some embodiments, such different targets may be associated with different cell types.

It will be appreciated that targeted particles and pharmaceutical compositions of the present invention can be employed in combination therapies. The particular combination of therapies (therapeutics or procedures) to employ in a combination regimen will take into account compatibility of the desired therapeutics and/or procedures and the desired therapeutic effect to be achieved. It will be appreciated that the therapies employed may achieve a desired effect for the same purpose (for example, an inventive targeted particle useful for detecting tumors may be administered concurrently with another agent useful for detecting tumors), or they may achieve different effects (e.g., control of any adverse effects).

Pharmaceutical compositions of the present invention may be administered either alone or in combination with one or more other therapeutic agents. By "in combination with," it is not intended to imply that the agents must be administered at the same time and/or formulated for delivery together, although these methods of delivery are within the scope of the invention. The compositions can be administered concurrently with, prior to, or subsequent to, one or more other desired therapeutics or medical procedures. In general, each agent will be administered at a dose and/or on a time schedule determined for that agent. Additionally, the invention encompasses the delivery of the inventive pharmaceutical compositions in combination with agents that may improve their bioavailability, reduce and/or modify their metabolism, inhibit their excretion, and/or modify their distribution within the body.

The particular combination of therapies (therapeutics and/or procedures) to employ in a combination regimen will take into account compatibility of the desired therapeutics and/or procedures and/or the desired therapeutic effect to be achieved. It will be appreciated that the therapies employed may achieve a desired effect for the same disorder (for example, an inventive targeted particle may be administered concurrently with another therapeutic agent used to treat the same disorder), and/or they may achieve different effects (e.g., control of any adverse effects). In some embodiments, targeted particles of the invention are administered with a second therapeutic agent that is approved by the U.S. Food and Drug Administration.

In will further be appreciated that therapeutically active agents utilized in combination may be administered together in a single composition or administered separately in different compositions.

In general, it is expected that agents utilized in combination with be utilized at levels that do not exceed the levels at which they are utilized individually. In some embodiments, the levels utilized in combination will be lower than those utilized individually.

In some embodiments, inventive compositions may be administered in combination with any therapeutic agent or therapeutic regimen that is useful to treat, alleviate, ameliorate, relieve, delay onset of, inhibit progression of, reduce severity of, and/or reduce incidence of one or more symptoms or features of cancer. For example, inventive compositions may be administered in combination with traditional cancer therapies including, but not limited to, surgery, chemotherapy, radiation therapy, hormonal therapy, immunotherapy, complementary or alternative therapy, and any combination of these therapies.

In some embodiments, inventive compositions are administered in combination with surgery to remove a tumor. Because complete removal of a tumor with minimal or no damage to the rest of a patient's body is typically the goal of cancer treatment, surgery is often performed to physically remove part or all of a tumor. If surgery is unable to completely remove a tumor, additional therapies (e.g. chemotherapy, radiation therapy, hormonal therapy, immunotherapy, complementary or alternative therapy) may be employed.

In some embodiments, inventive compositions are administered in combination with radiation therapy. Radiation therapy (also known as radiotherapy, X-ray therapy, or irradiation) is the use of ionizing radiation to kill cancer cells and shrink tumors. Radiation therapy may be used to treat almost any type of solid tumor, including cancers of the brain, breast, cervix, larynx, lung, pancreas, prostate, skin, stomach, uterus, or soft tissue sarcomas. Radiation can be used to treat leukemia and lymphoma. Radiation therapy can be administered externally via external beam radiotherapy (EBRT) or internally via brachytherapy. Typically, the effects of radiation therapy are localized and confined to the region being treated. Radiation therapy injures or destroys tumor cells in an area being treated (e.g. a target organ, tissue, and/or cell) by damaging their genetic material, preventing tumor cells from growing and dividing. In general, radiation therapy attempts to damage as many tumor cells as possible while limiting harm to nearby healthy tissue. Hence, it is often administered in multiple doses, allowing healthy tissue to recover between fractions.

In some embodiments, inventive compositions are administered in combination with immunotherapy. Immunotherapy is the use of immune mechanisms against tumors which can be used in various forms of cancer, such as breast cancer (e.g. trastuzumab/Herceptin®), leukemia (e.g. gemtuzumab ozogamicin/Mylotarg®), and non-Hodgkin's lymphoma (e.g. rituximab/Rituxan®). In some embodiments, immunotherapy agents are monoclonal antibodies directed against proteins that are characteristic to the cells of the cancer in question. In some embodiments, immunotherapy agents are cytokines that modulate the immune system's response. In some embodiments, immunotherapy agents may be vaccines.

In some embodiments, vaccines can be administered to prevent and/or delay the onset of cancer. In some embodiments, cancer vaccines prevent and/or delay the onset of cancer by preventing infection by oncogenic infectious agents. In some embodiments, cancer vaccines prevent and/or delay the onset of cancer by mounting an immune response against cancer-specific epitopes. To give but one example of a cancer vaccine, an experimental vaccine for HPV types 16 and 18 was shown to be 100% successful at preventing infection with these types of HPV and, thus, are able to prevent the majority of cervical cancer cases (Harper et al., 2004, *Lancet*, 364:1757).

In some embodiments, inventive compositions are administered in combination with complementary and alternative medicine treatments. Some exemplary complementary measures include, but are not limited to, botanical medicine (e.g. use of mistletoe extract combined with traditional chemotherapy for the treatment of solid tumors); acupuncture for managing chemotherapy-associated nausea and vomiting and in controlling pain associated with surgery; prayer; psychological approaches (e.g. "imaging" or meditation) to aid in pain relief or improve mood. Some exemplary alternative measures include, but are not limited to, diet and other lifestyle changes (e.g. plant-based diet, the grape diet, and the cabbage diet).

In some embodiments, inventive compositions are administered in combination with any of the traditional cancer treatments described herein, which are often associated with unpleasant, uncomfortable, and/or dangerous side effects. For example, chronic pain often results from continued tissue damage due to the cancer itself or due to the treatment (i.e., surgery, radiation, chemotherapy). Alternatively or additionally, such therapies are often associated with hair loss, nausea, vomiting, diarrhea, constipation, anemia, malnutrition, depression of immune system, infection, sepsis, hemorrhage, secondary neoplasms, cardiotoxicity, hepatotoxicity, nephrotoxicity, ototoxicity, etc. Thus, inventive compositions which are administered in combination with any of the traditional cancer treatments described herein may be also be administered in combination with any therapeutic agent or therapeutic regimen that is useful to treat, alleviate, ameliorate, relieve, delay onset of, inhibit progression of, reduce severity of, and/or reduce incidence of one or more side effects of cancer treatment. To give but a few examples, pain can be treated with opioids and/or analgesics (e.g. morphine, oxycodone, antiemetics, etc.); nausea and vomiting can be treated with 5-HT$_3$ inhibitors (e.g. dolasetron/Anzemet®, granisetron/Kytril®, ondansetron/Zofran®, palonsetron/Aloxi®) and/or substance P inhibitors (e.g. aprepitant/Emend®); immunosuppression can be treated with a blood transfusion; infection and/or sepsis can be treated with antibiotics (e.g. penicillins, tetracyclines, cephalosporins, sulfonamides, aminoglycosides, etc.); and so forth.

In some embodiments, inventive compositions may be administered and/or inventive diagnostic methods may be performed in combination with any therapeutic agent or therapeutic regimen that is useful to diagnose one or more symptoms or features of cancer (e.g. detect the presence of and/or locate a tumor). In some embodiments, inventive targeted particles may be used in combination with one or more other diagnostic agents. To give but one example, targeted particles used to detect tumors may be administered in combination with other agents useful in the detection of tumors. For example, inventive targeted particles may be administered in combination with traditional tissue biopsy followed by immunohistochemical staining and serological tests (e.g. prostate serum antigen test). Alternatively or additionally, inventive targeted particles may be administered in combination with a contrasting agent for use in computed tomography (CT) scans and/or MRI.

Kits

The invention provides a variety of kits comprising one or more of the targeted particles of the invention. For example, the invention provides a kit comprising an inventive targeted particle and instructions for use. A kit may comprise multiple different targeted particles. A kit may comprise any of a number of additional components or reagents in any combination. All of the various combinations are not set forth explicitly but each combination is included in the scope of the invention.

According to certain embodiments of the invention, a kit may include, for example, (i) a targeted particle comprising a particle, a specific targeting moiety, and one or more particular therapeutic agents to be delivered; (ii) instructions for administering the targeted particle to a subject in need thereof.

According to certain embodiments of the invention, a kit may be provided which includes materials useful for identifying and/or screening for novel targeting moieties. Such a kit may include, for example, (i) a targeted particle comprising a particle, a library of targeting moieties, and one or more therapeutic agents to be delivered; (ii) a targeted particle that may serve as a positive control; (iii) a targeted particle that may serve as a negative control. In some embodiments, a targeted particle that may serve as a positive control may comprise a targeting moiety that is already known to target a specific organ, tissue, cell, intracellular compartment, etc. In some embodiments, a targeted particle that may serve as a positive control may comprise a therapeutic agent that is already known to treat and/or diagnose a particular disease, disorder, and/or condition. In some embodiments, a targeted particle that may serve as a negative control may comprise a targeting moiety that is already known not to target a specific target (e.g. a target associated with a particular organ, tissue, cell, intracellular compartment, etc.). In some embodiments, a targeted particle that may serve as a negative control may comprise a therapeutic agent that is already known not to treat and/or diagnose a particular disease, disorder, and/or condition. In some embodiments, a targeted particle that may serve as a negative control may comprise an targeting moiety that is already known to target a specific target (e.g., a target associated with a particular organ, tissue, cell, intracellular compartment, etc., but does not comprise a therapeutic agent. In some embodiments, a targeted particle that may serve as a negative control may comprise a therapeutic agent that is already known to treat and/or diagnose a particular disease, disorder, and/or condition, but does not comprise a targeting moiety.

Kits typically include instructions for use of inventive targeted particles. Instructions may, for example, comprise protocols and/or describe conditions for production of targeted particles, administration of targeted particles to a subject in need thereof, design of novel targeted particles, etc. Kits will generally include one or more vessels or containers so that some or all of the individual components and reagents may be separately housed. Kits may also include a means for enclosing individual containers in relatively close confinement for commercial sale, e.g., a plastic box, in which instructions, packaging materials such as styrofoam, etc., may be enclosed. An identifier, e.g., a bar code, radio frequency identification (ID) tag, etc., may be present in or on the kit or in or one or more of the vessels or containers included in the kit. An identifier can be used, e.g., to uniquely identify the kit for purposes of quality control, inventory control, tracking, movement between workstations, etc.

EXEMPLIFICATION

Example 1

Formulation of Functionalized PLGA-PEG Nanoparticles for In Vivo Targeted Drug Delivery Materials and Methods
 Materials
 Docetaxel and $^{14}$C-paclitaxel were purchased from Sigma-Aldrich (St. Louis, Mo.). Poly($_{D,L}$-lactide-co-glycolide) (50/50) with terminal carboxylate groups (PLGA, inherent viscosity 0.20 dL/g in hexafluoroisopropanol, MW approximately 17 kDa) was obtained from Absorbable Polymers International (Pelham, Ala.). NH$_2$-PEG-COOH (MW 3400) was purchased from Nektar Therapeutics (San Carlos, Calif.). All reagents were analytical grade or above and used as received, unless otherwise stated. Molecular biology buffers were purchased from Boston BioProducts (Worcester, Mass.). Tissue culture reagents and the LNCaP cell line were obtained from American Type Culture Collection (Manassas, Va.). RNA aptamer (sequence: 5'-NH$_2$-spacer-[GGG/AGG/ACG/AUG/CGG/AUC/AGC/CAU/GUU/UAC/GUC/ACU/CCU/UGU/CAA/UCC/UCA/UCG/GCiT-3'(SEQ ID NO.: 3)] with 2'-fluoro pyrimidines, a 5'-amino group attached by a hexaethyleneglycol spacer and a 3'-inverted T cap) was custom synthesized by RNA-TEC (Leuven, Belgium) at a purity above 90%.
 Synthesis of PLGA-b-PEG
 Carboxylate-functionalized copolymer PLGA-b-PEG was synthesized by the attachment of COOH-PEG-NH$_2$ to PLGA-COOH. PLGA-COOH (5 g, 0.28 mmol) in methylene chloride (10 mL) was converted to PLGA-NHS with excess N-hydroxysuccinimide (NHS, 135 mg, 1.1 mmol) in the presence of 1-ethyl-3-(3-dimethylaminopropyl)-carbodiimide (EDC, 230 mg, 1.2 mmol). PLGA-NHS was precipitated with ethyl ether (5 mL), and repeatedly washed in an ice-cold mixture of ethyl ether and methanol to remove residual NHS. After drying under vacuum, PLGA-NHS (1 g, 0.059 mmol) was dissolved in chloroform (4 mL) followed by addition of NH$_2$-PEG-COOH (250 mg, 0.074 mmol) and N,N-diisopropylethylamine (28 mg, 0.22 mmol). The co-polymer was precipitated with cold methanol after 12 hours and washed with the same solvent (3×5 mL) to remove unreacted PEG. The resulting PLGA-PEG block co-polymer was dried under vacuum and used for nanoparticle (NP) preparation without further treatment. $^1$H NMR (CDCl$_3$ at 300 Hz) δ 5.2 (m, ((OCH(CH$_3$)C(O)OCH$_2$C(O))$_n$—(CH$_2$CH$_2$O)$_m$), 4.8 (m, ((OCH(CH$_3$)C(O)OCH$_2$C(O))$_n$—(CH$_2$CH$_2$O)$_m$), 3.7 (s, ((OCH(CH$_3$)C(O)OCH$_2$C(O))$_n$—(CH$_2$CH$_2$O)$_m$), 1.6 (d, ((OCH(CH$_3$)C(O)OCH$_2$C(O))$_n$—(CH$_2$CH$_2$O)$_m$).
 Formulation of Taxane Drug-Loaded PLGA-b-PEG NPs
 The nanoprecipitation method was employed for the formation of drug-encapsulated carboxylated PLGA-b-PEG NPs, similarly to previously described (Farokhzad et al., 2006, Proc. Natl. Acad. Sci., USA, 103:6315; and Fonseca et al., 2002, J. Control. Release, 83:273). Briefly, docetaxel (or $^{14}$C-paclitaxel) was dissolved in various organic solvents that are miscible with water. Polymer was likewise dissolved and mixed with the drug. NPs were formed by adding the drug-polymer solution to water, a non-solvent. The resulting NP suspension was allowed to stir uncovered for 6 hours at room temperature. NPs were purified by centrifugation (10 minutes at 10,000×g) or by ultrafiltration (15 minutes at 3000×g, Amicon Ultra, Ultracel membrane with 100,000 NMWL, Millipore, Billerica, Mass.). PLGA-b-PEG NPs were re-suspended, washed with water, and collected likewise.
 Parameters controlling formation of NPs were systematically varied in this study. Generally, the starting formulation was as follows: PLGA-b-PEG (10 mg/mL) and docetaxel (0.1 mg/mL) were dissolved in acetonitrile. The mixture was added dropwise to a 2× volume of stirring water. NPs were produced with the nanoprecipitation method in four solvents: N,N-dimethylformamide (DMF), acetone, acetonitrile, and tetrahydrofuran (THF). Effects of the various solvents were assayed on the overall size of NPs. For each solvent, the ratio of solvent to water was varied from 0.1 to 1.0 (using 10 mg/mL polymer for each). Further, a range of polymer concentrations in the organic phase from 5 mg/mL to 50 mg/mL was used for formation of NPs in a 2× volume of water. NPs were processed as above in triplicate, noting trends in formulation parameters. In another study, NPs containing variable amounts of docetaxel were synthesized by adjusting docetaxel drug loading from 0% to 10% by weight of the added polymer, formulating NPs from 10 mg/mL polymer in acetonitrile and a 2× volume of water.
 NP post-formulation stability was studied for both the purification and particle formation steps, and through the storage in solid-state after freeze-drying. NPs were also flash-frozen in liquid nitrogen prior to lyopholization for freeze-drying.
 Determination of Particle Sizes and Polydispersities
 Particle size distributions were measured by dynamic light scattering (Brookhaven Instruments Corporation 90 plus Particle Sizer, 676 nm laser) at 25° C. and at a scattering angle of 90° at a concentration of approximately 1 mg NP/mL water. Intensity-weighted mean value was recorded as the average of three measurements.
 Determination of Drug Content
 NPs were dissolved in acetonitrile and measured by HPLC in triplicate to determine docetaxel content. The Agilent 1100 HPLC (Palo Alto, Calif.) was equipped with a UV detector and a reverse-phase pentafluorophenyl column (Curosil-PFP, 250×4.6 mm, 5μ, Phenomenex, Torrance, Calif.) with a non-gradient mobile phase of water and acetonitrile (v/v 50/50) at a constant flow rate 1 mL/minute. The docetaxel peak was measured at a wavelength of 227 nm and quantitatively determined by comparing with a standard curve.

Association of Aptamer with PLGA-b-PEG-COOH NPs

PLGA-b-PEG NPs (10 µg/µL) were suspended in water and were incubated with EDC (400 mM) and NHS (200 mM) for 20 minutes. NPs were then repeatedly washed in DNase-, RNase-free water (3×15 mL) followed by ultrafiltration. NHS-activated NPs were reacted with a 5'-amino-RNA aptamer (1 µg/µL). The resulting NP-Apt targeted particles were washed with ultrapure water (15 mL) by ultrafiltration, and surface-bound aptamers were denatured at 90° C. and allowed to assume binding conformation during snap-cooling on ice. NP suspensions were kept at 4° C. until use.

NP-Apt bioassociation was confirmed on 10% TBE-Urea PAGE. NPs were incubated as above with (+EDC) and without (−EDC) crosslinker to confirm covalent association. Aptamer, NP, NP+Apt (+EDC), NP+Apt (−EDC), washed NP+Apt (+EDC), and washed NP+Apt (−EDC) were separated by PAGE. The molecular weight (MW) DNA marker and free aptamer served as standards for a 57 base pair band on the gel.

In vivo Tumor Targeting and Biodistribution of NP-Apt Targeted Particles

All animal studies were carried out under the supervision of MIT's Division of Comparative Medicine and in compliance with NIH's *Principles of Laboratory Animal Care*. Human xenograft prostate cancer tumors were induced in 8-week old balb/c nude mice (Charles River Laboratories, Wilmington, Mass.). Mice were injected subcutaneously in the right flank with 3×10$^6$ LNCaP cells (i.e. cell line established from a metastatic lesion of human prostatic adenocarcinoma) suspended in a 1:1 mixture of media and matrigel (BD Biosciences, Franklin Lakes, N.J.). Prior to use in tumor induction, LNCaP cells were cultured in RPMI-1640 medium supplemented with 10% fetal bovine serum, 100 units/mL penicillin G, and 100 µg/mL streptomycin.

Tumor targeting studies were carried out after the mice developed approximately 100 mg tumors. Mice were divided into groups of four, minimizing tumor size variations between groups. Mice were anesthesized by intraperitoneal injection of avertin (200 mg/kg body weight), and dosed with NPs or NP-Apt targeted particles by retro-orbital injection. NPs were traced by encapsulating $^{14}$C-paclitaxel and suspended in 200 µL PBS (1×) prior to administration. Different groups were euthanized at 2, 6 or 24 hours, and 200 µL of blood was drawn by cardiac puncture from each mouse. The tumor, heart, lungs, liver, spleen and kidneys were harvested from each animal. $^{14}$C content of tissues was assayed in a Packard Tri-Carb Scintillation Analyser (Downers Grove, Ill.). Tissues were solubilized in Solvable (Packard), and activity was counted in Hionic-Fluor scintillation cocktail (PerkinElmer, Boston, Mass.). The liver from each mouse was homogenized due to its large size, and approximately 100 mg of tissue was placed in a scintillation vial for analysis. The other organs were placed directly in scintillation vials. Each organ was solubilized in 2 mL Solvable for approximately 12 hours at 60° C., and the resulting solution was de-colored with 200 µL hydrogen peroxide for 1 hour at 60° C. For the blood, 400 µL Solvable was added, and the vials were otherwise treated similarly to the tissues. To determine 100% dose, vials of the formulated NPs were counted along with the tissues. Data are presented as percent injected dose per gram of tissue.

Statistical Analysis

Statistical analysis of samples was undertaken using a student's t-test, and p-values<0.05 were considered to be statistically significant. All data reported are means+/−standard deviations, unless otherwise noted.

Results

Synthesis of PLGA-b-PEG Copolymer

Carboxyl-functionalized PLGA-b-PEG copolymer was synthesized by covalent modification of PLGA-COOH with NH$_2$-PEG-COOH, both having fixed block length, to generate PLGA-b-PEG-COOH (FIG. 1). The carboxyl group in the copolymer is at the terminal end of the hydrophilic PEG block; therefore, upon NP formulation, PEG should facilitate the presentation of the carboxyl groups on the nanoparticle surface making it available for surface chemistry. RNA aptamers are synthesized with 5'-amino groups that can be covalently associated with the carboxyl groups on the NP surface using carbodiimide coupling chemistry (FIG. 1). After preparing the polymer, the efficiency of the coupling reaction was determined by $^1$H NMR, which revealed that approximately 83% of PLGA was associated with the PEG segment.

Effects of Varying Formulation Parameters to Control Nanoparticle Size

Figure 2:
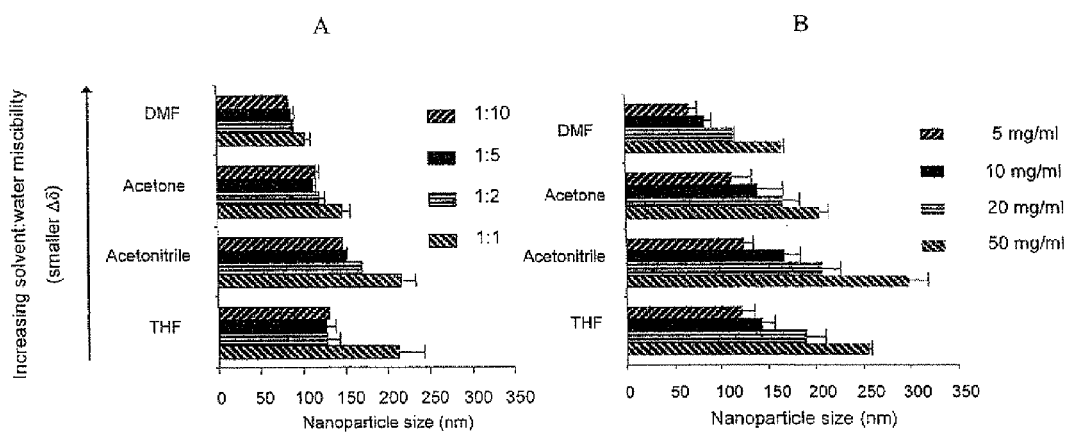
FIG. 2: Effect of varying formulation parameters on nanoparticle size. (A) Varying solvent:water ratio (1:1, 1:2, 1:5, 1:10) while keeping PLGA-b-PEG polymer constant at 10 mg/ml. (B) Varying polymer concentrations in organic phase (5, 10, 20, or 50 mg/ml) while keeping solvent:water ratio constant at 1:2.

As a starting point for controlling NP size distribution, the effect of varying the type of organic solvent used to solubilize the drug and polymer was analyzed. Previous studies have suggested that the miscibility of the organic solvent in water can impact NP size for a given solvent:water system (Galindo-Rodriguez et al., 2004, *Pharm. Res.*, 21:1428; and Bilati et al., 2005, *Eur. J. Pharm. Sci.*, 24:67). Generally, miscibility can be quantitatively expressed by comparing solubility parameters (δ) of both solvent and water (Yu et al., *General principles governing dissolution of materials in solvents*, ChemTec Publishing, 2001). As solvents become more miscible, the difference in solubility parameters between the solvents (Δδ) is minimized. The relationship of NP size and solvent miscibility with water was measured using four organic solvents, a dependence of NP size on the solubility parameters was observed. As shown in FIG. 2, sizes of PLGA-b-PEG NPs and water-miscibility of the four organic solvents used in this study were generally correlated; an increase of water miscibility (decrease in Δδ, as indicated by the arrow shown in FIG. 2) led to a decrease in the mean NP size, with all other formulation parameters held constant. NPs prepared in DMF, the most water miscible solvent tested, resulted in the smallest particles. Without wishing to be bound to any particular theory, this may be due to more efficient solvent diffusion and polymer dispersion into water.

In conjunction with the investigation of the effect of solvent-water miscibility, the effect of altering the solvent:water ratio during NP formulation was analyzed. When solvent:water ratios were varied for a fixed polymer concentration (10 mg/mL) as shown in FIG. 2A, no clear correlation of particle size with solvent-to-water ratio was observed. Most of the NP sizes remained relatively unchanged when the ratio was in a range of 0.1-0.5. In acetone, for example, NP sizes increased from 115.3±5.1 nm to 120.9±6.9 nm as the $V_{solvent}/V_{water}$ ratio increased from 0.1 to 0.5, respectively (mean±s.d., n=3 for each formulation; p>0.05). For THF, the size remained consistent as the ratio was varied from 0.1 to 0.5, with respective sizes of 130±0.5 nm and 129±15.5 nm. At the solvent:water ratio of 1.0, a large increase in particle size was observed. Without wishing to be bound by any particular theory, this is presumably due to poor phase separation—NPs formulated in acetonitrile and THF were sized greater than 200 nm (p<0.05, comparing sizes for ratio of 1 vs. 0.5).

Figure 3:
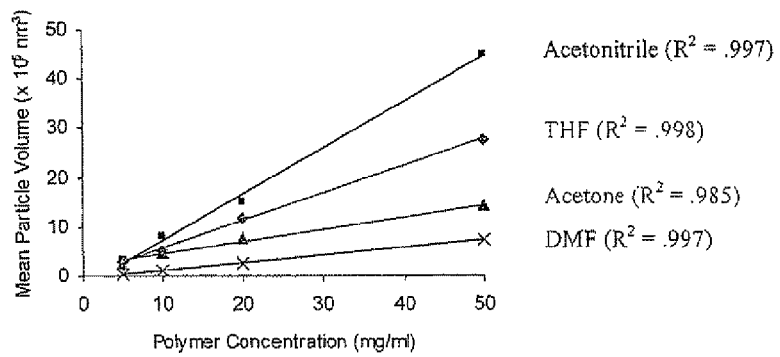
FIG. 3: Correlation of nanoparticle volumetric sizes with polymer concentrations at constant solvent:water ratio.

When polymer concentrations were varied during NP formulation at a fixed solvent:water ratio (FIG. 2B), a trend of increasing NP size with increasing polymer concentration was observed. For example, NP sizes increased from 69.0 nm to 165.0 nm in DMF as the polymer concentration increased 10 times from 5 mg/mL to 50 mg/mL. Similar trends were observed in all other solvents investigated. Interpreting data in terms of changes in volumetric size showed linear agreement between size and polymer concentration. The $R^2$ values for the plot of mean NP volume and polymer concentration (FIG. 3) were 0.997, 0.985, 0.998, and 0.997 for DMF, acetone, THF, and acetonitrile, respectively. For the inventive polymer system, using the linear correlation of the NP volumetric size and polymer concentration allows for formulation of NP with predefined, desired sizes.

Nanoparticle Polydispersity at Different Drug Loadings

Figure 4:
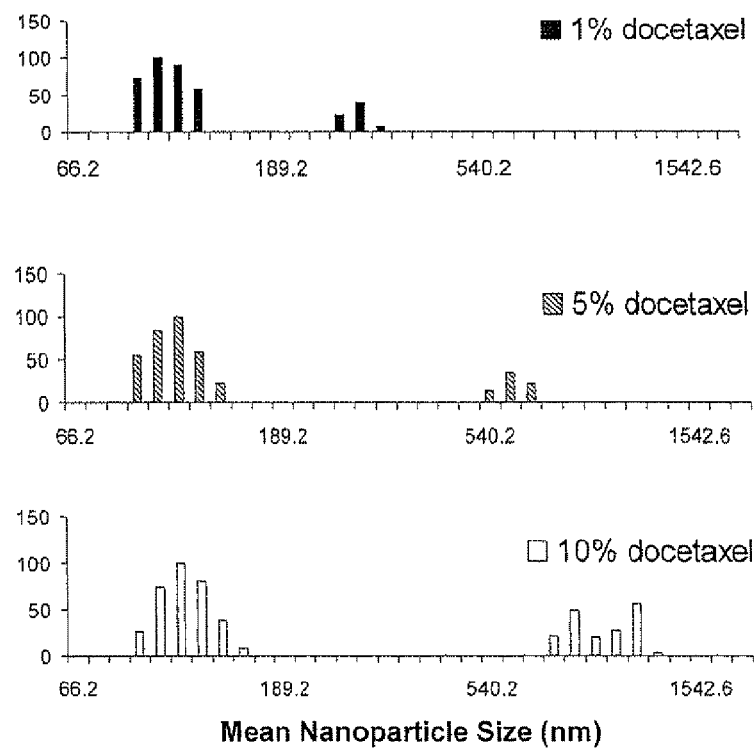
FIG. 4: Effect of docetaxel loading on PLGA-b-PEG nanoparticle polydispersity.

The effect of docetaxel loading on resulting NP size distributions was analyzed, comparing NPs loaded with 1%, 5% and 10% docetaxel. For a given NP formulation (150 nm NPs), the polydispersity of the particle preparations increased with docetaxel concentration as follows: from 0.154 for the 1% loading to 0.203 for the 5% loading and 0.212 for the 10% loading. The size distribution of NPs exhibited a biphasic trend with a smaller diameter particle distribution accompanied by a distribution of larger diameter particles (FIG. 4). The distribution corresponding to smaller particles did not shift with the increase of drug concentration. The larger diameter locus of the two size distributions shifted higher as the drug loading increased (the size increasing from approximately 300 nm to 1200 nm, FIG. 4). Since the only difference between these formulations is the amount of drug loading, a significant amount of the NPs formed may be due to aggregation of unencapsulated docetaxel, due to its poor water solubility.

Control of Nanoparticle Size During Post-Formulation Treatment

Figure 5:
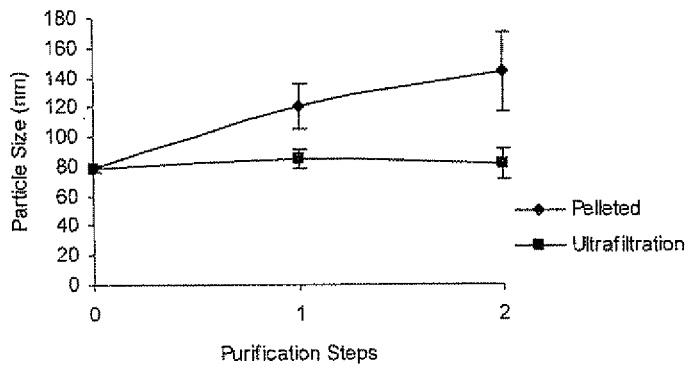
FIG. 5: PLGA-b-PEG NP size stability. (A) Effect of centrifugation vs. ultrafiltration on nanoparticle size (12000×g for 15 minutes vs. 3000×g for 15 minutes). (B) Effect of sucrose prior to lyopholization on nanoparticle size, after storage and resuspension.
Figure 5:
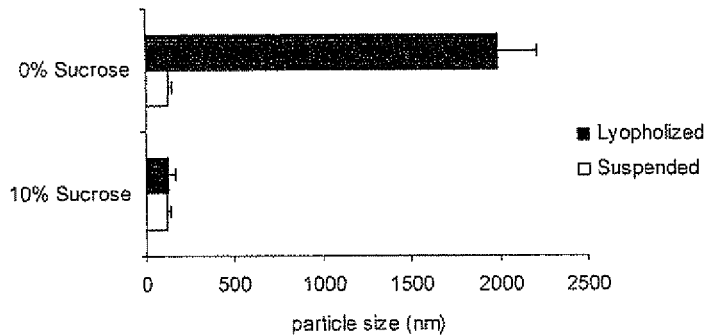

NPs formed by nanoprecipitation generally do not require surfactant; however, the lack of surfactant can cause NP aggregation after formulation. High-speed centrifugation, for example, can substantially increase particle size due to aggregation upon pelleting. After NPs (approximately 80 nm) were centrifuged at 10,000×g for 10 minutes, an increase in diameter of approximately 20%-30% was observed for each of the centrifugation steps (FIG. 5A). However, the mechanical force that causes aggregation can be substantially avoided by low-speed ultrafiltration (FIG. 5A). Use of a commercially available centrifuge filtration device reproducibly controls particle size during multiple washing steps.

For translation to clinical use of any biodegradable formulation, stability upon storage is a concern. Freeze-drying NPs and storing frozen in solid-state is a common approach, and sugars like sucrose can act as a lyoprotectant during the process (De Jaeghere et al., 2000, *Pharm. Dev. Technol.,* 5:473; and Konan et al., 2003, *Eur. J. Pharmaceutics Biopharmaceutics,* 55:115). Addition of 10% sucrose to an aqueous NP suspension (10 mg/mL) allows recovery of NPs of very similar size as originally formulated (FIG. 5B). Without sucrose as a lyoprotectant, NPs aggregated to a few micrometers in size and were not useful upon reconstitution for in vivo systemic delivery (FIG. 5B).

Association of Aptamer with Nanoparticle

Figure 6:
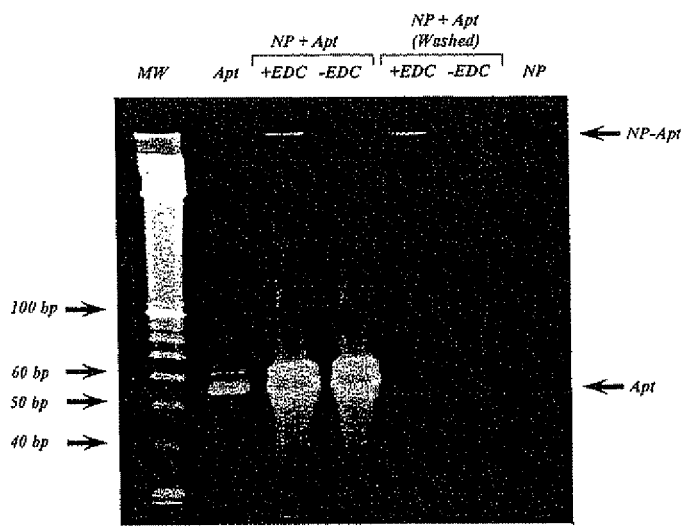
FIG. 6: Confirmation of nanoparticle-Apt association. A10 PSMA aptamer (Apt) was incubated with PLGA-b-PEG nanoparticles in the absence (−) or presence (+) of EDC. Reactions were resolved on a 10% TBE-Urea PAGE directly or after washing to remove any unassociated Apt. Bands corresponding to the A10 PSMA Apt and nanoparticle-Apt are indicated by arrows. Nucleic acid molecular weight marker (MW) is shown on left.

PAGE was utilized to examine the association of NPs with aptamers and to demonstrate successful removal of aptamers that had not associated with NPs after the reaction. The mixing of aptamer and NP without the addition of the coupling agent (−EDC, FIG. 6) did not show any band of unassociated aptamer, indicating a lack of non-specific interaction between the aptamer and NP. Association with the addition of EDC (+EDC, FIG. 6) leads to RNA bands consistent with RNA covalently bound to NPs and unable to run on the gel, both before and after washing. After repetitive washing by ultrafiltration, the unassociated aptamer was no longer detectable (FIG. 6).

Figure 7:
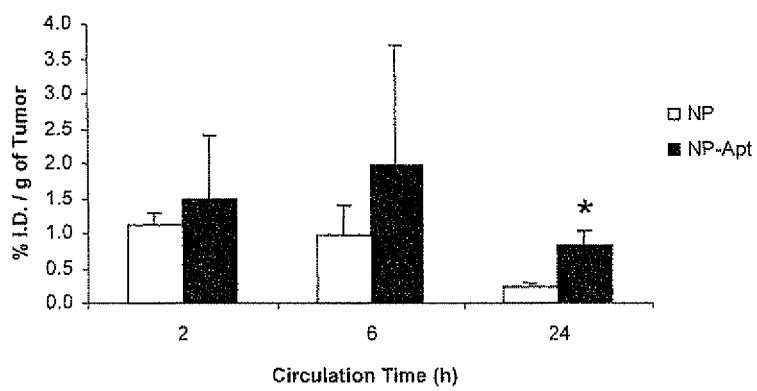
FIG. 7: Tumor targeting by PLGA-b-PEG nanoparticles and nanoparticle-Apt after systemic administration (mean±SD; n=4; * P<0.002).

In Vivo Tumor Targeting and Biodistribution of Nanoparticle-Aptamer Targeted Particles As a result of investigations of formulation parameters and their effects on NP size, an optimal NP formulation in terms of size and drug loading was chosen for in vivo study. For the study, $^{14}$C-paclitaxel (serving as a tracing agent) was encapsulated at a drug loading of 1% into the PLGA-b-PEG NPs. Paclitaxel is a taxane drug related to docetaxel and is available commercially as a radiochemical. The resulting NPs were sized at 156.8+/−3.9 nm, and after bioassociation with the aptamers, the final size of NP-Apt targeted particles was measured to be 188.1±4.0 nm. At all three time-points, the $^{14}$C-paclitaxel dose recovered in the tumor was higher for the NP-Apt targeted groups compared to the control NP groups (FIG. 7). The values in % injected dose per gram of tissue at 2, 6, and 24 hours for the NP-Apt group were 1.49±0.92, 1.98±1.72, and 0.83±0.21, respectively (mean±S.D., n=4). For the NP control group, the respective values at 2, 6, and 24 hours were 1.10±0.20, 0.96±0.44, and 0.22±0.07. At the 24 hour endpoint of the study, the level in the tumor was 3.77-fold higher for the NP-Apt group (p=0.002, n=4). At the 2 and 6 hour time-points, the level of NP-Apt in the tumor was 1.35-fold and 2.06-fold higher than the control, respectively, but this difference was not statistically significant. In both 2 and 6 hour groups, intra-tumoral concentrations of NP-Apt increased as compared to the NP control, while levels in most other tissues decreased in parallel to less NPs in circulation. While not wishing to be bound by any particular theory, it is possible that the concentration of recovered drug in the tumor over time shows both the enhanced permeability and retention (EPR) effect and the effect of targeting. The ability of the NP-Apt targeted particles to maintain a significantly higher concentration in the tumor at 24 hours is possibly due to uptake by the targeted LNCaP cells, while the NP group without targeting ligand diffused away from the tumor over time in the absence of cell uptake. Similar strong binding of the NP-Apt targeted particles to LNCaP cells was observed in vitro (Farokhzad et al., 2004, *Cancer Research,* 64:7668). It is possible that the concentration in the tumor for both groups declines from the 6 and 24 h time-points due to the burst effect of the NPs, which can release a large percentage of the drug during this time (Fonseca et al., 2002, *J. Control. Release,* 83:273). Drug released at the tumor site, if not internalized by the cells, can diffuse away or be clear from the site.

Figure 8:
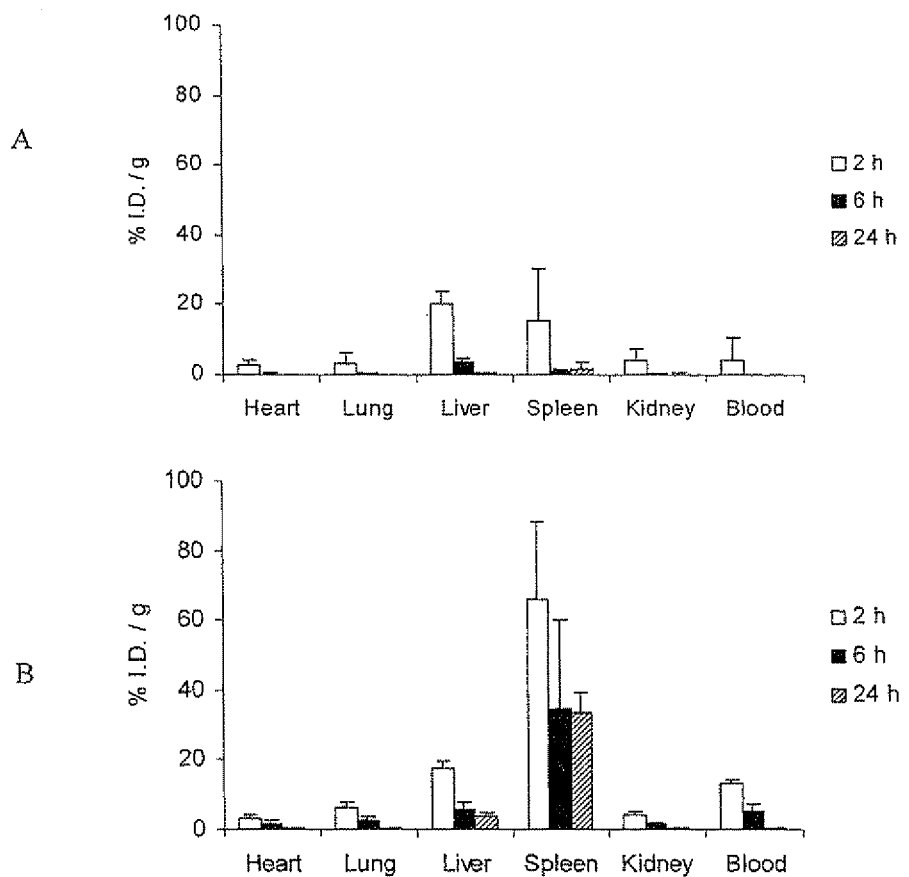
FIG. 8: Systemic biodistribution of (A) PLGA-b-PEG nanoparticles and (B) nanoparticle-Apt (mean±SD; n=4).

Biodistribution patterns to the heart, lungs, and kidneys did not show substantial accumulation in either group and were not significantly different (FIG. 8). Uptake by the reticuloendothelial system (RES), including the spleen and liver, was observed to be higher for NP-Apt targeted particles as compared to control NPs. The outer PEG layer, while providing an excellent stealth shield for the NP group, was modified in the NP-Apt group by association of aptamers with the particle surface. Aptamers are not considered to be immunogenic, and thus it is likely that the cause of the observed RES uptake was this disruption of the PEG shield. Further, the bioassociation resulted in a moderate increase in mean particle size compared to the NP group. The increased size can partially explain the increased uptake the spleen (Storm et al., 1995, *Adv. Drug Deliv. Rev.,* 17:31).

Equivalents and Scope

Those skilled in the art will recognize, or be able to ascertain using no more than routine experimentation, many equivalents to the specific embodiments of the invention, described herein. The scope of the present invention is not intended to be limited to the above Description, but rather is as set forth in the appended claims.

Those skilled in the art will recognize, or be able to ascertain using no more than routine experimentation, many equivalents to the specific embodiments of the invention described herein. The scope of the present invention is not intended to be limited to the above Description, but rather is as set forth in the appended claims.

In the claims articles such as "a," "an," and "the" may mean one or more than one unless indicated to the contrary or otherwise evident from the context. Thus, for example, reference to "a nanoparticle" includes a plurality of such nanoparticle, and reference to "the cell" includes reference to one or more cells known to those skilled in the art, and so forth. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process. Furthermore, it is to be understood that the invention encompasses all variations, combinations, and permutations in which one or more limitations, elements, clauses, descriptive terms, etc., from one or more of the listed claims is introduced into another claim. For example, any claim that is dependent on another claim can be modified to include one or more limitations found in any other claim that is dependent on the same base claim. Furthermore, where the claims recite a composition, it is to be understood that methods of using the composition for any of the purposes disclosed herein are included, and methods of making the composition according to any of the methods of making disclosed herein or other methods known in the art are included, unless otherwise indicated or unless it would be evident to one of ordinary skill in the art that a contradiction or inconsistency would arise.

Where elements are presented as lists, e.g., in Markush group format, it is to be understood that each subgroup of the elements is also disclosed, and any element(s) can be removed from the group. It should it be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not been specifically set forth in haec verba herein. It is noted that the term "comprising" is intended to be open and permits the inclusion of additional elements or steps.

Where ranges are given, endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise.

In addition, it is to be understood that any particular embodiment of the present invention that falls within the prior art may be explicitly excluded from any one or more of the claims. Since such embodiments are deemed to be known to one of ordinary skill in the art, they may be excluded even if the exclusion is not set forth explicitly herein. Any particular embodiment of the compositions of the invention (e.g., any aptamer, any disease, disorder, and/or condition, any linking agent, any method of administration, any therapeutic application, etc.) can be excluded from any one or more claims, for any reason, whether or not related to the existence of prior art.

The publications discussed above and throughout the text are provided solely for their disclosure prior to the filing date of the present application. Nothing herein is to be construed as an admission that the inventors are not entitled to antedate such disclosure by virtue of prior disclosure.

We claim:

1. A targeted particle comprising polymer conjugated to a surfactant, hydrophilic polymer or lipid,
    the particle having bound thereto a plurality of small molecule targeting moieties that specifically bind to the Zn2+ NAAG/PSMA binding pocket within prostate specific membrane antigen (PSMA) selected from the group consisting of 2-PMPA, GPI5232, VA-033 2MPPA, thiol and indole thiol based PSMA inhibitors, 3-(2-mercaptoethyl)-1H-indole-2-carboxylic acid derivative PSMA inhibitors, hydroxamate derivative PSMA inhibitors, PDBA-based PSMA inhibitors, and urea-based PSMA inhibitors, and
    having encapsulated or dispersed therein a therapeutic, diagnostic or prophylactic agent,
    wherein at least 80% of the particles have a greatest dimension less than 250 nm and have enhanced permeation through tumor vasculature and retention in tumor tissue as compared to particles greater than 250 nm.

2. The targeted particle of claim 1, wherein the polymer is selected from the group consisting of poly(lactide-co-glycolide) (PLGA), poly(lactic acid) (PLA), poly(glycolic acid) (PGA), polycaprolactone, and polyanhydrides.

3. The targeted particle of claim 1, wherein the polymer is PLA.

4. The targeted particle of claim 1, wherein the particle comprises two or more polymers.

5. The targeted particle of claim 4, wherein at least one polymer is selected from the group consisting of polyethylenes, polycarbonates, polyanhydrides, polyhydroxyacids, polypropylfumerates, polycaprolactones, polyamides, polyacetals, polyethers, polyesters, poly(orthoesters), polycyanoacrylates, polyvinyl alcohols, polyurethanes, polyphosphazenes, polyacrylates, polymethacrylates, polycyanoacrylates, polyureas, polystyrenes, polyamines, and combinations thereof.

6. The targeted particle of claim 4, wherein at least one polymer is selected from the group consisting of polyesters, polyanhydrides, polyethers, polyurethanes, polymethacrylates, polyacrylates, and polycyanoacrylates.

7. The targeted particle of claim 4, wherein at least one polymer is polyalkylene glycol.

8. The targeted particle of claim 4, wherein at least one polymer is polyethylene glycol (PEG).

9. The targeted particle of claim 1, wherein the conjugated polymer comprises a copolymer of two or more polymers.

10. The targeted particle of claim 9, wherein the conjugated copolymer is a copolymer of PLA and PEG.

11. The targeted particle of claim 1, wherein the targeted particle comprises a protein, lipid, or carbohydrate.

12. The targeted particle of claim 1, wherein the small molecule targeting moiety is selected from the group consisting of urea-based inhibitors.

13. The targeted particle of claim 1, wherein the therapeutic agent is selected from the group consisting of small molecules, proteins, nucleic acids, carbohydrates, lipids, and combinations thereof.

14. The targeted particle of claim 1, wherein the therapeutic agent is an anti-cancer agent.

15. The targeted particle of claim 1, wherein the therapeutic agent is selected from the group consisting of antibodies, recombinant antibodies, humanized antibodies, characteristic portions thereof, and combinations thereof.

16. The targeted particle of claim 1, wherein the therapeutic agent is an enzyme.

17. The targeted particle of claim 1, wherein the therapeutic agent is a small interfering RNA, a small hairpin RNA, or a microRNA.

18. The targeted particle of claim 1, wherein at least 90% of the particles have a greatest dimension less than 200 nm in diameter.

19. The targeted particle of claim 1, wherein the prophylactic agent is a vaccine.

20. The targeted particle of claim 1, wherein the therapeutic agent is docetaxel.

21. The targeted particle of claim 1, wherein the targeting moiety is associated with the particle via at least one covalent linkage.

22. A method of treating prostate cancer in a subject, comprising administering an effective amount to a subject in need thereof of particles comprising polymer conjugated to a surfactant, hydrophilic polymer or lipid, the particle having bound thereto a plurality of small molecule targeting moieties that specifically bind to the Zn2+ NAAG/PSMA binding pocket within prostate specific membrane antigen (PSMA) selected from the group consisting of 2-PMPA, GPI5232, VA-033, thiol and indole thiol based PSMA inhibitors, 3-(2-mercaptoethyl)-1H-indole-2-carboxylic acid derivative PSMA inhibitors, hydroxamate derivative PSMA inhibitors, PDBA-based PSMA inhibitors, and urea-based PSMA inhibitors, having encapsulated or dispersed therein a therapeutic, diagnostic or prophylactic agent, wherein at least 80% of the particles have a greatest dimension less than 250 nm and have enhanced permeation through tumor vasculature and retention in tumor tissue as compared to particles greater than 250 nm.

23. The method of claim 22, wherein the targeted particle further comprises a pharmaceutically acceptable excipient.

24. The method of claim 22, wherein the targeted particle is administered to the subject by an intravenous, intramuscular, intra-arterial, intramedullary, intrathecal, subcutaneous, or intraventricular, route.

25. The method of claim 22, wherein the targeted particle is administered directly to the prostate.

26. The method of claim 22, wherein the targeted particle is administered directly to prostate cancer cells.

27. The method of claim 26, wherein the targeted particle is administered directly to prostate cancer cells by topical administration.

28. The method of claim 26, wherein the targeted particle is administered directly to prostate cancer cells by injection into tissue comprising the prostate cancer cells.

29. The method of claim 26, wherein the targeted particle is administered to the subject by implantation of targeted particles at or near prostate cancer cells by stereotactic surgery.

30. The method of claim 26, wherein the targeted particle is administered to the subject by implantation of targeted particles at or near prostate cancer cells during surgical removal of a tumor.

31. A method of preparing particles comprising polymer conjugated to a surfactant, hydrophilic polymer or lipid, the particle having bound thereto a plurality of protein or small molecule targeting moieties that specifically bind to the particle having bound thereto a plurality of small molecule targeting moieties that specifically bind to the Zn2+ NAAG/PSMA binding pocket within prostate specific membrane antigen (PSMA) selected from the group consisting of 2-PMPA, GPI5232, VA-033, thiol and indole thiol based PSMA inhibitors, 3-(2-mercaptoethyl)-1H-indole-2-carboxylic acid derivative PSMA inhibitors, hydroxamate derivative PSMA inhibitors, PDBA-based PSMA inhibitors, and urea-based PSMA inhibitors, and having encapsulated or dispersed therein a therapeutic, diagnostic or prophylactic agent, wherein at least 80% of the particles have a greatest dimension less than 250 nm and have enhanced permeation through tumor vasculature and retention in tumor tissue as compared to particles greater than 250 nm, comprising nanoprecipitation or flow focusing fluidic channels of polymer conjugated to a surfactant, hydrophilic polymer or lipid, in combination with a therapeutic, diagnostic or prophylactic agent and targeting moieties that specifically binding to prostate specific membrane antigen selected from the group consisting of 2-PMPA, GPI5232, VA-033, thiol and indole thiol based PSMA inhibitors, 3-(2-mercaptoethyl)-1H-indole-2-carboxylic acid derivative PSMA inhibitors, hydroxamate derivative PSMA inhibitors, PDBA-based PSMA inhibitors, and urea-based PSMA inhibitors, and selecting the particles having a greatest dimension less than 250 nm.

32. A population of targeted particles, comprising
a particle comprising a polymeric matrix, wherein the polymeric matrix comprises a polyester;
a targeting moiety wherein the targeting moiety is a urea-based prostate specific membrane antigen (PSMA) inhibitor; and
a therapeutic agent;
wherein at least 80% of the particles have a greatest dimension less than 250 nm,
having encapsulated or dispersed therein a therapeutic, diagnostic or prophylactic agent, and
having enhanced permeation through tumor vasculature and retention in tumor tissue as compared to particles greater than 250 nm.

33. The targeted particle of claim 32, wherein the urea-based inhibitor is selected from the group consisting of ZJ 43, ZJ 11, ZJ 17, and ZJ 38.

34. The targeted particle of claim 1, wherein the conjugated polymer is a copolymer of PLA and PEG, and wherein the therapeutic agent is docetaxel.

35. The targeted particle of claim 34, wherein the greatest dimension of the particles is between 25 nm and 200 nm in diameter.

36. The targeted particle of claim 1, wherein the therapeutic agent is a taxane.

37. The targeted particle of claim 1, wherein the targeting moiety increases intratumor levels of the therapeutic agent by at least three-fold.

38. The targeted particle of claim 32, wherein at least 90% of the particles have a greatest dimension less than 250 nm.

39. The targeted particle of claim 1, wherein at least 80% of the particles have a greatest dimension less than 200 nm.

40. The targeted particle of claim 1, wherein at least 90% of the particles have a greatest dimension less than 200 nm.

41. The targeted particle of claim 32, wherein at least 80% of the particles have a greatest dimension less than 200 mm.

42. The targeted particle of claim 32, wherein at least 90% of the particles have a greatest dimension less than 200 nm.

43. The targeted particle of claim 1 having bound thereto a plurality of small molecule targeting moieties that specifically bind to the Zn2+ NAAG/PSMA binding pocket within prostate specific membrane antigen (PSMA) selected from the group consisting of 2-PMPA, GPI5232, VA-033, and 2-MPPA.

* * * * *

UNITED STATES PATENT AND TRADEMARK OFFICE
CERTIFICATE OF CORRECTION

| | | |
|---|---|---|
| PATENT NO. | : 8,709,483 B2 | Page 1 of 1 |
| APPLICATION NO. | : 12/239136 | |
| DATED | : April 29, 2014 | |
| INVENTOR(S) | : Farokhzad et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1021 days.

Signed and Sealed this
Twenty-ninth Day of September, 2015

Michelle K. Lee
*Director of the United States Patent and Trademark Office*